United States Patent
Park et al.

(10) Patent No.: US 10,154,990 B2
(45) Date of Patent: Dec. 18, 2018

(54) MEDICAMENTS FOR THE TREATMENT OR PREVENTION OF FIBROTIC DISEASES

(71) Applicant: Boehringer Ingelheim International GmbH, Ingelheim am Rhein (DE)

(72) Inventors: John Edward Park, Warthausen (DE); Gerald Juergen Roth, Biberach (DE); Armin Heckel, Biberach (DE); Nveed Chaudhary, Southampton (GB); Trixi Brandl, Allschwil (CH); Georg Dahmann, Warthausen-Birkenhard (DE); Matthias Grauert, Biberach an der Riss (DE)

(73) Assignee: Boehringer Ingelheim International GmbH, Ingelheim am Rhein (DE)

( * ) Notice: Subject to any disclaimer, the term of this patent is extended or adjusted under 35 U.S.C. 154(b) by 19 days.

(21) Appl. No.: 14/982,179

(22) Filed: Dec. 29, 2015

(65) Prior Publication Data

US 2016/0136133 A1    May 19, 2016

Related U.S. Application Data

(63) Continuation of application No. 14/184,821, filed on Feb. 20, 2014, which is a continuation of application No. 12/645,151, filed on Dec. 22, 2009, which is a continuation of application No. 11/275,223, filed on Dec. 20, 2005.

(30) Foreign Application Priority Data

Dec. 24, 2004 (EP) .................. 04030770

(51) Int. Cl.
| | | |
|---|---|---|
| *A61K 31/4045* | (2006.01) | |
| *A61K 45/06* | (2006.01) | |
| *A61K 31/404* | (2006.01) | |
| *A61K 31/44* | (2006.01) | |
| *A61K 31/445* | (2006.01) | |
| *A61K 31/495* | (2006.01) | |
| *A61K 31/496* | (2006.01) | |
| *A61K 31/4178* | (2006.01) | |
| *A61K 31/454* | (2006.01) | |
| *A61K 31/5377* | (2006.01) | |
| *A61K 31/551* | (2006.01) | |
| *C07D 209/34* | (2006.01) | |
| *C07D 401/12* | (2006.01) | |
| *C07D 403/12* | (2006.01) | |
| *C07D 295/155* | (2006.01) | |
| *C07D 295/215* | (2006.01) | |

(52) U.S. Cl.
CPC ........ *A61K 31/4045* (2013.01); *A61K 31/404* (2013.01); *A61K 31/4178* (2013.01); *A61K 31/44* (2013.01); *A61K 31/445* (2013.01); *A61K 31/454* (2013.01); *A61K 31/495* (2013.01); *A61K 31/496* (2013.01); *A61K 31/5377* (2013.01); *A61K 31/551* (2013.01); *A61K 45/06* (2013.01); *C07D 209/34* (2013.01); *C07D 295/155* (2013.01); *C07D 295/215* (2013.01); *C07D 401/12* (2013.01); *C07D 403/12* (2013.01)

(58) Field of Classification Search
CPC .. A61K 2300/00; A61K 31/404; A61K 31/44; A61K 31/445; A61K 31/496; A61K 31/4045; A61K 31/4178; A61L 2300/00
USPC ........ 514/218, 235.2, 254.09, 323, 397, 418
See application file for complete search history.

(56) References Cited

U.S. PATENT DOCUMENTS

| | | | |
|---|---|---|---|
| 6,638,965 B2 | 10/2003 | Walter et al. | |
| 6,762,180 B1 * | 7/2004 | Roth ............... | C07D 209/30 |
| | | | 514/228.2 |
| 6,794,395 B1 | 9/2004 | Roth et al. | |
| 6,858,641 B2 | 2/2005 | Roth et al. | |
| 7,119,093 B2 | 10/2006 | Roth et al. | |
| 7,148,249 B2 | 12/2006 | Kley et al. | |

(Continued)

FOREIGN PATENT DOCUMENTS

| | | |
|---|---|---|
| CA | 2323111 A1 | 10/1999 |
| CA | 2328291 A1 | 12/1999 |

(Continued)

OTHER PUBLICATIONS

Roschmann et al., Seminars in Arthiritis and Rheumatism, Feb. 1987, vol. 16, issue 3, abstract.*

(Continued)

*Primary Examiner* — Sreenivasan Padmanabhan
*Assistant Examiner* — Courtney A Brown
(74) *Attorney, Agent, or Firm* — David L. Kershner

(57) ABSTRACT

The present invention relates to the use of indolinones of general formula

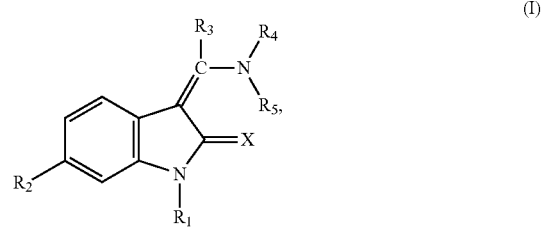

(I)

substituted in the 6 position, wherein
$R_1$ to $R_5$ and X are defined as in claim 1, the isomers and the salts thereof, particularly the physiologically acceptable salts thereof, as a medicament for the prevention or treatment of specific fibrotic diseases.

5 Claims, 6 Drawing Sheets

Specification includes a Sequence Listing.

(56) References Cited

U.S. PATENT DOCUMENTS

| | | |
|---|---|---|
| 7,989,474 B2 | 8/2011 | Roth et al. |
| 2006/0148883 A1 | 7/2006 | Park et al. |
| 2009/0048267 A1 | 2/2009 | Park et al. |
| 2015/0265610 A1 | 9/2015 | Stefanic et al. |
| 2016/0136133 A1 | 5/2016 | Park et al. |
| 2016/0250218 A1 | 9/2016 | Stefanic et al. |

FOREIGN PATENT DOCUMENTS

| | | | |
|---|---|---|---|
| CA | 2342622 A1 | 4/2000 | |
| CA | 2387013 A1 | 4/2001 | |
| DE | 19815020 A1 | 10/1999 | |
| WO | 1996040116 A1 | 12/1996 | |
| WO | 1999015500 A1 | 4/1999 | |
| WO | 1999052869 A1 | 10/1999 | |
| WO | 1999062882 A1 | 12/1999 | |
| WO | 2000018734 A1 | 4/2000 | |
| WO | 2000056710 A1 | 9/2000 | |
| WO | 2000073297 A1 | 12/2000 | |
| WO | 2001016130 A1 | 3/2001 | |
| WO | 2001027080 A2 | 4/2001 | |
| WO | 2001027081 A1 | 4/2001 | |
| WO | 2001040215 A1 | 6/2001 | |
| WO | 2001072711 A1 | 10/2001 | |
| WO | 2002036564 A1 | 5/2002 | |
| WO | 2002081445 A1 | 10/2002 | |
| WO | 2004013099 A1 | 2/2004 | |
| WO | 2004017948 A2 | 3/2004 | |
| WO | WO 2004017948 A2 * | 3/2004 | ............. A61K 3/404 |
| WO | 2004026829 A2 | 4/2004 | |
| WO | 2004096224 A2 | 11/2004 | |
| WO | WO 2004096224 A2 * | 11/2004 | ........... A61K 31/404 |

OTHER PUBLICATIONS

Molina et al., Harefuah, Nov. 2002, vol. 141, issue 11, abstract.*
Panos et al., American Journal of Medicine, Apr. 1990, vol. 88, issue 4, abstract.*
Clements et al.,Systemic Sclerosis, Nov. 4, 2003, chapter 23.*
American Thoracic Society., Idiopatic pulmonary fibrosis: Diagnosis and Treatment, American Thoracic Society and the European Respiratory Society, Am. J. of Respir. Crit. Care Med., 1999, vol. 161, pp. 647-664.
American Thoracic Society/European Respiratory Society International Multidisciplinary Consensus Classification of Classification of the Idiopathaic Interstitial Pneumonias, Am J Respir Crit Care Med, 2002, vol. 165. pp. 277-304.
Burke, T.; Protein-Tyrosine Kinases: Potential Targets for Anticancer Drug Development; Stem Cells; 1994; vol. 12; pp. 1-16.
Chaudhary et al., Pharmacologic Differentiation of Inflammation and Fibrosis in the Rat Bleomycin Model, American Journal of Respiratory and Critical Care Medicine, 2006, vol. 173, pp. 769-776.
Daniels et al., Imatinib treatment for idiopathic pulmonary fibrosis: randomized placebo-controlled trial results, Am J Respir Crit Care Med, 2010, 181, pp. 604-610.
Downey et al.,Resolving the Scar of Pulmonary Fibrosis, New England Journal of Medicine, 2011, vol. 356, No. 12, pp. 1140-1141.
Excerpt from www.lungeninformationsdienst.de. Retrieved from the internet on Jun. 20, 2014.
Expert declaration of Robert Strieter—including annexed documents. Filed Oct. 1, 2014.
Garantziotis et al., Pulmonary fibrosis: thinking outside of the lung, J. Clin. Invest., 2004, vol. 144, pp. 319-321.
Gomer et al., Investigational approaches to therapies for idiopathic pulmonary fibrosis, Expert Opinion Investig. Drugs, 2010, vol. 19, No. 6, pp. 737-742.
Hilberg et al., BIBF1120 a novel, small molecule triple angiokinase inhibitor: profilling as a clinical candidate for canser therapy, European Journal of Cancer Supplements, 2004, vol. 2, No. 8, pp. 3-228.
International Search Report (Form PCT/ISA/220) for corresponding PCT/EP2005/057002, dated Feb. 16, 2007.
Kuroki et al., Repression of Bleomycin-Induces Pneumopathy by TNF, The Journal of Immunology, 2003, 170, pp. 567-574.
Nintedanib for idiopathic pulmonary fibrosis—first line, Horizon Scanning Centre, 2013, pp. 1-9.
Opposition fron EP application 05823930, dated Apr. 2, 2015, corresponds to U.S. Appl. No. 14/184,821.
Prescribing Information for OFEV® (nintedanib) capsules, 2014.
Press Release "FDA approves Ofev to treat idiopathic pulmonary fibrosis", Oct. 15, 2014.
Raghu et al., Treatment of Idiopatic Pulmonary Fibrosis with a New Antifibrotic Agent, Pirfenidone, American Journal of Respiratory and Critical Care Medicine, 1999, vol. 159, pp. 1062-1069.
Randomized Trial of Acetylcysteine in Idiopathic Pulmonary Fibrosis, N Engl J Med, 2014, 370, pp. 2093-2101.
Richeldi et al., Efficacy and Safety of Nintedanib in Idiopathic Pulmonary Fibrosis, N Engl J Med, 2014, 370, pp. 2071-2082.
Richeldi et al., Efficacy of a Tyrosine Kinase Inhibitor in Idiopathic Pulmonary Fibrosis, The New Eng. Journal of Medicine, 2011, vol. 365, No. 12, pp. 1079-1087.
Roschmann et al., Seminars in Arthritis and Rheumatism, vol. 16, issue 3, abstract.
Schaefer et al., Antifibrotic activities of pirfenidone in animal models, European Respiratory Review, 2011, vol. 20, No. 120, pp. 85-97.
Selman et al., Idiopathic Pulmonary Fibrosis: Prevailing and Evolving Hypotheses about Its Pathogenesis and Implications for Therapy, Ann. Intern. Med., 2001, No. 134, vol. 2, pp. 136-151.
Sogut et al., Erdosteine prevents bleomycin-induced pulmonary fibrosis in rats, European Journal of Pharmacology, 2004, vol. 494, pp. 213-220.
Traxler, P.; Tyrosine kinases as targets in cancer therapy—successes and failures; Oncologic; 2003; vol. 7; pp. 215-234.
Zandman-Goddard, New Therapeutic Strategies for systemic sclerosis-a critical analysis of the literature, Clinical and Developmental Immunology, 2005, vol. 12, p. 165-173.
Hilberg, F et al., "Efficacy of Bibf 1120, a potent triple angiokinase inhibitor, in models of human non-small cell ung cancer is augmented by chemotherapy." Journal of Thoracic Oncology, 2007, vol. 2, No. 8, Suppl. 4, p. S380.
U.S. Appl. No. 14/848,563, tiled Sep. 9, 2015, Inventor: Roman Messerschmid.
U.S. Appl. No. 15/204,277, filed Jul. 7, 2016, Inventor: Roman Messerschmid.

* cited by examiner

MEDICAMENTS FOR THE TREATMENT OR PREVENTION OF FIBROTIC DISEASES

The present invention relates to a new use of indolinones of general formula

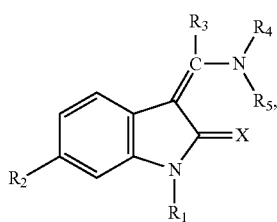

substituted in the 6 position, the tautomers, the diastereomers, the enantiomers, the mixtures thereof and the salts thereof, particularly the physiologically acceptable salts thereof.

BACKGROUND

Compounds of the above general formula I, the tautomers, the diastereomers, the enantiomers, the mixtures thereof and the salts thereof, particularly the physiologically acceptable salts thereof, have been described in WO 01/27081 and WO 04/13099 as having valuable pharmacological properties, in particular an inhibiting effect on various kinases, especially receptor tyrosine kinases such as VEGFR2, PDGFRα, PDGFRβ, FGFR1, FGFR3, EGFR, HER2, IGF1R and HGFR, as well as complexes of CDK's (Cyclin Dependent Kinases) such as CDK1, CDK2, CDK3, CDK4, CDK5, CDK6, CDK7, CDK8 and CDK9 with their specific cyclins (A, B1, B2, C, D1, D2, D3, E, F, G1, G2, H, I and K) and to viral cyclin (cf. L. Mengtao in J. Virology 71(3), 1984-1991 (1997)), and on the proliferation of cultivated human cells, in particular endothelial cells, e.g. in angiogenesis, but also on the proliferation of other cells, in particular tumour cells.

However, none of these compounds have been described for their use in the treatment or prevention of the fibrotic diseases referred to in the present invention.

Remodeling is a normal response to tissue injury and inflammation that is observed in many tissues throughout the body. After resolution of the inflammation and repair of tissue damage, the tissue is generally returned to its original condition. Excessive uncontrolled tissue repair or the failure to stop remodeling when it is no longer required leads to condition known as fibrosis. Fibrosis is characterized by excessive deposition of extracellular matrix components and overgrowth of fibroblasts. Fibrosis can occur in all tissues but is especially prevalent in organs with frequent exposure to chemical and biological insults including the lung, skin, digestive tract, kidney, and liver (Eddy, 1996, J Am Soc Nephrol, 7(12):2495-503; Dacic et al., 2003, Am J Respir Cell Mol Biol, 29S: S5-9; Wynn, 2004, Nat Rev Immunol, 4(8):583-94). Fibrosis often severely compromises the normal function(s) of the organ and many fibrotic diseases are, in fact, life-threatening or severely disfiguring, such as idiopathic pulmonary fibrosis (IPF), liver cirrhosis, scleroderma, or renal fibrosis. Treatment options for these diseases are often limited to organ transplantation, a risky and expensive procedure.

A large body of literature implicates the platelet-derived growth factor (PDGF), fibroblast growth factor (FGF), vascular endothelial growth factor (VEGF), epidermal growth factor (EGF), and transforming growth factor beta (TGFb) growth factor families in the induction or persistence of fibrosis (Levitzki, Cytokine Growth Factor Rev, 2004, 15(4):229-35; Strutz et al., Kidney Intl, 2000, 57:1521-38; Strutz et al., 2003, Springer Semin Immunopathol, 24:459-76; Rice et al., 1999, Amer J Pathol, 155(1):213-221; Broekelmann et al., 1991, Proc Nat Acad Sci, 88:6642-6; Wynn, 2004, Nat Rev Immunol, 4(8):583-94).

PDGF, EGF and FGF family members are potent mitogens for mesenchymal cells such as smooth muscle cells, myofibroblasts and fibroblasts (Benito et al., 1993, Growth Regul 3(3):172-9; Simm et al, 1998, Basic Res Cardiol, 93(S3):40-3; Klagsburn, Prog Growth Factor Res, 1989, 1(4):207-35; Kirkland et al., 1998, J Am Soc Nephrol, 9(8):1464-73), the very cells which supplant normal tissue in fibrosis and are believed to play a role in tissue remodeling (Abboud, 1995, Annu Rev Physiol., 57:297-309; Jinnin et al., 2004, J Cell Physiol, online; Martinet et al., 1996, Arch Toxicol 18:127-39; Desmouliere, Cell Biology International, 1995, 19:471-6; Jelaska et al., Springer Semin Immunopathol, 2000, 21:385-95).

Inhibition of PDGF attenuates both liver fibrosis and lung fibrosis in experimental models, suggesting fibrosis in different organs may have a common origin (Borkham-Kamphorst et al., 2004, Biochem Biophys Res Commun; Rice et al., 1999, Amer J Pathol, 155(1):213-221). An EGF receptor kinase inhibitor was also active in this lung fibrosis model. Three-fold overexpression of an EGF family member, HB-EGF, in mouse pancreas islets was sufficient to cause development of fibrosis in both the exocrine and endocrine compartments (Means et al., 2003, Gastroenterology, 124 (4):1020-36).

Similarly, FGF1/FGF2-deficient mice show dramatically decreased liver fibrosis after chronic carbon tetrachloride (CCl4) exposure (Yu et al., 2003, Am J Pathol, 163(4):1653-62). FGF expression is increased in human renal interstitial fibrosis where it strongly correlates with interstitial scarring (Strutz et al., 2000, Kidney Intl, 57:1521-38) as well as in a model of experimental lung fibrosis (Barrios et al., 1997, Am J Physiol, 273 (2 Pt 1):L451-8), again lending credence to the idea that fibrosis in various tissues has a common basis.

In addition, elevated levels of VEGF have been observed in several studies in persons with asthma (Hoshino et al., 2001, J Allergy Clin Immunol 107:1034-39; Hoshino et al. 2001, J Allergy Clin Immunol 107:295-301; Kanazawa et al. 2002, Thorax 57:885-8; Asai et al., J Allergy Clin Immunol 110:571-5, 2002; Kanazawa et al., 2004, Am J Respir Crit Care Med, 169:1125-30). Inducible expression of VEGF in a transgenic mouse model induces an asthma-like phenotype, edema, angiogenesis and smooth muscle hyperplasia (Lee et al., 2004, Nature Med 10:1095-1103).

Finally, TGFb stimulates production of extracellular matrix proteins including fibronectin and collagens and is believed to play an important role in fibrosis in many tissues (Leask et al., 2004, FASEB J 18(7):816-27; Bartram et al., 2004, Chest 125(2):754-65; Strutz et al., 2003, Springer Semin Immunopathol, 24:459-76; Wynn, 2004, Nat Rev Immunol, 4(8):583-94). Inhibitors of TGFb production and signaling pathways are active in a number of fibrosis animal models (Wang et al., 2002, Exp Lung Res, 28:405-17; Laping, 2003, Curr Opin Pharmacol, 3(2):204-8).

As summarized above, several growth factors are upregulated in fibrosis and the inhibition of a single factor seems to reduce the severity of fibrosis in the fibrosis models.

SUMMARY OF THE INVENTION

Surprisingly, we found that the compounds of above general formula I are effective in the treatment or prevention of specific fibrotic diseases.

The present invention thus relates to the use of the compounds of above general formula I for the preparation of a medicament for the treatment or prevention of specific fibrotic diseases.

The present invention also relates to a method for the treatment or prevention of specific fibrotic diseases, by administration to a patient in need thereof of a pharmaceutical composition comprising a compound of above general formula I, together with a pharmaceutically suitable carrier. The expression "patient" is meant to comprise the mammalian animal body, preferably the human body.

The present invention further relates to a pharmaceutical composition for the treatment or prevention of specific fibrotic diseases which comprises a compound of above general formula I alone or in combination with one or more further therapeutic agents.

DETAILED DESCRIPTION OF THE INVENTION

Figure 1A:
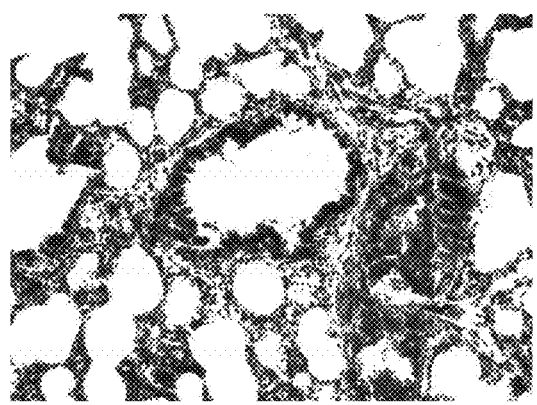
FIG. 1A depicts lung tissue removed from a rat from a control group of the experiment described in Example B1(A) which received saline and vehicle (0.1% Natrosol) instead of bleomycin intratracheally.

In accordance with the present invention, the compounds of above general formula I are the compounds

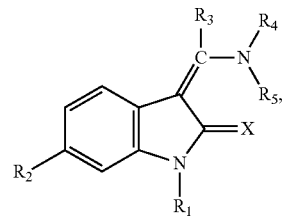

(I)

in which

X denotes an oxygen or sulphur atom, $R_1$ denotes a hydrogen atom or a prodrug group such as a $C_{1-4}$-alkoxycarbonyl or $C_{2-4}$-alkanoyl group, $R_2$ denotes a carboxy group, a straight-chain or branched $C_{1-6}$-alkoxy-carbonyl group, a $C_{4-7}$-cycloalkoxy-carbonyl or an aryloxycarbonyl group, a straight-chain or branched $C_{1-6}$-alkoxy-carbonyl group, which is terminally substituted in the alkyl moiety by a phenyl, heteroaryl, carboxy, $C_{1-3}$-alkoxy-carbonyl, aminocarbonyl, $C_{1-3}$-alkylamino-carbonyl or di-($C_{1-3}$-alkyl)-aminocarbonyl group, a straight-chain or branched $C_{2-6}$-alkoxy-carbonyl group, which is terminally substituted in the alkyl moiety by a chlorine atom or a hydroxy, $C_{1-3}$-alkoxy, amino, $C_{1-3}$-alkylamino or di-($C_{1-3}$-alkyl)-amino group, an aminocarbonyl or methylaminocarbonyl group, an ethylaminocarbonyl group optionally substituted in the 2 position of the ethyl group by a hydroxy or $C_{1-3}$-alkoxy group or a di-($C_{1-2}$-alkyl)-aminocarbonyl group, $R_3$ denotes a hydrogen atom, a $C_{1-6}$-alkyl, $C_{3-7}$-cycloalkyl, trifluoromethyl or heteroaryl group, a phenyl or naphthyl group, a phenyl or naphthyl group mono- or disubstituted by a fluorine, chlorine, bromine or iodine atom, by a trifluoromethyl, $C_{1-3}$-alkyl or $C_{1-3}$-alkoxy group, whilst in the event of disubstitution the substituents may be identical or different and wherein the abovementioned unsubstituted as well as the mono- and disubstituted phenyl and naphthyl groups may additionally be substituted by a hydroxy, hydroxy-$C_{1-3}$-alkyl or $C_{1-3}$-alkoxy-$C_{1-3}$-alkyl group, by a cyano, carboxy, carboxy-$C_{1-3}$-alkyl, $C_{1-3}$-alkoxycarbonyl, aminocarbonyl, $C_{1-3}$-alkylamino-carbonyl or di-($C_{1-3}$-alkyl)-aminocarbonyl group, by a nitro group, by an amino, $C_{1-3}$-alkylamino, di-($C_{1-3}$-alkyl)-amino or amino-$C_{1-3}$-alkyl group, by a $C_{1-3}$-alkylcarbonylamino, N—($C_{1-3}$-alkyl)-$C_{1-3}$-alkylcarbonylamino, $C_{1-3}$-alkylcarbonylamino-$C_{1-3}$-alkyl, N—($C_{1-3}$-alkyl)-$C_{1-3}$-alkylcarbonylamino-$C_{1-3}$-alkyl, $C_{1-3}$-alkyl-sulphonylamino, $C_{1-3}$-alkylsulphonylamino-$C_{1-3}$-alkyl, N—($C_{1-3}$-alkyl)-$C_{1-3}$-alkylsulphonylamino-$C_{1-3}$-alkyl or aryl-$C_{1-3}$-alkylsulphonylamino group, by a cycloalkylamino, cycloalkyleneimino, cycloalkyleneiminocarbonyl, cycloalkyleneimino-$C_{1-3}$-alkyl, cycloalkyleneiminocarbonyl-$C_{1-3}$-alkyl or cycloalkyleneiminosulphonyl-$C_{1-3}$-alkyl group having 4 to 7 ring members in each case, whilst in each case the methylene group in position 4 of a 6- or 7-membered cycloalkyleneimino group may be replaced by an oxygen or sulphur atom, by a sulphinyl, sulphonyl, —NH or —N($C_{1-3}$-alkyl) group, or by a heteroaryl or heteroaryl-$C_{1-3}$-alkyl group, $R_4$ denotes a $C_{3-7}$-cycloalkyl group, whilst the methylene group in the 4 position of a 6- or 7-membered cycloalkyl group may be substituted by an amino, $C_{1-3}$-alkylamino or di-($C_{1-3}$-alkyl)-amino group or replaced by an —NH or —N($C_{1-3}$-alkyl) group, or a phenyl group substituted by the group $R_6$, which may additionally be mono- or disubstituted by fluorine, chlorine, bromine or iodine atoms, by $C_{1-3}$-alkyl, trifluoromethyl, hydroxy, $C_{1-3}$-alkoxy, carboxy, $C_{1-3}$-alkoxycarbonyl, amino, acetylamino, $C_{1-3}$-alkyl-sulphonyl-amino, aminocarbonyl, $C_{1-3}$-alkyl-aminocarbonyl, di-($C_{1-3}$-alkyl)-aminocarbonyl, aminosulphonyl, $C_{1-3}$-alkyl-aminosulphonyl, di-($C_{1-3}$-alkyl)-aminosulphonyl, nitro or cyano groups, wherein the substituents may be identical or different and wherein $R_6$ denotes a hydrogen, fluorine, chlorine, bromine or iodine atom, a cyano, nitro, amino, $C_{1-5}$-alkyl, $C_{3-7}$-cycloalkyl, trifluoromethyl, phenyl, tetrazolyl or heteroaryl group, the group of formula

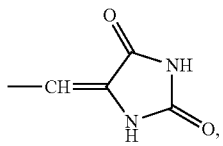

wherein the hydrogen atoms bound to a nitrogen atom may in each case be replaced independently of one another by a $C_{1-3}$-alkyl group, a $C_{1-3}$-alkoxy group, a $C_{1-3}$-alkoxy-$C_{1-3}$-alkoxy, phenyl-$C_{1-3}$-alkoxy, amino-$C_{2-3}$-alkoxy, $C_{1-3}$-alkylamino-$C_{2-3}$-alkoxy, di-($C_{1-3}$-alkyl)-amino-$C_{2-3}$-alkoxy, phenyl-$C_{1-3}$-alkylamino-$C_{2-3}$-alkoxy, N—($C_{1-3}$-alkyl)-phenyl-$C_{1-3}$-alkylamino-$C_{2-3}$-alkoxy, $C_{5-7}$-cycloalkyleneimino-$C_{2-3}$-alkoxy or $C_{1-3}$-alkylmercapto group, a carboxy, $C_{1-4}$-alkoxycarbonyl, aminocarbonyl, $C_{1-3}$-alkyl-amino-carbonyl, N—($C_{1-5}$-alkyl)-$C_{1-3}$-alkylaminocarbonyl, phenyl-$C_{1-3}$-alkylamino-carbonyl, N—($C_{1-3}$-alkyl)-phenyl-$C_{1-3}$-alkylamino-carbonyl, piperazinocarbonyl or N—($C_{1-3}$-alkyl)-piperazinocarbonyl group, a $C_{1-3}$-alkylaminocarbonyl or N—($C_{1-5}$-alkyl)-$C_{1-3}$-alkylaminocarbonyl group wherein an alkyl moiety is substituted by a carboxy or $C_{1-3}$-alkoxycarbonyl group or in the 2 or 3 position by a di-($C_{1-3}$-alkyl)-amino, piperazino, N—($C_{1-3}$-alkyl)-piperazino or a 4- to 7-membered cycloalkyleneimino group, a $C_{3-7}$-cycloalkyl-carbonyl group, wherein the methylene group in the 4 position of the 6- or 7-membered cycloalkyl moiety may be substituted by an amino, $C_{1-3}$-alkylamino or di-($C_{1-3}$-alkyl)-amino group or replaced by an —NH or —N($C_{1-3}$-alkyl) group, a 4- to 7-membered cycloalkyleneimino group wherein a methylene group linked to the imino group may be replaced by a carbonyl or sulphonyl group or the cycloalkylene moiety may be fused to a phenyl ring or one or two hydrogen atoms may each be replaced by a $C_{1-3}$-alkyl group and/or in each case the methylene group in the 4 position of a 6- or 7-membered cycloalkyleneimino group may be substituted by a carboxy, $C_{1-3}$-alkoxycarbonyl, aminocarbonyl, $C_{1-3}$-alkylaminocarbonyl, di-($C_{1-3}$-alkyl)-aminocarbonyl, phenyl-$C_{1-3}$-alkylamino or N—($C_{1-3}$-alkyl)-phenyl-$C_{1-3}$-alkylamino group or may be replaced by an oxygen or sulphur atom, by a sulphinyl, sulphonyl, —NH, —N($C_{1-3}$-alkyl), —N(phenyl), —N($C_{1-3}$-alkyl-carbonyl) or —N(benzoyl) group, a $C_{1-4}$-alkyl group substituted by the group $R_7$, wherein $R_7$ denotes a $C_{3-7}$-cycloalkyl group, whilst the methylene group in the 4 position of a 6- or 7-membered cycloalkyl group may be substituted by an amino, $C_{1-3}$-alkylamino or di-($C_{1-3}$-alkyl)-amino group or replaced by an —NH or —N($C_{1-3}$-alkyl) group or in a 5- to 7-membered cycloalkyl group a —(CH$_2$)$_2$ group may be replaced by a —CO—NH group, a —(CH$_2$)$_3$ group may be replaced by a —NH—CO—NH or —CO—NH—CO group or a —(CH$_2$)$_4$ group may be replaced by a —NH—CO—NH—CO group, whilst in each case a hydrogen atom bound to a nitrogen atom may be replaced by a $C_{1-3}$-alkyl group, an aryl or heteroaryl group, a hydroxy or $C_{1-3}$-alkoxy group, an amino, $C_{1-7}$-alkylamino, di-($C_{1-7}$-alkyl)-amino, phenylamino, N-phenyl-$C_{1-3}$-alkyl-amino, phenyl-$C_{1-3}$-alkylamino, N—($C_{1-3}$-alkyl)-phenyl-$C_{1-3}$-alkylamino or di-(phenyl-$C_{1-3}$-alkyl)-amino group, an ω-hydroxy-$C_{2-3}$-alkyl-amino, N—($C_{1-3}$-alkyl)-ω-hydroxy-$C_{2-3}$-alkyl-amino, di-(ω-hydroxy-$C_{2-3}$-alkyl)-amino, di-(ω-($C_{1-3}$-alkoxy)-$C_{2-3}$-alkyl)-amino or N-(di-oxolan-2-yl)-$C_{1-3}$-alkyl-amino group, a $C_{1-3}$-alkylcarbonylamino-$C_{2-3}$-alkyl-amino or $C_{1-3}$-alkylcarbonylamino-$C_{2-3}$-alkyl-N—($C_{1-3}$-alkyl)-amino group, a $C_{1-3}$-alkylsulphonylamino, N—($C_{1-3}$-alkyl)-$C_{1-3}$-alkylsulphonylamino, $C_{1-3}$-alkylsulphonylamino-$C_{2-3}$-alkyl-amino or $C_{1-3}$-alkylsulphonylamino-$C_{2-3}$-alkyl-N—($C_{1-3}$-alkyl)-amino group, a hydroxycarbonyl-$C_{1-3}$-alkylamino or N—($C_{1-3}$-alkyl)-hydroxycarbonyl-$C_{1-3}$-alkyl-amino group, a guanidino group wherein one or two hydrogen atoms may each be replaced by a $C_{1-3}$-alkyl group, a group of formula $$—N(R_8)—CO—(CH_2)_n—R_9 \quad \text{(II)},$$

wherein $R_8$ denotes a hydrogen atom or a $C_{1-3}$-alkyl group, n denotes one of the numbers 0, 1, 2 or 3 and $R_9$ denotes an amino, $C_{1-4}$-alkylamino, di-($C_{1-4}$-alkyl)-amino, phenylamino, N—($C_{1-4}$-alkyl)-phenylamino, benzylamino, N—($C_{1-4}$-alkyl)-benzylamino or $C_{1-4}$-alkoxy group, a 4- to 7-membered cycloalkyleneimino group, whilst in each case the methylene group in the 4 position of a 6- or 7-membered cycloalkyleneimino group may be replaced by an oxygen or sulphur atom, by a sulphinyl, sulphonyl, —NH, —N($C_{1-3}$-alkyl), —N(phenyl), —N($C_{1-3}$-alkyl-carbonyl) or —N(benzoyl) group, or, if n denotes one of the numbers 1, 2 or 3, it may also denote a hydrogen atom, a group of formula $$—N(R_{10})—(CH_2)_m—(CO)_o—R_{11} \quad \text{(III)},$$

wherein $R_{10}$ denotes a hydrogen atom, a $C_{1-3}$-alkyl group, a $C_{1-3}$-alkylcarbonyl, arylcarbonyl, phenyl-$C_{1-3}$-alkyl-carbonyl, $C_{1-3}$-alkylsulphonyl, arylsulphonyl or phenyl-$C_{1-3}$-alkyl-sulphonyl group, m denotes one of the numbers 1, 2, 3 or 4, o denotes the number 1 or, if m denotes one of the numbers 2, 3 or 4, o may also denote the number 0 and $R_{11}$ denotes an amino, $C_{1-4}$-alkylamino, di-($C_{1-4}$-alkyl)-amino, phenylamino, N—($C_{1-4}$-alkyl)-phenylamino, benzylamino, N—($C_{1-4}$-alkyl)-benzylamino, $C_{1-4}$-alkoxy or $C_{1-3}$-alkoxy-$C_{1-3}$-alkoxy group, a di-($C_{1-4}$-alkyl)-amino- $C_{1-3}$-alkylamino group optionally substituted in the 1 position by a $C_{1-3}$-alkyl group or a 4- to 7-membered cycloalkyleneimino group, wherein the cycloalkylene moiety may be fused to a phenyl ring or in each case the methylene group in the 4 position of a 6- or 7-membered cycloalkyleneimino group may be replaced by an oxygen or sulphur atom, by a sulphinyl, sulphonyl, —NH, —N($C_{1-3}$-alkyl), —N(phenyl), —N($C_{1-3}$-alkyl-carbonyl) or —N(benzoyl) group, a $C_{4-7}$-cycloalkylamino, $C_{4-7}$-cycloalkyl-$C_{1-3}$-alkylamino or $C_{4-7}$-cycloalkenylamino group wherein position 1 of the ring is not involved in the double bond and wherein the abovementioned groups may each additionally be substituted at the amino-nitrogen atom by a $C_{5-7}$-cycloalkyl, $C_{2-4}$-alkenyl or $C_{1-4}$-alkyl group, a 4- to 7-membered cycloalkyleneimino group, wherein the cycloalkylene moiety may be fused to a phenyl group or to an oxazolo, imidazolo, thiazolo, pyridino, pyrazino or pyrimidino group optionally substituted by a fluorine, chlorine, bromine or iodine atom, by a nitro, $C_{1-3}$-alkyl, $C_{1-3}$-alkoxy or amino group, and/or one or two hydrogen atoms may each be replaced by a $C_{1-3}$-alkyl, $C_{5-7}$-cycloalkyl or phenyl group and/or the methylene group in the 3 position of a 5-membered cycloalkyleneimino group may be substituted by a hydroxy, hydroxy-$C_{1-3}$-alkyl, $C_{1-3}$-alkoxy or $C_{1-3}$-alkoxy-$C_{1-3}$-alkyl group, the methylene group in the 3 or 4 position of a 6- or 7-membered cycloalkyleneimino group may in each case be substituted by a hydroxy, hydroxy-$C_{1-3}$-alkyl, $C_{1-2}$-alkoxy, $C_{1-3}$-alkoxy-$C_{1-3}$-alkyl, carboxy, $C_{1-4}$-alkoxycarbonyl, aminocarbonyl, $C_{1-3}$-alkylaminocarbonyl, di-($C_{1-3}$-alkyl)-aminocarbonyl, phenyl-$C_{1-3}$-alkylamino or N—($C_{1-3}$-alkyl)-phenyl-$C_{1-3}$-alkyl-amino group or may be replaced by an oxygen or sulphur atom, by a sulphinyl, sulphonyl, —NH, —N($C_{1-3}$-alkyl-), —N(phenyl), —N(phenyl-$C_{1-3}$-alkyl-), —N($C_{1-3}$-alkyl-carbonyl-), —N($C_{1-4}$-alkyl-hydroxy-carbonyl-), —N($C_{1-4}$-alkoxy-carbonyl-), —N(benzoyl-) or —N(phenyl-$C_{1-3}$-alkyl-carbonyl-) group, wherein a methylene group linked to an imino-nitrogen atom of the cycloalkyleneimino group may be replaced by a carbonyl or sulphonyl group or in a 5- to 7-membered monocyclic cycloalkyleneimino group or a cycloalkyleneimino group fused to a phenyl group the two methylene groups linked to the imino-nitrogen atom may each be replaced by a carbonyl group, or $R_6$ denotes a $C_{1-4}$-alkyl group which is substituted by a carboxy, $C_{1-3}$-alkoxycarbonyl, aminocarbonyl, $C_{1-3}$-alkylaminocarbonyl or di-($C_{1-3}$-alkyl)-aminocarbonyl group or by a 4- to 7-membered cycloalkyleneiminocarbonyl group, an N—($C_{1-3}$-alkyl)-$C_{2-4}$-alkanoylamino group which is additionally substituted in the alkyl moiety by a carboxy or $C_{1-3}$-alkoxycarbonyl group, a group of formula

$$—N(R_{12})—CO—(CH_2)_p—R_{13} \quad (IV),$$

wherein $R_{12}$ denotes a hydrogen atom, a $C_{1-6}$-alkyl or $C_{3-7}$-cycloalkyl group or a $C_{1-3}$-alkyl group terminally substituted by a phenyl, heteroaryl, trifluoromethyl, hydroxy, $C_{1-3}$-alkoxy, aminocarbonyl, $C_{1-4}$-alkylamino-carbonyl, di-($C_{1-4}$-alkyl)-amino-carbonyl, $C_{1-3}$-alkyl-carbonyl, $C_{1-3}$-alkyl-sulphonylamino, N—($C_{1-3}$-alkyl)-$C_{1-3}$-alkyl-sulphonylamino, $C_{1-3}$-alkyl-aminosulphonyl or di-($C_{1-3}$-alkyl)-aminosulphonyl group and p denotes one of the numbers 0, 1, 2 or 3 and $R_{13}$ assumes the meanings of the abovementioned group $R_7$, or, if p denotes one of the numbers 1, 2 or 3, it may also denote a hydrogen atom, a group of formula

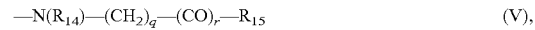

$$—N(R_{14})—(CH_2)_q—(CO)_r—R_{15} \quad (V),$$

wherein $R_{14}$ denotes a hydrogen atom, a $C_{1-4}$-alkyl group, a $C_{1-3}$-alkylcarbonyl, arylcarbonyl, phenyl-$C_{1-3}$-alkylcarbonyl, heteroarylcarbonyl, heteroaryl-$C_{1-3}$-alkylcarbonyl, $C_{1-4}$-alkylsulphonyl, arylsulphonyl, phenyl-$C_{1-3}$-alkylsulphonyl, heteroarylsulphonyl or heteroaryl-$C_{1-3}$-alkyl-sulphonyl group, q denotes one of the numbers 1, 2, 3 or 4, r denotes the number 1 or, if q is one of the numbers 2, 3 or 4, it may also denote the number 0 and $R_{15}$ assumes the meanings of the abovementioned group $R_7$, a group of formula

$$—N(R_{16})—SO_2—R_{17} \quad (VI),$$

wherein $R_{16}$ denotes a hydrogen atom or a $C_{1-4}$-alkyl group optionally terminally substituted by a cyano, trifluoromethyl-carbonylamino or N—($C_{1-3}$-alkyl)-trifluoromethyl-carbonyl-amino group and $R_{17}$ denotes a $C_{1-3}$-alkyl group, an amino group substituted by a di-($C_{1-3}$-alkyl)-amino-$C_{1-3}$-alkyl-carbonyl or di-($C_{1-3}$-alkyl)-amino-$C_{1-3}$-alkyl-sulphonyl group and a di-($C_{1-3}$-alkyl)-aminocarbonyl-$C_{1-3}$-alkyl group, or an N—($C_{1-3}$-alkyl)-$C_{1-5}$-alkylsulphonylamino or N—($C_{1-3}$-alkyl)-phenylsulphonylamino group wherein the alkyl moiety is additionally substituted by a cyano or carboxy group, wherein all the single-bonded or fused phenyl groups contained in the groups mentioned under $R_6$ may be mono- or disubstituted by fluorine, chlorine, bromine or iodine atoms, by $C_{1-5}$-alkyl, trifluoromethyl, hydroxy, $C_{1-3}$-alkoxy, carboxy, $C_{1-3}$-alkoxycarbonyl, aminocarbonyl, $C_{1-4}$-alkylamino-carbonyl, di-($C_{1-4}$-alkyl)-amino-carbonyl, aminosulphonyl, $C_{1-3}$-alkyl-aminosulphonyl, di-($C_{1-3}$-alkyl)-aminosulphonyl, $C_{1-3}$-alkyl-sulphonylamino, nitro or cyano groups, wherein the substituents may be identical or different, or two adjacent hydrogen atoms of the phenyl groups may be replaced by a methylenedioxy group, and $R_5$ denotes a hydrogen atom or a $C_{1-3}$-alkyl group, wherein by an aryl group is meant a phenyl or naphthyl group optionally mono- or disubstituted by a fluorine, chlorine, bromine or iodine atom, by a cyano, trifluoromethyl, nitro, carboxy, aminocarbonyl, $C_{1-3}$-alkyl or $C_{1-3}$-alkoxy group and by a heteroaryl group is meant a monocyclic 5- or 6-membered heteroaryl group optionally substituted by a $C_{1-3}$-alkyl group in the carbon skeleton, wherein the 6-membered heteroaryl group contains one, two or three nitrogen atoms and the 5-membered heteroaryl group contains an imino group optionally substituted by a $C_{1-3}$-alkyl or phenyl-$C_{1-3}$-alkyl group, an oxygen or sulphur atom or an imino group optionally substituted by a $C_{1-3}$-alkyl or phenyl-$C_{1-3}$-alkyl group or an oxygen or sulphur atom and additionally a nitrogen atom or an imino group optionally substituted by a $C_{1-3}$-alkyl or phenyl-$C_{1-3}$-alkyl group and two nitrogen atoms, and moreover a phenyl ring may be fused to the abovementioned monocyclic heterocyclic groups via two adjacent carbon atoms and the bonding takes place via a nitrogen atom or via a carbon atom of the heterocyclic moiety or a fused phenyl ring, some or all of the hydrogen atoms in the abovementioned alkyl and alkoxy groups or in the alkyl moieties contained in the above-defined groups of formula I optionally being replaced by fluorine atoms, the saturated alkyl and alkoxy moieties with more than 2 carbon atoms which are present in the groups defined hereinbefore also include the branched isomers thereof, such as for example the isopropyl, tert.butyl, isobutyl group, unless otherwise stated, and additionally the hydrogen atom of any carboxy group present or a hydrogen atom bound to a nitrogen atom, e.g. a hydrogen atom of an amino, alkylamino or imino group or a saturated N-heterocycle such as the piperidinyl group, may each be replaced by a group which can be cleaved in vivo.

By a group which can be cleaved in vivo from an imino or amino group is meant, for example, a hydroxy group, an acyl group such as the benzoyl or pyridinoyl group or a $C_{1-16}$-alkanoyl group such as the formyl, acetyl, propionyl, butanoyl, pentanoyl or hexanoyl group, an allyloxycarbonyl group, a $C_{1-16}$-alkoxycarbonyl group such as the methoxycarbonyl, ethoxycarbonyl, propoxycarbonyl, isopropoxycarbonyl, butoxycarbonyl, tert.butoxycarbonyl, pentoxycarbonyl, hexyloxycarbonyl, octyloxycarbonyl, nonyloxycarbonyl, decyloxycarbonyl, undecyloxycarbonyl, dodecyloxycarbonyl or hexadecyloxycarbonyl group, a phenyl-$C_{1-6}$-alkoxycarbonyl group such as the benzyloxycarbonyl, phenylethoxycarbonyl or phenylpropoxycarbonyl group, a $C_{1-3}$-alkylsulphonyl-$C_{2-4}$-alkoxycarbonyl, $C_{1-3}$-alkoxy-$C_{2-4}$-alkoxy-$C_{2-4}$-alkoxycarbonyl or $R_eCO$—$O$—$(R_fCR_g)$—$O$—$CO$ group wherein $R_e$ denotes a $C_{1-8}$-alkyl, $C_{5-7}$-cycloalkyl, phenyl or phenyl-$C_{1-3}$-alkyl group, $R_f$ denotes a hydrogen atom, a $C_{1-3}$-alkyl, $C_{5-7}$-cycloalkyl or phenyl group and $R_g$ denotes a $C_{1-3}$-alkyl or $R_eCO$—$O$—$(R_fCR_g)$—$O$ group wherein $R_e$ to $R_g$ are as hereinbefore defined, wherein additionally the amino group may be a phthalimido group, whilst the abovementioned ester groups may also be used as a group which can be converted in vivo into a carboxy group.

One sub-group of compounds of general formula I which deserves special mention comprises those wherein X, $R_1$ and $R_3$ to $R_5$ are as hereinbefore defined and $R_2$ denotes a straight-chain or branched $C_{1-6}$-alkoxy-carbonyl group, a $C_{4-7}$-cycloalkoxycarbonyl or a aryloxycarbonyl group, a straight-chain or branched $C_{1-6}$-alkoxy-carbonyl group, which is terminally substituted in the alkyl moiety by a phenyl, heteroaryl, carboxy, $C_{1-3}$-alkoxycarbonyl, aminocarbonyl, $C_{1-3}$-alkylaminocarbonyl or di-($C_{1-3}$-alkyl)-aminocarbonyl group, a straight-chain or branched $C_{2-6}$-alkoxy-carbonyl group, which is terminally substituted in the alkyl moiety by a chlorine atom or a hydroxy, $C_{1-3}$-alkoxy, amino, $C_{1-3}$-alkylamino or di-($C_{1-3}$-alkyl)-amino group, the tautomers, the diastereomers, the enantiomers, the mixtures thereof and the salts thereof.

A second sub-group of compounds of general formula I which deserves special mention comprises those wherein X, $R_1$ and $R_3$ to $R_5$ are as hereinbefore defined and $R_2$ denotes an aminocarbonyl or methylaminocarbonyl group, an ethylaminocarbonyl group optionally substituted in the 2 position of the ethyl group by a hydroxy or $C_{1-3}$-alkoxy group or a di-($C_{1-2}$-alkyl)-aminocarbonyl group, the tautomers, the diastereomers, the enantiomers, the mixtures thereof and the salts thereof.

A third sub-group of compounds of general formula I which deserves special mention comprises those wherein X, $R_1$ to $R_3$ and $R_5$ are as hereinbefore defined and $R_4$ denotes an $R_7$—($C_{1-4}$-alkyl)-phenyl group, wherein $R_7$ denotes an amino, $C_1$-alkylamino, di-($C_{1-7}$-alkyl)-amino, phenylamino, N-phenyl-$C_{1-3}$-alkyl-amino, phenyl-$C_{1-3}$-alkylamino, N—($C_{1-3}$-alkyl)-phenyl-$C_{1-3}$-alkylamino or di-(phenyl-$C_{1-3}$-alkyl)-amino group, or a phenyl group substituted by the group of formula

$$—N(R_{12})—CO—(CH_2)_p—R_{13} \quad (IV),$$

wherein $R_{12}$, p and $R_{13}$ are as hereinbefore defined, the tautomers, the diastereomers, the enantiomers, the mixtures thereof and the salts thereof.

Preferred compounds of general formula I are those wherein $R_1$ and $R_3$ are as hereinbefore defined and X denotes an oxygen atom, $R_2$ denotes a carboxy group, a straight-chain or branched $C_{1-6}$-alkoxy-carbonyl group, a $C_{5-7}$-cycloalkoxycarbonyl or a phenoxycarbonyl group, a straight-chain or branched $C_{1-3}$-alkoxy-carbonyl group, which is terminally substituted in the alkyl moiety by a phenyl, heteroaryl, carboxy, $C_{1-3}$-alkoxycarbonyl, aminocarbonyl, $C_{1-3}$-alkylaminocarbonyl or di-($C_{1-3}$-alkyl)-aminocarbonyl group, a straight-chain or branched $C_{2-3}$-alkoxy-carbonyl group, which is terminally substituted in the alkyl moiety by a chlorine atom, by a hydroxy, $C_{1-3}$-alkoxy, amino, $C_{1-3}$-alkylamino or di-($C_{1-3}$-alkyl)-amino group, an aminocarbonyl or methylaminocarbonyl group, an ethylaminocarbonyl group optionally substituted in the 2 position of the ethyl group by a hydroxy or $C_{1-3}$-alkoxy group or a di-($C_{1-2}$-alkyl)-aminocarbonyl group, $R_4$ denotes a $C_{3-7}$-cycloalkyl group, whilst the methylene group in the 4 position of a 6- or 7-membered cycloalkyl group may be substituted by an amino, $C_{1-3}$-alkylamino or di-($C_{1-3}$-alkyl)-amino group or replaced by an —NH or —N($C_{1-3}$-alkyl) group, or a phenyl group substituted by the group $R_6$, which may additionally be mono- or disubstituted by fluorine, chlorine or bromine atoms, by $C_{1-3}$-alkyl, trifluoromethyl, hydroxy, $C_{1-3}$-alkoxy, carboxy, $C_{1-3}$-alkoxycarbonyl, amino, acetylamino, aminocarbonyl, $C_{1-3}$-alkyl-aminocarbonyl, di-($C_{1-3}$-alkyl)-aminocarbonyl, nitro or cyano groups, wherein the substituents may be identical or different and wherein $R_6$ denotes a hydrogen, fluorine, chlorine, bromine or iodine atom, a cyano, nitro, amino, $C_{1-5}$-alkyl, $C_{3-7}$-cycloalkyl, trifluoromethyl, phenyl, tetrazolyl or heteroaryl group, the group of formula

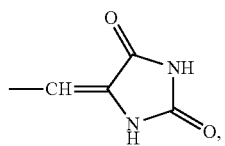

wherein a hydrogen atom bound to the nitrogen atom may be replaced by a $C_{1-3}$-alkyl group, a $C_{1-3}$-alkoxy group, an amino-$C_{2-3}$-alkoxy, $C_{1-3}$-alkylamino-$C_{2-3}$-alkoxy, di-($C_{1-3}$-alkyl)-amino-$C_{2-3}$-alkoxy, phenyl-$C_{1-3}$-alkylamino-$C_{2-3}$-alkoxy, N—($C_{1-3}$-alkyl)-phenyl-$C_{1-3}$-alkylamino-$C_{2-3}$-alkoxy, pyrrolidino-$C_{2-3}$-alkoxy, piperidino-$C_{2-3}$-alkoxy or $C_{1-3}$-alkylmercapto group, a carboxy, $C_{1-4}$-alkoxycarbonyl, aminocarbonyl, $C_{1-3}$-alkylamino-carbonyl, phenyl-$C_{1-3}$-alkylamino-carbonyl or N—($C_{1-3}$-alkyl)-phenyl-$C_{1-3}$-alkylamino-carbonyl group, a $C_{3-7}$-cycloalkyl-carbonyl group, wherein the methylene group in the 4 position of the 6- or 7-membered cycloalkyl moiety may be replaced by an —NH or —N($C_{1-3}$-alkyl) group, a 4- to 7-membered cycloalkyleneimino group, wherein a methylene group linked to the imino group may be replaced by a carbonyl or sulphonyl group or one or two hydrogen atoms may each be replaced by a $C_{1-3}$-alkyl group and/or in each case the methylene group in the 4 position of a 6- or 7-membered cycloalkyleneimino group may be substituted by a carboxy, $C_{1-3}$-alkoxycarbonyl, aminocarbonyl, $C_{1-3}$-alkylaminocarbonyl, di-($C_{1-3}$-alkyl)-aminocarbonyl, phenyl-$C_{1-3}$-alkylamino or N—($C_{1-3}$-alkyl)-phenyl-$C_{1-3}$-alkylamino group or may be replaced by an oxygen or sulphur atom, by a sulphinyl, sulphonyl, —NH or —N($C_{1-3}$-alkyl) group, a $C_{1-4}$-alkyl group terminally substituted by the group $R_7$, wherein $R_7$ denotes a $C_{5-7}$-cycloalkyl group, whilst the methylene group in the 4 position of a 6- or 7-membered cycloalkyl group may be replaced by an —NH or —N($C_{1-3}$-alkyl) group or in a 5- to 7-membered cycloalkyl group a —(CH$_2$)$_2$ group may be replaced by a —CO—NH group, a —(CH$_2$)$_3$ group may be replaced by a —NH—CO—NH— or a —(CH$_2$)$_4$ group may be replaced by a —NH—CO—NH—CO group, whilst in each case a hydrogen atom bound to a nitrogen atom may be replaced by a $C_{1-3}$-alkyl group, a phenyl or heteroaryl group, a hydroxy or $C_{1-3}$-alkoxy group, an amino, $C_{1-6}$-alkylamino, di-($C_{1-6}$-alkyl)-amino, phenylamino, N-phenyl-$C_{1-3}$-alkyl-amino, phenyl-$C_{1-3}$-alkylamino, N—($C_{1-3}$-alkyl)-phenyl-$C_{1-3}$-alkylamino or di-(phenyl-$C_{1-3}$-alkyl)-amino group, a ω-hydroxy-$C_{2-3}$-alkyl-amino, N—($C_{1-3}$-alkyl)-ω-hydroxy-$C_{2-3}$-alkyl-amino, di-(ω-hydroxy-$C_{2-3}$-alkyl)-amino, di-(ω-($C_{1-3}$-alkoxy)-$C_{2-3}$-alkyl)-amino or N-(di-oxolan-2-yl)-$C_{1-3}$-alkyl-amino group, a $C_{1-3}$-alkylcarbonylamino-$C_{2-3}$-alkyl-amino or $C_{1-3}$-alkylcarbonylamino-$C_{2-3}$-alkyl-N—($C_{1-3}$-alkyl)-amino group, a $C_{1-3}$-alkylsulphonylamino, N—($C_{1-3}$-alkyl)-$C_{1-3}$-alkylsulphonylamino, $C_{1-3}$-alkylsulphonylamino-$C_{2-3}$-alkyl-amino or $C_{1-3}$-alkylsulphonylamino-$C_{2-3}$-alkyl-N—($C_{1-3}$-alkyl)-amino group, a hydroxycarbonyl-$C_{1-3}$-alkylamino or N—($C_{1-3}$-alkyl)-hydroxycarbonyl-$C_{1-3}$-alkyl-amino group a guanidino group wherein a hydrogen atom may be replaced by a $C_{1-3}$-alkyl group, a group of formula $$-N(R_8)-CO-(CH_2)_n-R_9 \qquad (II),$$

wherein $R_8$ denotes a hydrogen atom or a $C_{1-3}$-alkyl group, n denotes one of the numbers 0, 1, 2 or 3 and $R_9$ denotes an amino, $C_{1-3}$-alkylamino, di-($C_{1-3}$-alkyl)-amino, phenylamino, benzylamino or $C_{1-4}$-alkoxy group, a 5- to 7-membered cycloalkyleneimino group, wherein the methylene group in position 4 of the piperidino group may be replaced by an oxygen or sulphur atom, by an —NH, —N($C_{1-3}$-alkyl), —N(phenyl), —N($C_{1-3}$-alkylcarbonyl) or —N(benzoyl) group, or, if n denotes one of the numbers 1, 2 or 3, it may also denote a hydrogen atom, a group of formula $$-N(R_{10})-(CH_2)_m-(CO)_o-R_{11} \qquad (III),$$

wherein $R_{10}$ denotes a hydrogen atom, a $C_{1-3}$-alkyl group, a $C_{1-3}$-alkylcarbonyl or $C_{1-3}$-alkylsulphonyl group, m denotes one of the numbers 1, 2 or 3, o denotes the number 1 or, if m is one of the numbers 2 or 3, o may also denote the number 0 and $R_{11}$ denotes an amino, $C_{1-3}$-alkylamino, di-($C_{1-3}$-alkyl)-amino, $C_{1-4}$-alkoxy or $C_{1-3}$-alkoxy-$C_{1-3}$-alkoxy group or a 5- to 7-membered cycloalkyleneimino group, wherein the methylene group in position 4 of the piperidino group may be replaced by an oxygen or sulphur atom, by an —NH, —N($C_{1-3}$-alkyl), —N(phenyl), —N($C_{1-3}$-alkylcarbonyl) or —N(benzoyl) group, a $C_{4-7}$-cycloalkylamino or $C_{4-7}$-cycloalkenylamino group wherein position 1 of the ring is not involved in the double bond, a 4- to 7-membered cycloalkyleneimino group, wherein the cycloalkylene moiety may be fused to a phenyl group or one or two hydrogen atoms may each be replaced by a $C_{1-3}$-alkyl group and/or the methylene group in position 3 of the pyrrolidino group may be substituted by a hydroxy or $C_{1-3}$-alkoxy group, in each case the methylene group in the 4 position of a 6- or 7-membered cycloalkyleneimino group may be substituted by a hydroxy, hydroxy-$C_{1-3}$-alkyl, $C_{1-3}$-alkoxy, carboxy, $C_{1-3}$-alkoxycarbonyl, aminocarbonyl, $C_{1-3}$-alkylaminocarbonyl, di-($C_{1-3}$-alkyl)-aminocarbonyl, phenyl-$C_{1-3}$-alkylamino or N—($C_{1-3}$-alkyl)-phenyl-$C_{1-3}$-alkylamino group or may be replaced by an oxygen or sulphur atom, by a sulphinyl, sulphonyl, —NH, —N($C_{1-3}$-alkyl), —N(phenyl), —N(phenyl-$C_{1-3}$-alkyl), —N($C_{1-3}$-alkyl-carbonyl), —N($C_{1-4}$-alkoxy-carbonyl), —N(benzoyl) or —N(phenyl-$C_{1-3}$-alkyl-carbonyl) group, wherein a methylene group linked to an imino-nitrogen atom of the cycloalkyleneimino group may be replaced by a carbonyl or sulphonyl group or in a 5- to 6-membered monocyclic cycloalkyleneimino group or a cycloalkyleneimino group fused to a phenyl group the two methylene groups linked to the imino-nitrogen atom may each be replaced by a carbonyl group, or $R_6$ denotes a $C_{1-4}$-alkyl group which is terminally substituted by a carboxy, $C_{1-3}$-alkoxycarbonyl, aminocarbonyl, $C_{1-3}$-alkylaminocarbonyl or di-($C_{1-3}$-alkyl)-aminocarbonyl group or by a 4- to 7-membered cycloalkyleneiminocarbonyl group, a group of formula $$-N(R_{12})-CO-(CH_2)_p-R_{13} \qquad (IV),$$

wherein $R_{12}$ denotes a hydrogen atom, a $C_{1-3}$-alkyl, $C_{5-7}$-cycloalkyl, phenyl-$C_{1-3}$-alkyl or heteroaryl-$C_{1-3}$-alkyl group and p denotes one of the numbers 0, 1, 2 or 3 and $R_{13}$ assumes the meanings of the abovementioned group $R_7$, or, if p denotes one of the numbers 1, 2 or 3, it may also denote a hydrogen atom, a group of formula

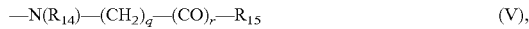

$$-N(R_{14})-(CH_2)_q-(CO)_r-R_{15} \qquad (V),$$

wherein $R_{14}$ denotes a hydrogen atom, a $C_{1-4}$-alkyl group, a $C_{1-3}$-alkylcarbonyl, phenylcarbonyl, phenyl-$C_{1-3}$-alkylcarbonyl, heteroarylcarbonyl, heteroaryl-$C_{1-3}$-alkylcarbonyl, $C_{1-4}$-alkylsulphonyl, phenylsulphonyl, phenyl-$C_{1-3}$-alkylsulphonyl-heteroarylsulphonyl or heteroaryl-$C_{1-3}$-alkylsulphonyl group, q denotes one of the numbers 1, 2, 3 or 4, r denotes the number 1 or, if q is one of the numbers 2, 3 or 4, it may also denote the number 0 and $R_{15}$ assumes the meanings of the abovementioned group $R_7$, a group of formula

$$-N(R_{16})-SO_2-R_{17} \qquad (VI),$$

wherein $R_{16}$ denotes a hydrogen atom or a $C_{1-4}$-alkyl group optionally terminally substituted by a cyano, trifluoromethylcarbonylamino or N—($C_{1-3}$-alkyl)-trifluoromethyl-carbonyl-amino group and $R_{17}$ denotes a $C_{1-3}$-alkyl group, an amino group substituted by a di-($C_{1-3}$-alkyl)-amino-$C_{1-3}$-alkyl-carbonyl or di-($C_{1-3}$-alkyl)-amino-$C_{1-3}$-alkyl-sulphonyl group and a di-($C_{1-3}$-alkyl)-aminocarbonyl-$C_{1-3}$-alkyl group, wherein all the single-bonded or fused phenyl groups contained in the groups mentioned under $R_6$ may be mono- or disubstituted by fluorine, chlorine or bromine atoms, by $C_{1-3}$-alkyl, trifluoromethyl, hydroxy, $C_{1-3}$-alkoxy, carboxy, $C_{1-3}$-alkoxycarbonyl, aminocarbonyl, $C_{1-3}$-alkyl-aminocarbonyl, aminosulphonyl, $C_{1-3}$-alkyl-aminosulphonyl, nitro or cyano groups, wherein the substituents may be identical or different, or two adjacent hydrogen atoms of the phenyl groups may be replaced by a methylenedioxy group, and $R_5$ denotes a hydrogen atom or a $C_{1-3}$-alkyl group, whilst by a heteroaryl group as mentioned above is meant a pyridinyl, pyrazinyl, pyrimidinyl, pyridazinyl, pyrrolyl, furyl, thienyl, oxazolyl, thiazolyl, pyrazolyl, imidazolyl or triazolyl group optionally substituted in the carbon skeleton by a $C_{1-3}$-alkyl group wherein a hydrogen atom bound to a nitrogen atom may be replaced by a $C_{1-3}$-alkyl or phenyl-$C_{1-3}$-alkyl group and wherein the 5-membered heteroaryl groups containing at least one imino group are bound via a carbon or nitrogen atom, a hydrogen atom bound to a nitrogen atom in the abovementioned groups may be replaced by a group which can be cleaved in vivo, particularly by an acetyl or tert.butoxycarbonyl group, the carboxy groups contained in the abovementioned groups may each be substituted by a group which can be cleaved in vivo and may occur, for example, in the form of the tert.butoxycarbonyl group, some or all of the hydrogen atoms in the abovementioned alkyl and alkoxy groups or in the alkyl moieties contained in the above-defined groups of formula I optionally being replaced by fluorine atoms and the saturated alkyl and alkoxy moieties contained in the abovementioned groups, which contain more than 2 carbon atoms, may be straight-chain or branched, unless otherwise stated, the tautomers, the diastereomers, the enantiomers, the mixtures thereof and the salts thereof.

One subgroup of preferred compounds of general formula I deserving special mention comprises those wherein X, $R_1$ and $R_3$ to $R_5$ are as hereinbefore defined and $R_2$ denotes a straight-chain or branched $C_{1-6}$-alkoxy-carbonyl group, a $C_{5-7}$-cycloalkoxycarbonyl or a phenoxycarbonyl group, a straight-chain or branched $C_{1-3}$-alkoxy-carbonyl group, which is terminally substituted in the alkyl moiety by a phenyl-carboxy, $C_{1-3}$-alkoxycarbonyl, aminocarbonyl, $C_{1-3}$-alkylaminocarbonyl or di-($C_{1-3}$-alkyl)-aminocarbonyl group, a straight-chain or branched $C_{2-3}$-alkoxy-carbonyl group, which is terminally substituted in the alkyl moiety by a hydroxy, $C_{1-3}$-alkoxy, amino, $C_{1-3}$-alkylamino or di-($C_{1-3}$-alkyl)-amino group, the tautomers, the diastereomers, the enantiomers, the mixtures thereof and the salts thereof.

A second sub-group of preferred compounds of general formula I deserving special mention comprises those wherein X, $R_1$ and $R_3$ to $R_5$ are as hereinbefore defined and $R_2$ denotes an aminocarbonyl or methylaminocarbonyl group, an ethylaminocarbonyl group optionally substituted in the 2 position of the ethyl group by a hydroxy or $C_{1-3}$-alkoxy group or a di-($C_{1-2}$-alkyl)-aminocarbonyl group, the tautomers, the diastereomers, the enantiomers, the mixtures thereof and the salts thereof.

A third sub-group of preferred compounds of general formula I deserving special mention comprises those wherein X, $R_1$ to $R_3$ and $R_5$ are as hereinbefore defined and $R_4$ denotes an $R_7$-(n-$C_{1-4}$-alkyl)-phenyl group, wherein $R_7$ denotes an amino, $C_{1-6}$-alkylamino, di-($C_{1-6}$-alkyl)-amino, phenylamino, N-phenyl-$C_{1-3}$-alkyl-amino, phenyl-$C_{1-3}$-alkylamino, N—($C_{1-3}$-alkyl)-phenyl-$C_{1-3}$-alkylamino or di-(phenyl-$C_{1-3}$-alkyl)-amino group, or a phenyl group substituted by the group of formula

$$-N(R_{12})-CO-(CH_2)_p-R_{13} \qquad (IV),$$

wherein $R_{12}$, p and $R_{13}$ are as hereinbefore defined, the tautomers, the diastereomers, the enantiomers, the mixtures thereof and the salts thereof.

Particularly preferred compounds of general formula I are those wherein

X denotes an oxygen atom, $R_1$ denotes a hydrogen atom, $R_2$ denotes a carboxy group, a straight-chain or branched $C_{1-4}$-alkoxycarbonyl group or a phenoxycarbonyl group, a straight-chain or branched $C_{1-3}$-alkoxy-carbonyl group, which is terminally substituted in the alkyl moiety by a phenyl, carboxy, $C_{1-3}$-alkoxycarbonyl, aminocarbonyl, $C_{1-3}$-alkylaminocarbonyl or di-($C_{1-3}$-alkyl)-aminocarbonyl group, a straight-chain or branched $C_{2-3}$-alkoxy-carbonyl group which is terminally substituted in the alkyl moiety by a hydroxy, $C_{1-3}$-alkoxy, amino, $C_{1-3}$-alkylamino or di-($C_{1-3}$-alkyl)-amino group, an aminocarbonyl or methylaminocarbonyl group, an ethylaminocarbonyl group optionally substituted in the 2 position of the ethyl group by a hydroxy or $C_{1-3}$-alkoxy group or a di-($C_{1-2}$-alkyl)-aminocarbonyl group, $R_3$ denotes a $C_{1-4}$-alkyl group or a phenyl group which may be substituted by a fluorine, chlorine or bromine atom, by a trifluoromethyl, $C_{1-3}$-alkyl, hydroxy or $C_{1-3}$-alkoxy group, $R_4$ denotes a $C_{1-6}$-cycloalkyl group, wherein the methylene group in position 4 of the cyclohexyl group may be substituted by an amino, $C_{1-3}$-alkylamino or di-($C_{1-3}$-alkyl)-amino group or replaced by an —NH or —N($C_{1-3}$-alkyl) group, a phenyl group, a phenyl group disubstituted by $C_{1-3}$-alkyl, $C_{1-3}$-alkoxy or nitro groups, wherein the substituents may be identical or different, or a phenyl group substituted by the group $R_6$, which may additionally be substituted by a fluorine, chlorine or bromine atom or by an amino or nitro group, wherein $R_6$ denotes a fluorine, chlorine or bromine atom, a $C_{1-3}$-alkyl, $C_{1-3}$-alkoxy, nitro, amino or $C_{5-6}$-cycloalkyl group, a pyrrolyl, pyrazolyl, imidazolyl, triazolyl or tetrazolyl group bound via a carbon atom, wherein the abovementioned heteroaromatic groups in the carbon skeleton may be substituted by a $C_{1-3}$-alkyl group or a hydrogen atom bound to a nitrogen atom may be replaced by a $C_{1-3}$-alkyl or phenyl-$C_{1-3}$-alkyl group, the group of formula

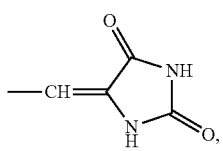

a carboxy, $C_{1-4}$-alkoxycarbonyl, phenyl-$C_{1-3}$-alkylaminocarbonyl or $C_{5-7}$-cycloalkyl-carbonyl group, a 5 or 6-membered cycloalkyleneimino group, wherein the methylene group in position 4 of the piperidino group may be replaced by an oxygen or sulphur atom, by an —NH or —N($C_{1-3}$-alkyl) group, an unbranched $C_{1-3}$-alkyl group terminally substituted by the group $R_7$, wherein $R_7$ denotes a $C_{5-7}$-cycloalkyl group, wherein in a 5 or 6-membered cycloalkyl group a —(CH$_2$)$_2$— group may be replaced by a —CO—NH group, a —(CH$_2$)$_3$— group may be replaced by an —NH—CO—NH— or a —(CH$_2$)$_4$— group may be replaced by an —NH—CO—NH—CO group, whilst in each case a hydrogen atom bound to a nitrogen atom may be replaced by a $C_{1-3}$-alkyl group, a phenyl or pyridinyl group or a pyrrolyl, pyrazolyl, imidazolyl or triazolyl group bound via a carbon or nitrogen atom, wherein the abovementioned heteroaromatic groups in the carbon skeleton may be substituted by a $C_{1-3}$-alkyl group or a hydrogen atom bound to a nitrogen atom may be replaced by a $C_{1-3}$-alkyl group, a hydroxy or $C_{1-3}$-alkoxy group, an amino, $C_{1-6}$-alkylamino, di-($C_{1-6}$-alkyl)-amino, phenylamino, N-phenyl-$C_{1-3}$-alkylamino, phenyl-$C_{1-3}$-alkylamino or N—($C_{1-3}$-alkyl)-phenyl-$C_{1-3}$-alkylamino group, a ω-hydroxy-$C_{2-3}$-alkyl-amino, N—($C_{1-3}$-alkyl)-ω-hydroxy-$C_{2-3}$-alkyl-amino, di-(ω-hydroxy-$C_{2-3}$-alkyl)-amino or di-(ω-($C_{1-3}$-alkoxy)-$C_{2-3}$-alkyl)-amino group, a $C_{1-3}$-alkylcarbonylamino-$C_{2-3}$-alkyl-amino or $C_{1-3}$-alkylcarbonylamino-$C_{2-3}$-alkyl-N—($C_{1-3}$-alkyl)-amino group, a $C_{1-3}$-alkylsulphonylamino, N—($C_{1-3}$-alkyl)-$C_{1-3}$-alkylsulphonylamino, $C_{1-3}$-alkylsulphonylamino-$C_{2-3}$-alkylamino or $C_{1-3}$-alkylsulphonylamino-$C_{2-3}$-alkyl-N—($C_{1-3}$-alkyl)-amino group, a hydroxycarbonyl-$C_{1-3}$-alkylamino or N—($C_{1-3}$-alkyl)-hydroxycarbonyl-$C_{1-3}$-alkyl-amino group, a guanidino group wherein a hydrogen atom may be replaced by a $C_{1-3}$-alkyl group, a group of formula $$—N(R_8)—CO—(CH_2)_n—R_9 \qquad (II),$$

wherein $R_8$ denotes a hydrogen atom or a $C_{1-3}$-alkyl group, n denotes one of the numbers 0, 1, 2 or 3 and $R_9$ denotes an amino, $C_{1-3}$-alkylamino, di-($C_{1-3}$-alkyl)-amino or $C_{1-4}$-alkoxy group, a 5- or 6-membered cycloalkyleneimino group, wherein the methylene group in position 4 of the piperidino group may be replaced by an —NH, —N($C_{1-3}$-alkyl) or —N($C_{1-3}$-alkyl-carbonyl) group, or, if n denotes one of the numbers 1, 2 or 3, $R_9$ may also denote a hydrogen atom, a group of formula $$—N(R_{10})—(CH_2)_m—(CO)_o—R_{11} \qquad (III),$$

wherein $R_{10}$ denotes a hydrogen atom or a $C_{1-3}$-alkyl group, m denotes one of the numbers 1, 2 or 3, o denotes the number 1 or, if m is one of the numbers 2 or 3, o may also denote the number 0 and $R_{11}$ denotes an amino, $C_{1-3}$-alkylamino, di-($C_{1-3}$-alkyl)-amino, $C_{1-4}$-alkoxy or methoxy-$C_{1-3}$-alkoxy group or a 5- or 6-membered cycloalkyleneimino group, wherein the methylene group in position 4 of the piperidino group may be replaced by an —NH, —N($C_{1-3}$-alkyl) or —N($C_{1-3}$-alkyl-carbonyl) group, an azetidino, pyrrolidino, piperidino, 2,6-dimethyl-piperidino, 3,5-dimethyl-piperidino or azepino group, wherein the methylene group in position 3 of the pyrrolidino group may be substituted by a hydroxy group, the methylene group in position 4 of the piperidino group may be substituted by a hydroxy, hydroxy-$C_{1-3}$-alkyl or $C_{1-3}$-alkoxy group or may be replaced by an oxygen or sulphur atom, by a sulphinyl, sulphonyl, —NH, —N($C_{1-3}$-alkyl), —N($C_{1-3}$-alkyl-carbonyl), —N(benzoyl) or —N(phenyl-$C_{1-3}$-alkyl-carbonyl) group, wherein a methylene group linked to an imino-nitrogen atom of the pyrrolidino, piperidino or piperazino group may be replaced by a carbonyl group, or $R_6$ denotes a straight-chain $C_{1-3}$-alkyl group which is terminally substituted by a carboxy or $C_{1-3}$-alkoxy-carbonyl group, a group of formula $$—N(R_{12})—CO—(CH_2)_p—R_{13} \qquad (IV),$$

wherein $R_{12}$ denotes a hydrogen atom, a $C_{1-3}$-alkyl or phenyl-$C_{1-3}$-alkyl group, p denotes one of the numbers 0, 1 or 2 and $R_{13}$ denotes an amino, $C_{1-4}$-alkylamino, di-($C_{1-4}$-alkyl)-amino, benzylamino, N—($C_{1-3}$-alkyl)-benzylamino, $C_{1-3}$-alkoxy-$C_{1-3}$-alkylamino, N—($C_{1-3}$-alkyl)-$C_{1-3}$-alkoxy-$C_{1-3}$-alkylamino, di-(2-methoxy-ethyl)-amino, di-(ω-hydroxy-$C_{2-3}$-alkyl)-amino or aminocarbonyl-methyl-N-(methyl)-amino group, a pyrrolyl, pyrazolyl or imidazolyl group bound via a nitrogen atom and optionally substituted by a $C_{1-3}$-alkyl group, a pyrrolidino, piperidino, morpholino, thiomorpholino or a piperazino group optionally substituted in the 4 position by a $C_{1-3}$-alkyl, phenyl-$C_{1-3}$-alkyl, $C_{1-3}$-alkylcarbonyl or $C_{1-4}$-alkoxycarbonyl group or, if n denotes the number 1 or 2, it may also denote a hydrogen atom, a group of formula

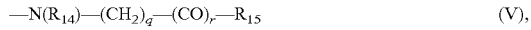

$$-N(R_{14})-(CH_2)_q-(CO)_r-R_{15} \quad (V),$$

wherein
$R_{14}$ denotes a hydrogen atom, a $C_{1-4}$-alkyl, $C_{1-3}$-alkyl-carbonyl, phenylcarbonyl, phenyl-$C_{1-3}$-alkylcarbonyl, furyl-carbonyl, pyridinyl-carbonyl, furyl-$C_{1-3}$-alkylcarbonyl, pyridinyl-$C_{1-3}$-alkylcarbonyl, $C_{1-4}$-alkylsulphonyl, phenylsulphonyl or phenyl-$C_{1-3}$-alkylsulphonyl group,
q denotes one of the numbers 1, 2 or 3,
r denotes the number 1 or, if q is one of the numbers 2 or 3, it may also denote the number 0 and
$R_{15}$ denotes an amino, $C_{1-4}$-alkylamino, di-($C_{1-4}$-alkyl)-amino, phenylamino, N—($C_{1-4}$-alkyl)-phenylamino, benzylamino or N—($C_{1-4}$-alkyl)-benzylamino group, or a group of formula

$$-N(R_{16})-SO_2-R_{17} \quad (VI),$$

wherein
$R_{16}$ denotes a hydrogen atom or a $C_{1-3}$-alkyl group optionally terminally substituted by a cyano, trifluoromethylcarbonylamino or N—($C_{1-3}$-alkyl)-trifluoromethyl-carbonyl-amino group and
$R_{17}$ denotes a $C_{1-3}$-alkyl group,
wherein all the single-bonded or fused phenyl groups contained in the groups mentioned under $R_6$ may be substituted by a fluorine, chlorine or bromine atom, by a methyl, trifluoromethyl, methoxy, nitro or cyano group and
$R_5$ denotes a hydrogen atom,
wherein a hydrogen atom bound to a nitrogen atom in the abovementioned groups may be replaced by an acetyl or tert.butoxycarbonyl group,
the carboxy groups contained in the abovementioned groups may also be present in the form of the tert.butoxycarbonyl precursor group and
the saturated alkyl and alkoxy moieties contained in the abovementioned groups, which contain more than 2 carbon atoms, may be straight-chain or branched, unless otherwise stated,
the tautomers, the diastereomers, the enantiomers, the mixtures thereof and the salts thereof.

One subgroup of particularly preferred compounds of general formula I deserving special mention comprises those wherein
X, $R_1$, $R_3$ and $R_5$ are as hereinbefore defined,
$R_2$ denotes a straight-chain or branched $C_{1-4}$-alkoxycarbonyl group or a phenoxycarbonyl group,
a straight-chain or branched $C_{1-3}$-alkoxycarbonyl group, which is terminally substituted in the alkyl moiety by a phenyl-carboxy, $C_{1-3}$-alkoxycarbonyl, aminocarbonyl, $C_{1-3}$-alkylaminocarbonyl or di-($C_{1-3}$-alkyl)-aminocarbonyl group, or
a straight-chain or branched $C_{2-3}$-alkoxy-carbonyl group, which is terminally substituted in the alkyl moiety by a hydroxy, $C_{1-3}$-alkoxy, amino, $C_{1-3}$-alkylamino or di-($C_{1-3}$-alkyl)-amino group, and
$R_4$ denotes an $R_7$-(n-$C_{1-3}$-alkyl)-phenyl group, wherein
$R_7$ denotes an amino, $C_{1-6}$-alkylamino, di-($C_{1-4}$-alkyl)-amino, ω-hydroxy-$C_{2-3}$-alkyl-amino, N—($C_{1-3}$-alkyl)-ω-hydroxy-$C_{2-3}$-alkyl-amino, di-(ω-hydroxy-$C_{2-3}$-alkyl)-amino or di-(ω-($C_{1-3}$-alkoxy)-$C_{2-3}$-alkyl)-amino group, or a phenyl group substituted by the group of formula

$$-N(R_{12})-CO-(CH_2)_p-R_{13} \quad (IV),$$

wherein $R_{12}$, p and $R_{13}$ are as hereinbefore defined,
the tautomers, the diastereomers, the enantiomers, the mixtures thereof and the salts thereof.

A second subgroup of particularly preferred compounds of general formula I deserving special mention comprises those wherein
X, $R_1$, $R_3$ and $R_5$ are as hereinbefore defined,
$R_2$ denotes an aminocarbonyl or methylaminocarbonyl group, an ethylaminocarbonyl group optionally substituted in the 2 position of the ethyl group by a hydroxy or $C_{1-3}$-alkoxy group or a di-($C_{1-2}$-alkyl)-aminocarbonyl group and
$R_4$ denotes a $R_7$-(n-$C_{1-3}$-alkyl)-phenyl group, wherein
$R_7$ denotes an amino, $C_{1-6}$-alkylamino, di-($C_{1-4}$-alkyl)-amino, ω-hydroxy-$C_{2-3}$-alkyl-amino, N—($C_{1-3}$-alkyl)-ω-hydroxy-$C_{2-3}$-alkyl-amino, di-(ω-hydroxy-$C_{2-3}$-alkyl)-amino or di-(ω-($C_{1-3}$-alkoxy)-$C_{2-3}$-alkyl)-amino group,
or a phenyl group substituted by the group of formula

$$-N(R_{12})-CO-(CH_2)_p-R_{13} \quad (IV),$$

wherein $R_{12}$, p and $R_{13}$ are as hereinbefore defined,
the tautomers, the diastereomers, the enantiomers, the mixtures thereof and the salts thereof.

Most particularly preferred compounds of general formula I are those wherein
X denotes an oxygen atom,
$R_1$ and $R_5$ each denote a hydrogen atom,
$R_2$ denotes a methoxycarbonyl, ethoxycarbonyl or aminocarbonyl group,
$R_3$ denotes a phenyl group and
$R_4$ denotes a phenyl group monosubstituted by the group $R_6$, wherein
$R_6$ denotes an N-methyl-imidazol-2-yl group,
an unbranched $C_{1-3}$-alkyl group which is terminally substituted by a $C_{1-4}$-alkylamino, di-($C_{1-4}$-alkyl)-amino, piperidino or 2,6-dimethyl-piperidino group,
a group of formula

$$-N(R_{12})-CO-(CH_2)_p-R_{13} \quad (IV),$$

wherein
$R_{12}$ denotes a $C_{1-3}$-alkyl group,
p denotes one of the numbers 1 or 2 and
$R_{13}$ denotes a di-($C_{1-3}$-alkyl)-amino group,
or a group of formula

$$-N(R_{14})-(CH_2)_q-(CO)_r-R_{15} \quad (V),$$

wherein
$R_{14}$ denotes a $C_{1-3}$-alkyl-carbonyl or $C_{1-3}$-alkylsulphonyl group,
q denotes one of the numbers 1, 2 or 3,
r denotes the number 1 or, if q is one of the numbers 2 or 3, r may also denote the number 0 and
$R_{15}$ denotes a di-($C_{1-3}$-alkyl)-amino group,
wherein the saturated alkyl moieties contained in the abovementioned groups which contain more than 2 carbon atoms may be straight-chain or branched, unless otherwise stated,
the tautomers, the diastereomers, the enantiomers, the mixtures thereof and the salts thereof.

A subgroup of most particularly preferred compounds of general formula I deserving special mention comprises those wherein
X, $R_1$, $R_3$ and $R_5$ are as hereinbefore defined,
$R_2$ denotes a methoxycarbonyl or ethoxycarbonyl group and
$R_4$ denotes a di-($C_{1-3}$-alkyl)-amino-$C_{1-3}$-alkylphenyl group or a phenyl group substituted by the group of formula

wherein $R_{12}$, p and $R_{13}$ are as hereinbefore defined,
the tautomers, the diastereomers, the enantiomers, the mixtures thereof and the salts thereof.

The following are mentioned as examples of particularly preferred compounds:
(a) 3-Z-[1-(4-(piperidin-1-yl-methyl)-anilino)-1-phenyl-methylene]-6-ethoxycarbonyl-2-indolinone,
(b) 3-Z-[(1-(4-(piperidin-1-yl-methyl)-anilino)-1-phenyl-methylene]-6-carbamoyl-2-indolinone,
(c) 3-Z-[1-(4-(piperidin-1-yl-methyl)-anilino)-1-phenyl-methylene]-6-methoxycarbonyl-2-indolinone,
(d) 3-Z-[1-(4-(dimethylaminomethyl)-anilino)-1-phenyl-methylene]-6-ethoxycarbonyl-2-indolinone,
(e) 3-Z-[1-(4-((2,6-dimethyl-piperidin-1-yl)-methyl)-anilino)-1-phenyl-methylene]-6-ethoxycarbonyl-2-indolinone,
(f) 3-Z-[1-(4-(N-(2-dimethylamino-ethyl)-N-acetyl-amino)-anilino)-1-phenyl-methylene]-6-ethoxycarbonyl-2-indolinone,
(g) 3-Z-[1-(4-(N-(3-dimethylamino-propyl)-N-acetyl-amino)-anilino)-1-phenyl-methylene]-6-ethoxycarbonyl-2-indolinone,
(h) 3-Z-[1-(4-(N-(2-dimethylamino-ethyl)-N-methylsulphonyl-amino)-anilino)-1-phenyl-methylene]-6-ethoxycarbonyl-2-indolinone,
(i) 3-Z-[1-(4-(dimethylaminomethyl)-anilino)-1-phenyl-methylene]-6-methoxycarbonyl-2-indolinone,
(j) 3-Z-[1-(4-(N-acetyl-N-dimethylaminocarbonylmethyl-amino)-anilino)-1-phenyl-methylene]-6-methoxycarbonyl-indolinone,
(k) 3-Z-[1-(4-ethylaminomethyl-anilino)-1-phenyl-methylene]-6-methoxycarbonyl-2-indolinone,
(l) 3-Z-[1-(4-(1-methyl-imidazol-2-yl)-anilino)-1-phenyl-methylene]-6-methoxycarbonyl-2-indolinone,
(m) 3-Z-[1-(4-(N-dimethylaminomethylcarbonyl-N-methyl-amino)-anilino)-1-phenyl-methylene]-6-methoxycarbonyl-indolinone,
(n) 3-Z-[1-(4-(N-(2-dimethylamino-ethyl)-N-methylsulphonyl-amino)-anilino)-1-phenyl-methylene]-6-methoxycarbonyl-indolinone,
(o) 3-Z-[1-(4-(N-(3-dimethylamino-propyl)-N-methylsulphonyl-amino)-anilino)-1-phenyl-methylene]-6-methoxycarbonyl-indolinone,
(p) 3-Z-[1-(4-(N-dimethylaminocarbonylmethyl-N-methylsulphonyl-amino)-anilino)-1-phenyl-methylene]-6-methoxycarbonyl-2-indolinone,
(q) 3-Z-[1-(4-(N-((2-dimethylamino-ethyl)-carbonyl)-N-methyl-amino)-anilino)-1-phenyl-methylene]-6-methoxycarbonyl-2-indolinone,
(r) 3-Z-[1-(4-(N-(2-dimethylamino-ethyl)-N-acetyl-amino)-anilino)-1-phenyl-methylene]-6-methoxycarbonyl-2-indolinone and
(s) 3-Z-[1-(4-methylaminomethyl-anilino)-1-phenyl-methylene]-6-methoxycarbonyl-2-indolinone,
their tautomers, their stereoisomers or the physiologically acceptable salts thereof.

Another subgroup of compounds of general formula I comprises those wherein
X denotes an oxygen or sulphur atom,
$R_1$ denotes a hydrogen atom or a prodrug group such as a $C_{1-4}$-alkoxycarbonyl or $C_{2-4}$-alkanoyl group,
$R_2$ denotes a carboxy group, a straight-chain or branched $C_{1-6}$-alkoxycarbonyl group, a $C_{5-7}$-cycloalkoxycarbonyl or phenyl-$C_{1-3}$-alkoxycarbonyl group, an aminocarbonyl or $C_{1-2}$-alkylaminocarbonyl group or, if $R_4$ does not denote an aminosulphonyl-phenyl or N—($C_{1-5}$-alkyl)-$C_{1-3}$-alkylaminocarbonyl-phenyl group, a di-($C_{1-2}$-alkyl)-aminocarbonyl group,
$R_3$ denotes a hydrogen atom, a $C_{1-6}$-alkyl, $C_{3-7}$-cycloalkyl, trifluoromethyl or heteroaryl group,
a phenyl or naphthyl group, a phenyl or naphthyl group mono- or disubstituted by a fluorine, chlorine, bromine or iodine atom, by a trifluoromethyl, $C_{1-3}$-alkyl or $C_{1-3}$-alkoxy group, whilst in the event of disubstitution the substituents may be identical or different and wherein the abovementioned unsubstituted as well as the mono- and disubstituted phenyl and naphthyl groups may additionally be substituted
by a hydroxy, hydroxy-$C_{1-3}$-alkyl or $C_{1-3}$-alkoxy-$C_{1-3}$-alkyl group,
by a cyano, carboxy, carboxy-$C_{1-3}$-alkyl, $C_{1-3}$-alkoxycarbonyl, aminocarbonyl, $C_{1-3}$-alkylamino-carbonyl or di-($C_{1-3}$-alkyl)-aminocarbonyl group,
by a nitro group,
by an amino, $C_{1-3}$-alkylamino, di-($C_{1-3}$-alkyl)-amino or amino-$C_{1-3}$-alkyl group,
by a $C_{1-3}$-alkylcarbonylamino, N—($C_{1-3}$-alkyl)-$C_{1-3}$-alkylcarbonylamino, $C_{1-3}$-alkylcarbonylamino-$C_{1-3}$-alkyl, N—($C_{1-3}$-alkyl)-$C_{1-3}$-alkylcarbonylamino-$C_{1-3}$-alkyl, $C_{1-3}$-alkyl-sulphonylamino, $C_{1-3}$-alkylsulphonylamino-$C_{1-3}$-alkyl, N—($C_{1-3}$-alkyl)-$C_{1-3}$-alkylsulphonylamino-$C_{1-3}$-alkyl or aryl-$C_{1-3}$-alkylsulphonylamino group,
by a cycloalkylamino, cycloalkyleneimino, cycloalkyleneiminocarbonyl, cycloalkyleneimino-$C_{1-3}$-alkyl, cycloalkyleneiminocarbonyl-$C_{1-3}$-alkyl or cycloalkyleneiminosulphonyl-$C_{1-3}$-alkyl group having 4 to 7 ring members in each case, whilst in each case the methylene group in position 4 of a 6- or 7-membered cycloalkyleneimino group may be replaced by an oxygen or sulphur atom, by a sulphinyl, sulphonyl, —NH or —N($C_{1-3}$-alkyl) group,
or by a heteroaryl or heteroaryl-$C_{1-3}$-alkyl group,
$R_4$ denotes a $C_{3-7}$-cycloalkyl group,
whilst the methylene group in the 4 position of a 6- or 7-membered cycloalkyl group may be substituted by an amino, $C_{1-3}$-alkylamino or di-($C_{1-3}$-alkyl)-amino group or replaced by an —NH or —N($C_{1-3}$-alkyl) group,
or a phenyl group substituted by the group $R_6$, which may additionally be substituted by a fluorine, chlorine, bromine or iodine atom, by a $C_{1-5}$-alkyl, trifluoromethyl, $C_{1-3}$-alkoxy, carboxy, $C_{1-3}$-alkoxycarbonyl, aminosulphonyl, nitro or cyano group, wherein
$R_6$ denotes a hydrogen, fluorine, chlorine, bromine or iodine atom,
a cyano, nitro, $C_{1-5}$-alkyl, $C_{3-7}$-cycloalkyl, trifluoromethyl, phenyl, tetrazolyl or heteroaryl group,
a $C_{1-3}$-alkoxy group optionally substituted by 1 to 3 fluorine atoms, a $C_{1-3}$-alkoxy-$C_{1-3}$-alkoxy, phenyl-$C_{1-3}$-alkoxy, amino-$C_{2-3}$-alkoxy, $C_{1-3}$-alkylamino-$C_{2-3}$-alkoxy, di-($C_{1-3}$-alkyl)-amino-$C_{2-3}$-alkoxy, phenyl-$C_{1-3}$-alkylamino-$C_{2-3}$-alkoxy, N—($C_{1-3}$-alkyl)-phenyl-$C_{1-3}$-alkylamino-$C_{2-3}$-alkoxy, $C_{5-7}$-cycloalkyleneimino-$C_{2-3}$-alkoxy or $C_{1-3}$-alkylmercapto group,
a carboxy, $C_{1-4}$-alkoxycarbonyl, aminocarbonyl, $C_{1-3}$-alkylamino-carbonyl, N—($C_{1-3}$-alkyl)-$C_{1-3}$-alkylaminocarbonyl, phenyl-$C_{1-3}$-alkylamino-carbonyl, N—($C_{1-3}$-alkyl)-phenyl-$C_{1-3}$-alkylamino-carbonyl, piperazinocarbonyl or N—($C_{1-3}$-alkyl)-piperazinocarbonyl group,
a $C_{1-3}$-alkylaminocarbonyl or N—($C_{1-5}$-alkyl)-$C_{1-3}$-alkylaminocarbonyl group wherein an alkyl moiety is substituted by a carboxy or $C_{1-3}$-alkoxycarbonyl group or is substituted in the 2 or 3 position by a di-($C_{1-3}$-alkyl)-amino, piperazino, N—($C_{1-3}$-alkyl)-piperazino or a 4- to 7-membered cycloalkyleneimino group, a 4- to 7-membered cycloalkyleneimino group, wherein a methylene group linked to the imino group may be replaced by a carbonyl or sulphonyl group or the cycloalkylene moiety may be fused to a phenyl ring or one or two hydrogen atoms may each be replaced by a $C_{1-3}$-alkyl group and/or in each case the methylene group in the 4 position of a 6- or 7-membered cycloalkyleneimino group may be substituted by a carboxy, $C_{1-3}$-alkoxycarbonyl, aminocarbonyl, $C_{1-3}$-alkylaminocarbonyl, di-($C_{1-3}$-alkyl)-aminocarbonyl, phenyl-$C_{1-3}$-alkylamino or N—($C_{1-3}$-alkyl)-phenyl-$C_{1-3}$-alkylamino group or may be replaced by an oxygen or sulphur atom, by a sulphinyl, sulphonyl, —NH, —N($C_{1-3}$-alkyl), —N(phenyl), —N($C_{1-3}$-alkyl-carbonyl) or —N(benzoyl) group, a $C_{1-4}$-alkyl group which may be substituted by a hydroxy or $C_{1-3}$-alkoxy group, by an amino, $C_{1-7}$-alkylamino, di-($C_{1-7}$-alkyl)-amino, di-N—($C_{1-3}$-alkyl)-amino-$C_{2-3}$-alkylamino, tri-N,N,N'—($C_{1-3}$-alkyl)-amino-$C_{2-3}$-alkylamino, phenylamino, N-phenyl-$C_{1-3}$-alkyl-amino, phenyl-$C_{1-3}$-alkylamino, N—($C_{1-3}$-alkyl)-phenyl-$C_{1-3}$-alkylamino or di-(phenyl-$C_{1-3}$-alkyl)-amino group, by a $C_{1-3}$-alkylcarbonylamino, N—($C_{1-3}$-alkyl)-$C_{1-3}$-alkylcarbonylamino, $C_{1-3}$-alkoxycarbonyl-$C_{1-3}$-alkylamino or N—($C_{1-3}$-alkyl)-$C_{1-3}$-alkoxycarbonyl-$C_{1-3}$-alkylamino group, by a $C_{4-7}$-cycloalkylamino, $C_{4-7}$-cycloalkyl-$C_{1-3}$-alkylamino or $C_{4-7}$-cycloalkenylamino group wherein position 1 of the ring is not involved in the double bond and wherein the abovementioned groups may each additionally be substituted at the amino-nitrogen atom by a $C_{1-3}$-alkyl group wherein some or all of the hydrogen atoms are replaced by fluorine atoms, by a $C_{1-3}$-cycloalkyl, $C_{2-4}$-alkenyl or $C_{1-4}$-alkyl group, by a 4- to 7-membered cycloalkyleneimino group, wherein a methylene group linked to the imino group may be replaced by a carbonyl or sulphonyl group or the cycloalkylene moiety may be fused to a phenyl group or to an oxazolo, imidazolo, thiazolo, pyridino, pyrazino or pyrimidino group optionally substituted by a fluorine, chlorine, bromine or iodine atom, by a nitro, $C_{1-3}$-alkyl, $C_{1-3}$-alkoxy or amino group or one or two hydrogen atoms may each be replaced by a $C_{1-3}$-alkyl, $C_{5-7}$-cycloalkyl or phenyl group and/or in each case the methylene group in the 4 position of a 6- or 7-membered cycloalkyleneimino group may be substituted by a hydroxy, carboxy, $C_{1-4}$-alkoxycarbonyl, aminocarbonyl, $C_{1-3}$-alkylaminocarbonyl, di-($C_{1-3}$-alkyl)-aminocarbonyl, phenyl-$C_{1-3}$-alkylamino or N—($C_{1-3}$-alkyl)-phenyl-$C_{1-3}$-alkylamino group or may be replaced by an oxygen or sulphur atom, by a sulphinyl, sulphonyl, —NH, —N($C_{1-3}$-alkyl), —N(phenyl), —N($C_{1-3}$-alkyl-carbonyl) or —N(benzoyl) group, by a carboxy, $C_{1-3}$-alkoxycarbonyl, aminocarbonyl, $C_{1-3}$-alkylaminocarbonyl or di-($C_{1-3}$-alkyl)-aminocarbonyl group or by a 4- to 7-membered cycloalkyleneiminocarbonyl group, an amino, pyrrolidino, piperidino, morpholino, benzoylamino or N—($C_{1-3}$-alkyl)-benzoylamino group, an N—($C_{1-3}$-alkyl)-$C_{2-4}$-alkanoylamino group which is additionally substituted in the alkyl moiety by a carboxy or $C_{1-3}$-alkoxycarbonyl group, a group of formula $$—N(R_8)—CO—(CH_2)_n—R_9 \qquad (II),$$

wherein $R_8$ denotes a hydrogen atom or a $C_{1-3}$-alkyl group, n denotes one of the numbers 0, 1, 2 or 3 and $R_9$ denotes an amino, $C_{1-4}$-alkylamino, phenylamino, N—($C_{1-4}$-alkyl)-phenylamino, benzylamino, N—($C_{1-4}$-alkyl)-benzylamino or di-($C_{1-4}$-alkyl)-amino group, a 4- to 7-membered cycloalkyleneimino group, whilst in each case the methylene group in the 4 position of a 6- or 7-membered cycloalkyleneimino group may be replaced by an oxygen or sulphur atom, by a sulphinyl, sulphonyl, —NH, —N($C_{1-3}$-alkyl), —N(phenyl), —N($C_{1-3}$-alkyl-carbonyl) or —N(benzoyl) group, or, if n denotes one of the numbers 1, 2 or 3, it may also denote a hydrogen atom, a group of formula $$—N(R_{10})—(CH_2)_m—(CO)_o—R_{11} \qquad (III),$$

wherein $R_{10}$ denotes a hydrogen atom, a $C_{1-3}$-alkyl group, a $C_{1-3}$-alkylcarbonyl, arylcarbonyl, phenyl-$C_{1-3}$-alkylcarbonyl, $C_{1-3}$-alkylsulphonyl, arylsulphonyl or phenyl-$C_{1-3}$-alkylsulphonyl group, m denotes one of the numbers 1, 2, 3 or 4, o denotes one of the numbers 0 or 1 and $R_{11}$ denotes an amino, $C_{1-4}$-alkylamino, phenylamino, N—($C_{1-4}$-alkyl)-phenylamino, benzylamino, N—($C_{1-4}$-alkyl)-benzyl-amino or di-($C_{1-4}$-alkyl)-amino group, a 4- to 7-membered cycloalkyleneimino group, wherein the cycloalkylene moiety may be fused to a phenyl ring or in each case the methylene group in the 4 position of a 6- or 7-membered cycloalkyleneimino group may be replaced by an oxygen or sulphur atom, by a sulphinyl, sulphonyl, —NH, —N($C_{1-3}$-alkyl), —N(phenyl), —N($C_{1-3}$-alkyl-carbonyl) or —N(benzoyl) group, a $C_{1-3}$-alkoxy group or a di-($C_{1-4}$-alkyl)-amino-$C_{1-3}$-alkylamino group optionally substituted in the 1 position by a $C_{1-3}$-alkyl group, or an N—($C_{1-3}$-alkyl)-$C_{1-5}$-alkylsulphonylamino or N—($C_{1-3}$-alkyl)-phenylsulphonylamino group wherein the alkyl moiety is additionally substituted by a cyano or carboxy group, wherein all the single-bonded or fused phenyl groups contained in the groups mentioned under $R_6$ may be mono- or disubstituted by fluorine, chlorine, bromine or iodine atoms, by $C_{1-5}$-alkyl, trifluoromethyl, $C_{1-3}$-alkoxy, carboxy, $C_{1-3}$-alkoxycarbonyl, aminosulphonyl, nitro or cyano groups, wherein the substituents may be identical or different, or two adjacent hydrogen atoms of the phenyl groups may be replaced by a methylenedioxy group, and $R_5$ denotes a hydrogen atom or a $C_{1-3}$-alkyl group, wherein by an aryl group is meant a phenyl or naphthyl group optionally mono- or disubstituted by a fluorine, chlorine, bromine or iodine atom, by a trifluoromethyl, $C_{1-3}$-alkyl or $C_{1-3}$-alkoxy group and by a heteroaryl group is meant a monocyclic 5- or 6-membered heteroaryl group optionally substituted by a $C_{1-3}$-alkyl group, wherein the 6-membered heteroaryl group contains one, two or three nitrogen atoms and the 5-membered heteroaryl group contains an imino group optionally substituted by a $C_{1-3}$-alkyl group, an oxygen or sulphur atom or an imino group optionally substituted by a $C_{1-3}$-alkyl group and an oxygen or sulphur atom or one or two nitrogen atoms, and moreover a phenyl ring may be fused to the abovementioned monocyclic heterocyclic groups via two adjacent carbon atoms, the saturated alkyl and alkoxy moieties present in the groups defined above which contain more than 2 carbon atoms also include the branched isomers thereof such as, for example, the isopropyl, tert.butyl or isobutyl group, unless otherwise stated, and additionally any carboxy, amino or imino group present may be substituted by a group which can be cleaved in vivo, the isomers and the salts thereof.

A further subgroup of compounds of general formula I which deserves special mention is the subgroup wherein the substituent in the 6 position of the substituted indolinone of general formula I comprises a substituted amido group.

The above exemplified compounds, their tautomers, their stereoisomers or the physiologically acceptable salts thereof, as well as their manufacturing process, have been described in WO 01/27081, the content of which is incorporated herein by reference.

Further compounds in accordance with the above general formula I which are preferred within the meaning of the present invention are the following compounds:

(t)  3-Z-[1-(4-(2-dimethylamino-ethoxy)-anilino)-1-phenyl-methylene]-6-methoxycarbonyl-2-indolinone
(u)  3-Z-[1-(4-(N-((4-methyl-piperazin-1-yl)-methylcarbonyl)-N-methyl-amino)-anilino)-1-phenyl-methylene]-6-methoxycarbonyl-2-indolinone,
(v)  3-Z-[1-(3-cyano-4-(N-dimethylaminomethylcarbonyl-N-methyl-amino)-anilino)-1-phenyl-methylene]-6-methoxycarbonyl-2-indolinone
(w)  3-Z-[1-(3-methoxy-4-(N-dimethylaminomethylcarbonyl-N-methyl-amino)-anilino)-1-phenyl-methylene]-6-methoxycarbonyl-2-indolinone
(x)  3-Z-[1-(4-(N-aminomethylcarbonyl-N-methyl-amino)-anilino)-1-phenyl-methylene]-6-methoxycarbonyl-2-indolinone
(y)  3-Z-[1-(4-(N—(N-(2-dimethylamino-ethyl)-N-methyl-aminomethylcarbonyl)-N-methyl-amino)-anilino)-1-phenyl-methylene]-6-methoxycarbonyl-2-indolinone
(z)  3-Z-[1-(4-(N-(di-(2-hydroxy-ethyl)-amino-methylcarbonyl)-N-methyl-amino)-anilino)-1-phenyl-methylene]-6-methoxycarbonyl-2-indolinone
(aa)  3-Z-[1-(4-(N-(imidazol-1-yl-methylcarbonyl)-N-methyl-amino)-anilino)-1-phenyl-methylene]-6-methoxycarbonyl-2indolinone
(ab)  3-Z-[1-(4-(N-dimethylaminomethylcarbonyl-amino)-anilino)-1-phenyl-methylene]-6-methoxycarbonyl-2-indolinone
(ac)  3-Z-[1-(4-(N-((4-methyl-[1,4]diazepan-1-yl)-methylcarbonyl)-N-methyl-amino)-anilino)-1-phenyl-methylene]-6-methoxycarbonyl-2-indolinone
(ad)  3-Z-[1-(4-(N-((1-methyl-piperidin-4-yl)-methylcarbonyl)-N-methyl-amino)-anilino)-1-phenyl-methylene]-6-methoxycarbonyl-2-indolinone
(ae)  3-Z-[1-(2,3-dimethyl-4-(N-((4-methyl-piperazin-1-yl)-methylcarbonyl)-amino)-anilino)-1-phenyl-methylene]-6-methoxycarbonyl-2-indolinone
(af)  3-Z-[1-(4-(N-((4-methyl-piperazin-1-yl)-methylcarbonyl)-amino)-anilino)-1-phenyl-methylene]-6-methoxycarbonyl-2-indolinone
(ag)  3-Z-[1-(4-(N-((4-methyl-piperazin-1-yl)-carbonyl)-N-methyl-amino)-anilino)-1-phenyl-methylene]-6-methoxycarbonyl-2-indolinone
(ah)  3-Z-[1-(4-(N-(3-dimethylamino-propyl)-N-acetyl-amino)-anilino)-1-phenyl-methylene]-6-methoxycarbonyl-2-indolinone
(ai)  3-Z-[1-(4-(N-((3-dimethylamino-propyl)-aminocarbonyl)-N-methyl-amino)-anilino)-1-phenyl-methylene]-6-methoxycarbonyl-2-indolinone
(aj)  3-Z-[1-anilino-1-phenyl-methylene]-6-methoxycarbonyl-2-indolinone
(ak)  3-Z-[1-(4-(N-methyl-N-methylsulphonyl-amino)-anilino)-1-phenyl-methylene]-6-methoxycarbonyl-2-indolinone
(al)  3-Z-[1-cyclohexylamino-1-phenyl-methylene]-6-methoxycarbonyl-2-indolinone
(am) 3-Z-[1-(4-(4-methylpiperazin-1-yl-methyl)-anilino)-1-phenyl-methylene]-6-carboxy-2-indolinone
(an) 3-Z-[1-(4-methylaminomethyl-anilino)-1-phenyl-methylene]-6-carboxy-2-indolinone
(ao)  3-Z-[1-(4-(morpholin-4-yl-methyl)-anilino)-1-phenyl-methylene]-6-carboxy-2-indolinone
(ap)  3-Z-[1-(4-(N-(2-dimethylamino-ethyl)-N-methylsulphonyl-amino)-anilino)-1-phenyl-methylene]-6-carboxy-2-indolinone
(aq)  3-Z-[1-(4-(di-(2-hydroxy-ethyl)-amino-methyl)-anilino)-1-phenyl-methylene]-6-carboxy-2-indolinone
(ar)  3-Z-[1-(4-(N-((4-methyl-piperazin-1-yl)-methylcarbonyl)-N-methyl-amino)-anilino)-1-phenyl-methylene]-6-carboxy-2-indolinone
(as)  3-Z-[1-(4-(N-(morpholin-4-yl-methylcarbonyl)-N-methyl-amino)-anilino)-1-phenyl-methylene]-6-carboxy-2-indolinone
(at)  3-Z-[1-(4-(N—(N-(2-dimethylamino-ethyl)-N-methyl-aminomethylcarbonyl)-N-methyl-amino)-anilino)-1-phenyl-methylene]-6-carboxy-2-indolinone
(au)  3-Z-[1-(4-(2-dimethylamino-ethoxy)-anilino)-1-phenyl-methylene]-6-carboxy-2-indolinone
(av)  3-Z-[1-cyclohexylamino-1-phenyl-methylene]-6-carboxy-2-indolinone
(aw)  3-Z-[1-(4-dimethylaminomethyl-anilino)-1-(3-(2-carboxy-ethyl)-phenyl)-methylene]-6-methoxycarbonyl-2-indolinone
(ax)  3-Z-[1-(4-(2-dimethylamino-ethyl)-anilino)-1-(3-(2-carboxy-ethyl)-phenyl)-methylene]-6-methoxycarbonyl-2-indolinone
(ay)  3-Z-[1-(4-(1-methyl-imidazol-2-yl)-anilino)-1-(3-(2-carboxy-ethyl)-phenyl)-methylene]-6-methoxycarbonyl-2-indolinone (az) 3-Z-[1-(4-dimethylaminomethyl-anilino)-1-(4-(2-carboxy-ethyl)-phenyl)-methylene]-6-methoxycarbonyl-2-indolinone
(ba) 3-Z-[1-(4-(2-dimethylamino-ethyl)-anilino)-1-phenyl-methylene]-6-ethylmethylcarbamoyl-2-indolinone
(bb) 3-Z-[1-(4-dimethylaminomethyl-anilino)-1-phenyl-methylene]-6-ethylmethylcarbamoyl-2-indolinone
(bc) 3-Z-[1-((1-methyl-piperidin-4-yl)-amino-1-phenyl-methylene]-6-ethylmethylcarbamoyl-2-indolinone
(bd) 3-Z-[1-(trans-4-dimethylamino-cyclohexylamino)-1-phenyl-methylene]-6-ethylmethylcarbamoyl-2-indolinone
(be) 3-Z-[1-(4-(2-diethylamino-ethoxy)-anilino)-1-phenyl-methylene]-6-ethylmethylcarbamoyl-2-indolinone
(bf) 3-Z-[1-(4-(N-(3-dimethylamino-propyl)-N-propionyl-amino)-anilino)-1-phenyl-methylene]-6-ethylmethylcarbamoyl-2-indolinone
(bg) 3-Z-[1-(4-(N-((4-methyl-piperazin-1-yl)-methylcarbonyl)-N-methyl-amino)-anilino)-1-phenyl-methylene]-6-ethylmethylcarbamoyl-2-indolinone
(bh) 3-Z-[l-cyclohexylamino-1-phenyl-methylene]-6-ethylmethylcarbamoyl-2-indolinone
(bi) 3-Z-[1-(4-(N-(2-dimethylamino-ethyl)-N-acetyl-amino)-anilino)-1-phenyl-methylene]-6-ethylmethylcarbamoyl-2-indolinone
(bj) 3-Z-[1-(3-diethylaminomethyl-anilino)-1-phenyl-methylene]-6-ethylmethylcarbamoyl-2-indolinone
(bk) 3-Z-[1-(4-(N-dimethylaminomethylcarbonyl-N-methyl-amino)-anilino)-1-phenyl-methylene]-6-ethylmethylcarbamoyl-2-indolinone
(bl) 3-Z-[1-(4-(N-(2-dimethylamino-ethyl)-N-methylsulphonyl-amino)-anilino)-1-phenyl-methylene]-6-ethylmethylcarbamoyl-2-indolinone
(bm) 3-Z-[1-anilino-1-phenyl-methylene]-6-ethylmethylcarbamoyl-2-indolinone
(bn) 3-Z-[1-(4-ethylaminomethyl-anilino)-1-phenyl-methylene]-6-ethylmethylcarbamoyl-2-indolinone
(bo) 3-Z-[1-(4-((2-diethylamino-ethyl)-anilino)-1-phenyl-methylene]-6-ethylmethylcarbamoyl-2-indolinone
(bp) 3-Z-[1-(4-(N-(3-dimethylamino-propyl)-N-acetyl-amino)-anilino)-1-phenyl-methylene]-6-ethylmethylcarbamoyl-2-indolinone
(bq) 3-Z-[1-(4-(N-methyl-N-methylsulphonyl-amino)-anilino)-1-phenyl-methylene]-6-ethylmethylcarbamoyl-2-indolinone
(br) 3-Z-[1-(4-methoxycarbonyl-anilino)-1-phenyl-methylene]-6-ethylmethylcarbamoyl-2-indolinone
(bs) 3-Z-[1-(4-carboxy-anilino)-1-phenyl-methylene]-6-ethylmethylcarbamoyl-2-indolinone
(bt) 3-Z-[1-(4-(N-(dimethylamino-carbonylmethyl)-N-methylsulphonyl-amino)-anilino)-1-phenyl-methylene]-6-ethylmethylcarbamoyl-2-indolinone
(bu) 3-Z-[1-(4-(2-dimethylamino-ethoxy)-anilino)-1-phenyl-methylene]-6-ethylmethylcarbamoyl-2-indolinone
(bv) 3-Z-[1-(4-(N-((4-methyl-piperazin-1-yl)-methylcarbonyl)-N-methyl-amino)-anilino)-1-phenyl-methylene]-6-ethylmethylcarbamoyl-2-indolinone
(bw) 3-Z-[1-(4-(N-(2-dimethylamino-ethyl)-N-methylsulphonyl-amino)-anilino)-1-phenyl-methylene]-6-ethylcarbamoyl-2-indolinone
(bx) 3-Z-[1-(4-(2-dimethylamino-ethoxy)-anilino)-1-phenyl-methylene]-6-ethylmethylcarbamoyl-2-indolinone
(by) 3-Z-[1-(4-(N-dimethylaminomethylcarbonyl-N-methyl-amino)-anilino)-1-phenyl-methylene]-6-ethylcarbamoyl-2-indolinone
(bz) 3-Z-[1-(4-dimethylaminomethyl-anilino)-1-phenyl-methylene]-6-ethylcarbamoyl-2-indolinone
(ca) 3-Z-[1-(4-(N-(2-dimethylamino-ethyl)-N-acetyl-amino)-anilino)-1-phenyl-methylene]-6-ethylcarbamoyl-2-indolinone
(cb) 3-Z-[1-(4-(N-(3-dimethylamino-propyl)-N-acetyl-amino)-anilino)-1-phenyl-methylene]-6-ethylcarbamoyl-2-indolinone
(cc) 3-Z-[1-(4-carbamoyl-anilino)-1-phenyl-methylene]-6-ethylmethylcarbamoyl-2-indolinone
(cd) 3-Z-[1-(4-(N-(2-diethylamino-ethyl)-carbamoyl)-anilino)-1-phenyl-methylene]-6-ethylmethylcarbamoyl-2-indolinone
(ce) 3-Z-[1-(4-((4-methyl-piperazin-1-yl)-carbonyl)-anilino)-1-phenyl-methylene]-6-ethylmethylcarbamoyl-2-indolinone
(cf) 3-Z-[1-(4-((4-methyl-piperazin-1-yl)-carbonyl)-anilino)-1-phenyl-methylene]-6-ethylcarbamoyl-2-indolinone
(cg) 3-Z-[1-(4-((4-ethyl-piperazin-1-yl)-carbonyl)-anilino)-1-phenyl-methylene]-6-ethylmethylcarbamoyl-2-indolinone
(ch) 3-Z-[1-(4-(N-ethyl-N-(2-dimethylamino-ethyl)-carbamoyl)-anilino)-1-phenyl-methylene]-6-ethylmethylcarbamoyl-2-indolinone
(ci) 3-Z-[1-(4-(N-((4-methyl-piperazin-1-yl)-methylcarbonyl)-N-methyl-amino)-anilino)-1-phenyl-methylene]-6-diethylcarbamoyl-2-indolinone
(cj) 3-Z-[1-(4-((cis-3,5-dimethyl-piperazin-1-yl)-carbonyl)-anilino)-1-phenyl-methylene]-6-ethylmethylcarbamoyl-2-indolinone
(ck) 3-Z-[1-(4-((4-ethyl-piperazin-1-yl)-carbonyl)-anilino)-1-phenyl-methylene]-6-ethylcarbamoyl-2-indolinone
(cl) 3-Z-[1-(4-(N-(2-diethylamino-ethyl)-carbamoyl)-anilino)-1-phenyl-methylene]-6-ethylmethylcarbamoyl-2-indolinone
(cm) 3-Z-[1-(4-((cis-3,5-dimethyl-piperazin-1-yl)-carbonyl)-anilino)-1-phenyl-methylene]-6-ethylcarbamoyl-2-indolinone
(cn) 3-Z-[1-(4-(N-(3-dimethylamino-propyl)-N-methylsulphonyl-amino)-anilino)-1-phenyl-methylene]-6-ethylcarbamoyl-2-indolinone
(co) 3-Z-[1-(4-(N-dimethylaminomethylcarbonyl-N-methyl-amino)-anilino)-methylene]-6-methoxycarbonyl-2-indolinone
(cp) 3-Z-[1-(4-dimethylaminomethyl-anilino)-methylene]-6-methoxycarbonyl-2-indolinone
(cq) 3-Z-[1-(4-(N-((4-methyl-piperazin-1-yl)-methylcarbonyl)-N-methyl-amino)-anilino)-methylene]-6-methoxycarbonyl-2-indolinone
(cr) 3-Z-[1-(4-(N-((4-methyl-piperazin-1-yl)-methylcarbonyl)-N-methyl-amino)-anilino)-methylene]-6-ethylcarbamoyl-2-indolinone
(cs) 3-Z-[1-(4-dimethylaminomethyl-anilino)-methylene]-6-ethylcarbamoyl-2-indolinone
(ct) 3-Z-[1-(4-(piperidin-1-yl-methyl)-anilino)-methylene]-6-ethylcarbamoyl-2-indolinone
(cu) 3-Z-[1-(4-(N-(3-dimethylamino-propyl)-N-acetyl-amino)-anilino)-methylene]-6-ethylcarbamoyl-2-indolinone, their tautomers, their stereoisomers or the physiologically acceptable salts thereof.

These compounds may be prepared analogously to the compounds of WO 01/27081 and using the methods described hereafter.

Abbreviations Used:
HOBt=1-hydroxy-1H-benzotriazole
TBTU=O-benzotriazol-1-yl-N,N,N',N'-tetramethyluronium-tetrafluoroborate
DEPC=diethyl pyrocarbonate
n.d.=not determined EXAMPLES (t) To (al)

The following compounds of general formula II are prepared analogously to the compounds described in WO 01/27081:

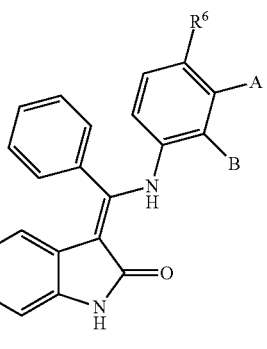

(II)

| Example | A | B | $R^6$ | Formula | Mass spectrum | Melting point [° C.] | $R_f$-value* |
|---|---|---|---|---|---|---|---|
| (t) | —H | —H | —O(CH$_2$)$_2$—NMe$_2$ | C$_{27}$H$_{27}$N$_3$O$_4$ | 456 [m − H]$^-$ | n.b. | 0.30 (A) |
| (u) | —H | —H | (piperazinyl-acetyl-N(Me)- group) | C$_{31}$H$_{33}$N$_5$O$_4$ | 540 [m + H]$^+$ | 250-252 | 0.60 (B) |
| (v) | —CN | —H | —N(Me)—(CO)—CH$_2$—NMe$_2$ | C$_{29}$H$_{27}$N$_5$O$_4$ | 510 [m + H]$^+$ | 163-165 | 0.35 (A) |
| (w) | —OMe | —H | —N(Me)—(CO)—CH$_2$—NMe$_2$ | C$_{29}$H$_{30}$N$_4$O$_5$ | 515 [m + H]$^+$ | 160-163 | 0.40 (A) |
| (x) | —H | —H | —N(Me)—(CO)—CH$_2$—NH$_2$ | C$_{26}$H$_{24}$N$_4$O$_4$ | 457 [m + H]$^+$ | 221 | 0.45 (C) |
| (y) | —H | —H | (N(Me)-CH$_2$CH$_2$-NMe$_2$ amide group) | C$_{24}$H$_{21}$N$_3$O$_3$ | 542 [m + H]$^+$ | 265 | n.d. |
| (z) | —H | —H | (bis(2-hydroxyethyl)amino-acetyl-N(Me)- group) | C$_{30}$H$_{32}$N$_4$O$_6$ | 545 [m + H]$^+$ | 199-202 | 0.40 (A) |
| (aa) | —H | —H | (imidazolyl-acetyl-N(Me)- group) | C$_{29}$H$_{25}$N$_5$O$_4$ | 508 [m + H]$^+$ | 271 | 0.45 (A) |

-continued

| Example | A | B | R⁶ | Formula | Mass spectrum | Melting point [° C.] | $R_f$-value* |
|---|---|---|---|---|---|---|---|
| (ab) | —H | —H | —NH—(CO)—CH₂—NMe₂ | $C_{27}H_{26}N_4O_4$ | 471 [m + H]⁺ | 250-255 | 0.50 (A) |
| (ac) | —H | —H | *N-methyl-homopiperazinyl-acetyl N-methylamide* | $C_{32}H_{35}N_5O_4$ | 554 [m + H]⁺ | 180-185 | 0.50 (D) |
| (ad) | —H | —H | *N-methyl-piperidin-4-yl-acetyl N-methylamide* | $C_{32}H_{34}N_4O_4$ | 539 [m + H]⁺ | 190-193 | 0.40 (D) |
| (ae) | —CH₃ | —CH₃ | *4-methyl-piperazinyl-acetyl amide* | $C_{32}H_{35}N_5O_4$ | 554 [m + H]⁺ | 254-257 | 0.50 (C) |
| (af) | —H | —H | *4-methyl-piperazinyl-acetyl amide* | $C_{30}H_{31}N_5O_4$ | 526 [m + H]⁺ | 170-175 | 0.40 (A) |
| (ag) | —H | —H | *4-methyl-piperazine-1-carbonyl N-methylamide* | $C_{30}H_{31}N_5O_4$ | 526 [m + H]⁺ | 205-208 | 0.40 (A) |
| (ah) | —H | —H | —N(Me)—(CO)—(CH₂)₃—NMe₂ | $C_{30}H_{32}N_4O_4$ | 511 [m − H]⁻ | 166-170 | 0.40 (C) |
| (ai) | —H | —H | —N(Me)—(CO)—(CH₂)₃—NMe₂ | $C_{30}H_{33}N_5O_4$ | 528 [m + H]⁺ | 166-170 | 0.30 (E) |
| (aj) | —H | —H | —H | $C_{23}H_{18}N_2O_3$ | 371 [m + H]⁺ | 275-280 | 0.80 (C) |
| (ak) | —H | —H | —N(SO₂Me)—CH₃ | $C_{25}H_{23}N_3O_5S$ | 478 [m + H]⁺ | 278-282 | 0.70 (C) |

*Solvents:
(A): silica gel, methylene chloride/methanol 9:1
(B): aluminum oxide, methylene chloride/methanol 20:1
(C): silica gel, methylene chloride/methanol/ammonia 9:1:0.1
(D): silica gel, methylene chloride/methanol/ammonia 5:1:0.01
(E): silica gel, methylene chloride/methanol/ammonia 9:1:0.01

The following compound is prepared analogously:

(al) 3-Z-(1-cyclohexylamino-1-phenyl-methylene)-6-methoxycarbonyl-2-indolinone $R_f$-value: 0.60 (silica gel, methylene chloride/methanol=9:1)

Melting point: 236-243° C.

$C_{23}H_{24}N_2O_3$

Mass spectrum: m/z=377 [m+H]$^+$

EXAMPLES (am) To (av)

The following compounds of general formula III are prepared analogously to the compounds described in WO 01/27081:

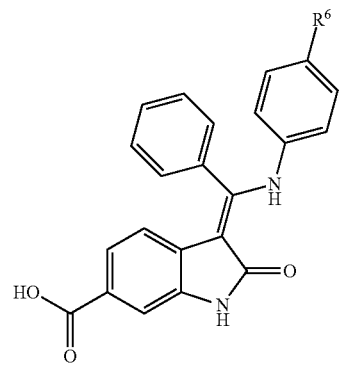

(III)

| Example | R$^6$ | Formula | Mass spectrum | Melting point [° C.] | $R_f$-value* |
|---|---|---|---|---|---|
| (am) | —CH$_2$—(4-methylpiperazin-1-yl) | $C_{28}H_{28}N_4O_3$ | 467 [m − H]$^-$ | 275 | 0.50 (A) |
| (an) | —CH$_2$—NHMe | $C_{24}H_{21}N_3O_3$ | 398 [m − H]$^-$ | 287 | 0.70 (A) |
| (ao) | —CH$_2$-morpholin-4-yl | $C_{27}H_{25}N_3O_4$ | 454 [m − H]$^-$ | 335 | 0.70 (A) |
| (ap) | —N(SO$_2$Me)—(CH$_2$)$_2$—NMe$_2$ | $C_{27}H_{28}N_4O_5S$ | 519 [m − H]$^-$ | 280 | 0.70 (A) |
| (aq) | —CH$_2$—N(CH$_2$CH$_2$OH)$_2$ | $C_{27}H_{27}N_3O_5$ | 496 [m + Na]$^+$ | 256-257 | 0.75 (A) |
| (ar) | —N(Me)—C(O)—CH$_2$—(4-methylpiperazin-1-yl) | $C_{30}H_{31}N_5O_4$ | 526 [m + H]$^+$ | 346 | 0.60 (A) |
| (as) | —N(Me)—C(O)—CH$_2$-morpholin-4-yl | $C_{29}H_{28}N_4O_5$ | 513 [m + H]$^+$ | 237-238 | 0.70 (A) |

| Example | R⁶ | Formula | Mass spectrum | Melting point [° C.] | R_f-value* |
|---|---|---|---|---|---|
| (at) | 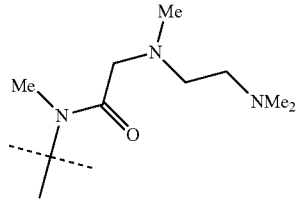 | C$_{30}$H$_{33}$N$_5$O$_4$ | 528 [m + H]⁺ | 238-240 | 0.50 (A) |
| (au) | —O(CH$_2$)$_2$—NMe$_2$ | C$_{26}$H$_{25}$N$_3$O$_4$ | 444 [m + H]⁺ | n.b. | 0.35 (B) |

*Solvents:
(A): reversed phase RP8, methanol/brine (5%) = 4:1
(B): silica gel, methylene chloride/methanol 4:1

The following compound is prepared analogously:
(av) 3-Z-(1-cyclohexylamin-1-phenyl-methylene)-6-carboxy-2-indolinone
Rf value: 0.50 (silica gel, methylene chloride/methanol=9:1)
Melting point: 347-350° C.
C$_{22}$H$_{22}$N$_2$O$_3$
Mass spectrum: m/z=363 [m+H]⁺

EXAMPLES (aw) To (az)

(aw) 3-Z-[1-(3-(dimethylaminomethyl)-anilino)-1-(3-(2-carboxy-ethyl)-phenyl)-methylene]-6-methoxycarbonyl-2-indolinone
(ax) 3-Z-[1-(4-(2-dimethylamino-ethyl)-anilino)-1-(3-(2-carboxy-ethyl)-phenyl)-methylene]-6-methoxycarbonyl-2-indolinone
(ay) 3-Z-[1-(4-(1-methyl-imidazol-2-yl)-anilino)-1-(3-(2-carboxy-ethyl)-phenyl)-methylene]-6-methoxycarbonyl-2-indolinone
(az) 3-Z-[1-(4-(dimethylaminomethyl)-anilino)-1-(4-(2-carboxy-ethyl)-phenyl)-methylene]-6-methoxycarbonyl-2-indolinone
Preparation of the starting compounds:
(I.1) 1-acetyl-3-(1-hydroxy-1-(3-(2-ethoxycarbonyl-ethyl)-phenyl)-methylene)-6-methoxycarbonyl-2-indolinone
6.00 g 1-acetyl-6-methoxycarbonyl-2-indolinone, 6.30 g 3-(2-ethoxycarbonyl-ethyl)-benzoic acid (preparation analogously to Tetrahedron 1997, 53, 7335-7340) and 9.10 g TBTU are dissolved in 80 ml of dimethylformamide, 13.5 ml diisopropylmethylamine and 4.34 g HOBt are added and the mixture is stirred for 12 hrs at ambient temperature. After this time the solvent is removed, diluted hydrochloric acid is added and the residue is recrystallized from methylene chloride/methanol.
Yield: 10.6 g (94% of theory)
R$_f$ value: 0.50 (silica gel, methylene chloride/methanol=19:1)
Melting point: 80-84° C.
C$_{24}$H$_{23}$NO$_7$
Mass spectrum: m/z=438 [m+H]⁺
The following compounds are prepared analogously:
(I.2) 1-acetyl-3-(1-hydroxy-1-(4-(2-methoxycarbonyl-ethyl)-phenyl)-methylene)-6-methoxycarbonyl-2-indolinone
prepared from 1-acetyl-6-methoxycarbonyl-2-indolinone and 4-(2-methoxycarbonyl-ethyl)-benzoic acid (preparation analogously to Tetrahedron 1997, 53, 7335-7340)

R$_f$ value: 0.60 (silica gel, methylene chloride/methanol=19:1)
Melting point: 188-192° C.
C$_{23}$H$_{21}$NO$_7$
Mass spectrum: m/z=422 [m−H]⁻
(II.1) 1-acetyl-3-(1-methoxy-1-(3-(2-ethoxycarbonyl-ethyl)-phenyl)-methylene)-6-methoxycarbonyl-2-indolinone
7.17 g trimethyloxoniumtetrafluoroborate are slowly added to a solution of 10.6 g 1-acetyl-3-(1-hydroxy-1-(3-(2-ethoxycarbonyl-ethyl)-phenyl)-methylene)-6-methoxycarbonyl-2-indolinone (starting material I.1) and 12.5 ml ethyl-diisopropylamine in 100 ml methylene chloride. After stirring for 4 hrs at ambient temperature another 3.50 g trimethyloxoniumtetrafluoroborate are added and the mixture is stirred for 12 hrs at ambient temperature. After that time the mixture is washed twice with water, the organic phase is dried over magnesium sulphate and the solvent is removed. The residue is purified over a silica gel column with methylene chloride/methanol (97:3) as eluant.
Yield: 4.56 g (42% of theory)
R$_f$ value: 0.90 (silica gel, methylene chloride/methanol=20:1)
C$_{25}$H$_{25}$NO$_7$
Mass spectrum: m/z=452 [m+H]⁺
The following compounds are prepared analogously:
(II.2) 1-acetyl-3-(1-methoxy-1-(4-(2-methoxycarbonyl-ethyl)-phenyl)-methylene)-6-methoxycarbonyl-2-indolinone
prepared from 1-acetyl-3-(1-hydroxy-1-(4-(2-methoxycarbonyl-ethyl)-phenyl)-methylene)-6-methoxycarbonyl-2-indolinone (starting material I.2)
R$_f$ value: 0.80 (silica gel, methylene chloride/methanol=19:1)
Melting point: 112-117° C.
C$_{24}$H$_{23}$NO$_7$
Mass spectrum: m/z=438 [m+H]⁺
(III.1) 3-Z-[1-(4-(dimethylaminomethyl)-anilino)-1-(3-(2-ethoxycarbonyl-ethyl)-phenyl)-methylene]-6-methoxycarbonyl-2-indolinone
1.2 g 1-acetyl-3-(1-methoxy-1-(3-(2-ethoxycarbonyl-ethyl)-phenyl)-methylene)-6-methoxycarbonyl-2-indolinone (starting material II.1) and 0.32 g 4-(dimethylaminomethyl)-aniline are dissolved in 10 ml of dimethylformamide and stirred for 3 days at 110° C. After cooling the solvent is evaporated, the residue is taken up in 5 ml of methanol and 200 mg 20 percent sodiumethylatsolution in ethanol are added. The mixture is stirred for 1.5 hrs at ambient temperature, the solvent is removed and the residue is taken up in water. The aqueous phase is three times extracted with ethyl acetate and the combined organic phases are dried over sodium sulphate. After evaporation of the solvent the residue is purified over a silica gel column with methylene chloride/methanol (9:1) as eluant.

Yield: 0.33 g (35% of theory), $R_f$-value: 0.35 (silica gel, methylene chloride/methanol=9:1)

Melting point: 129-134° C.

$C_{31}H_{33}N_3O_5$

Mass spectrum: m/z=528 [m+H]$^+$

The following compounds are prepared analogously:

(III.2) 3-Z-[1-(4-(2-dimethylamino-ethyl)-anilino)-1-(3-(2-ethoxycarbonyl-ethyl)-phenyl)-methylene]-6-methoxy-carbonyl-2-indolinone prepared from 1-acetyl-3-(1-methoxy-1-(3-(2-ethoxycarbonyl-ethyl)-phenyl)-methylene)-6-methoxycarbonyl-2-indolinone (starting material II.1)

$R_f$-value: 0.30 (silica gel, methylene chloride/methanol=9:1)

Melting point: 174-177° C.

$C_{32}H_{35}N_3O_5$

Mass spectrum: m/z=542 [m+H]$^+$ (III.3) 3-Z-[1-(4-(1-methyl-imidazol-2-yl)-anilino)-1-(3-(2-ethoxycarbonyl-ethyl)-phenyl)-methylene]-6-methoxy-carbonyl-2-indolinone prepared from 1-acetyl-3-(1-methoxy-1-(3-(2-ethoxycarbonyl-ethyl)-phenyl)-methylene)-6-methoxycarbonyl-2-indolinone (starting material II.1)

$R_f$-value: 0.45 (silica gel, methylene chloride/methanol=9:1)

Melting point: 102° C.

$C_{32}H_{30}N_4O_5$

Mass spectrum: m/z=551 [m+H]$^+$ (III.4) 3-Z-[1-(4-(dimethylaminomethyl)-anilino)-1-(4-(2-methoxycarbonyl-ethyl)-phenyl)-methylene]-6-methoxy-carbonyl-2-indolinone prepared from 1-acetyl-3-(1-methoxy-1-(4-(2-methoxycarbonyl-ethyl)-phenyl)-methylene)-6-methoxycarbonyl-2-indolinone (starting material II.2)

$R_f$-value: 0.50 (silica gel, methylene chloride/methanol=9:1)

Melting point: 226-229° C.

$C_{30}H_{31}N_3O_5$

Mass spectrum: m/z=512 [m−H]$^-$

Preparation of the final compounds:

The following compounds of general formula IV are prepared analogously to the compounds described in WO 01/27081, starting from the above mentioned starting materials:

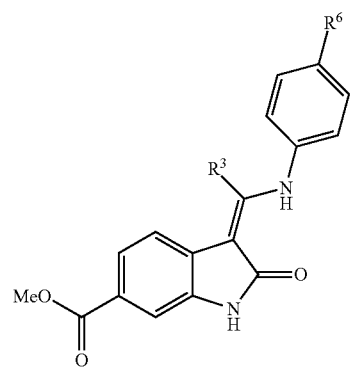

(IV)

| Example | R$^3$ | R$^6$ | Starting compound | Formula | Mass spectrum | Melting point [° C.] | R$_f$-value* |
|---|---|---|---|---|---|---|---|
| (aw) | COOH (3-substituted phenethyl) | —CH$_2$—NMe$_2$ | III.1 | C$_{29}$H$_{29}$N$_3$O$_5$ | 500 [m + H]$^+$ | 163-167 | 0.40 (A) |
| (ax) | COOH (3-substituted phenethyl) | —(CH$_2$)$_2$—NMe$_2$ | III.2 | C$_{30}$H$_{31}$N$_3$O$_5$ | 514 [m + H]$^+$ | 248-255 | 0.35 (A) |

-continued

| Example | R³ | R⁶ | Starting compound | Formula | Mass spectrum | Melting point [° C.] | $R_f$ value* |
|---|---|---|---|---|---|---|---|
| (ay) | COOH (with phenethyl group) | N-methyl imidazole with t-butyl | III.3 | $C_{30}H_{26}N_4O_5$ | 523 [m + H]⁺ | 184-190 | 0.35 (A) |
| (az) | HOOC (with phenethyl group, para) | —CH₂—NMe₂ | III.4 | $C_{29}H_{29}N_3O_5$ | 498 [m − H]⁻ | 190-195 | 0.20 (B) |

*Solvents:
(A): Reversed Phase RP8, methanol/brine (5%) = 4:1
(B): silica gel, methylene chloride/methanol 9:1

EXAMPLES (ba) TO (cn)

Preparation of the starting compounds:
(IV) 3-(1-hydroxy-1-phenyl-methylene)-6-carboxy-2-indolinone 11.0 g 1-acetyl-3-(1-methoxy-1-phenyl-methylene)-6-methoxycarbonyl-2-indolinone (preparation described in WO 01/27081) are dissolved in 500 ml of methanol and 160 ml of 1N sodium hydroxide solution are added. The mixture is stirred for 1 hr at ambient temperature and for 6 hrs at reflux. After that time another 20 ml of 1N sodium hydroxide solution are added and the mixture is stirred for another 3 hrs at reflux. 160 ml of 1N hydrochloric acid are added, the resulting residue is filtered off and dried at 100° C. The residue is used without further purification.

Yield: 7.60 g (86% of theory)

(V.1) 3-(1-hydroxy-1-phenyl-methylene)-6-(N-ethyl-methylcarbamoyl)-2-indolinone 5.50 g 3-(1-hydroxy-1-phenyl-methylene)-6-carboxy-2-indolinone (starting material IV), 7.54 g TBTU, 3.60 g HOBt and 17.1 ml ethyldiisopropylamine are dissolved in 200 ml of dimethylformamide. 2.70 ml of a 94-percent solution of N-methyl-ethylamine are added and the mixture is stirred for 12 hrs at ambient temperature. After that time the solvent is evaporated and the residue is purified over a silica gel column with methylene chloride/methanol/ammonia (9:1:0.1) as eluant.

Yield: 6.10 g (97% of theory)
$R_f$ value: 0.35 (silica gel, methylene chloride/methanol/ammonia=9:1:0.1)
$C_{18}H_{16}N_2O_3$
Mass spectrum: m/z=323 [m+H]⁺

The following compound is prepared analogously:
(V.2) 3-(1-hydroxy-1-phenyl-methylene)-6-ethylcarbamoyl-2-indolinone
prepared from 3-(1-hydroxy-1-phenyl-methylene)-6-carboxy-2-indolinone (starting material IV) und ethylamine $C_{18}H_{16}N_2O_3$
Mass spectrum: m/z=309 [m+H]⁺

Preparation of the final compounds:
(ba) 3-Z-[1-(4-(2-dimethylamino-ethyl)-anilino)-1-phenyl-methylene]-6-(N-ethyl-methylcarbamoyl)-2-indolinone 250 mg 3-(1-hydroxy-1-phenyl-methylene)-6-(N-ethyl-methylcarbamoyl)-2-indolinone (starting material V.1) and 382 mg 4-(2-dimethylamino-ethyl)-aniline are dissolved in 3 ml of tetrahydrofuran, 569 ml trimethylsilylimidazole are added and the mixture is stirred at 170° C. in a microwave oven. After cooling the solvent is evaporated and the residue is taken up in water. The residue is filtered off and vacuum-dried at 90° C.

Yield: 0.18 g (50% of theory),
$R_f$ value: 0.30 (silica gel, methylene chloride/methanol/ammonia=9:1:0.1)
Melting point: 195-200° C.
$C_{29}H_{32}N_4O_2$
Mass spectrum: m/z=469 [m+H]⁺

The following compounds of general formula V are prepared analogously to the above compound (ba), following the procedures described in WO 01/27081:

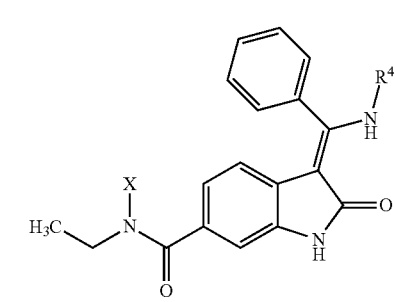

(V)

| Example | X | R⁴ | Formula | Mass spectrum | Melting point [° C.] | R$_f$-value* |
|---|---|---|---|---|---|---|
| (bb) | —CH₃ | 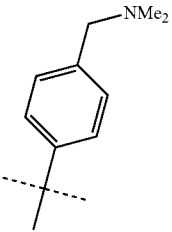 | C₂₈H₃₀N₄O₂ | 455 [m + H]⁺ | 239-243 | 0.35 (A) |
| (bc) | —CH₃ | 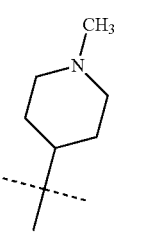 | C₂₅H₃₀N₄O₂ | 419 [m + H]⁺ | 267-271 | 0.35 (B) |
| (bd) | —CH₃ | 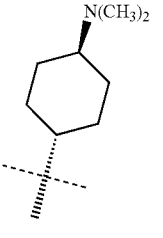 | C₂₇H₃₄N₄O₂ | 447 [m + H]⁺ | 133-138 | 0.30 (B) |
| (be) | —CH₃ | 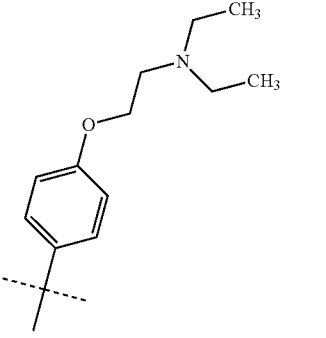 | C₃₁H₃₆N₄O₃ | 513 [m + H]⁺ | 191-196 | 0.45 (B) |
| (bf) | —CH₃ | 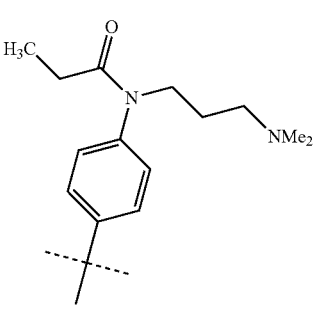 | C₃₃H₃₉N₅O₃ | 554 [m + H]⁺ | 258-262 | 0.40 (B) |

-continued

| Example | X | R⁴ | Formula | Mass spectrum | Melting point [° C.] | R_f-value* |
|---|---|---|---|---|---|---|
| (bg) | —CH₃ | [N-methylpiperazinyl-acetyl-N-methyl-4-substituted-phenyl group] | $C_{33}H_{38}N_6O_3$ | 567 [m + H]⁺ | 214-218 | 0.20 (B) |
| (bh) | —CH₃ | [cyclohexyl group] | $C_{25}H_{29}N_3O_2$ | 404 [m + H]⁺ | 239-242 | 0.70 (A) |
| (bi) | —CH₃ | [N-acetyl-N-(2-dimethylaminoethyl)-4-substituted-phenyl group] | $C_{31}H_{35}N_5O_3$ | 526 [m + H]⁺ | 237-240 | 0.30 (B) |
| (bj) | —CH₃ | [3-(diethylaminomethyl)phenyl group] | $C_{30}H_{34}N_4O_2$ | 483 [m + H]⁺ | 105-108 | 0.40 (B) |
| (bk) | —CH₃ | [N-methyl-N-(dimethylaminoacetyl)-4-substituted-phenyl group] | $C_{30}H_{33}N_5O_3$ | 512 [m + H]⁺ | 208-211 | 0.40 (B) |

-continued

| Example | X | R⁴ | Formula | Mass spectrum | Melting point [° C.] | R_f value* |
|---|---|---|---|---|---|---|
| (bl) | —CH₃ | H₃C—S(O)₂—N(CH₂CH₂NMe₂)—C₆H₄— | C₃₀H₃₅N₅O₄S | 562 [m + H]⁺ | 197-201 | 0.40 (B) |
| (bm) | —CH₃ | C₆H₅— | C₂₅H₂₃N₃O₂ | 398 [m + H]⁺ | 296-301 | 0.40 (B) |
| (bn) | —CH₃ | EtHN—CH₂—C₆H₄— | C₂₈H₃₀N₄O₂ | 455 [m + H]⁺ | 243-247 | 0.30 (A) |
| (bo) | —H | Me₂N—CH₂CH₂—C₆H₄— | C₂₈H₃₀N₄O₂ | 455 [m + H]⁺ | 328-332 | 0.30 (A) |
| (bp) | —CH₃ | H₃C—C(O)—N(CH₂CH₂CH₂NMe₂)—C₆H₄— | C₃₂H₃₇N₅O₃ | 540 [m + H]⁺ | 224-228 | 0.25 (A) |

-continued

| Example | X | R⁴ | Formula | Mass spectrum | Melting point [° C.] | R$_f$-value* |
|---|---|---|---|---|---|---|
| (bq) | —CH₃ | 4-(N-methyl-N-methylsulfonylamino)phenyl on tBu | C₂₇H₂₈N₄O₄S | 505 [m + H]⁺ | 265-269 | 0.40 (B) |
| (br) | —CH₃ | 4-(methoxycarbonyl)phenyl on tBu | C₂₇H₂₅N₃O₄ | 456 [m + H]⁺ | 254-257 | 0.60 (B) |
| (bs) | —CH₃ | 4-carboxyphenyl on tBu | C₂₆H₂₃N₃O₄ | 442 [m + H]⁺ | 316-321 | 0.10 (B) |
| (bt) | —CH₃ | 4-[N-(2-dimethylamino-2-oxoethyl)-N-methylsulfonylamino]phenyl on tBu | C₃₀H₃₃N₅O₅S | 576 [m + H]⁺ | 258-262 | 0.35 (B) |
| (bu) | —H | 4-(2-dimethylaminoethoxy)phenyl on tBu | C₂₈H₃₀N₄O₃ | 471 [m + H]⁺ | 308-311 | 0.35 (B) |

-continued
| Example | X | R⁴ | Formula | Mass spectrum | Melting point [° C.] | R_f value* |
|---|---|---|---|---|---|---|
| (bv) | —H | 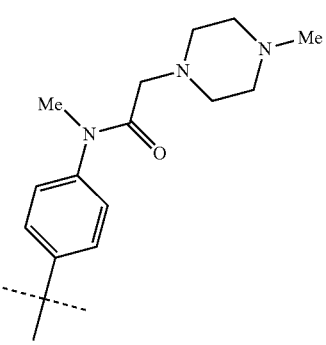 | C₃₂H₃₆N₆O₃ | 553 [m + H]⁺ | 279-283 | 0.60 (C) |
| (bw) | —H | 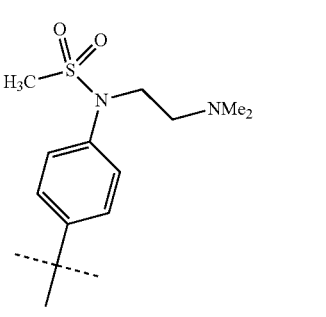 | C₂₉H₃₃N₅O₄S | 548 [m + H]⁺ | 213-217 | 0.35 (B) |
| (bx) | —CH₃ | 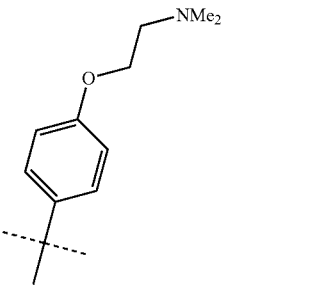 | C₂₉H₃₂N₄O₃ | 485 [m + H]⁺ | 218-222 | 0.40 (A) |
| (by) | —H | 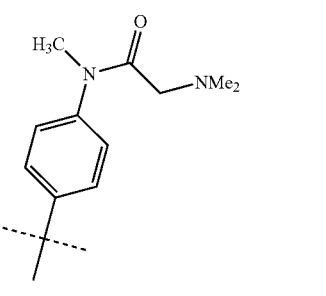 | C₂₉H₃₁N₅O₃ | 498 [m + H]⁺ | 130-134 | 0.35 (D) |
| (bz) | —H | 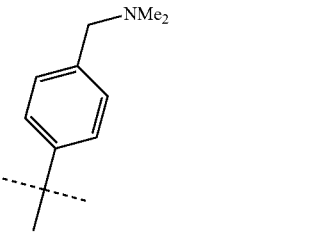 | C₂₇H₂₈N₄O₂ | 441 [m + H]⁺ | 341-344 | 0.45 (D) |

-continued

| Example | X | R⁴ | Formula | Mass spectrum | Melting point [° C.] | R_f-value* |
|---------|---|----|---------|---------------|----------------------|-----------|
| (ca) | —H | ![structure: H3C-C(=O)-N(CH2CH2NMe2)-C6H4- with dashed bond] | C₃₀H₃₃N₅O₃ | 512 [m + H]⁺ | 266-270 | 0.40 (D) |
| (cb) | —H | ![structure: H3C-C(=O)-N(CH2CH2CH2NMe2)-C6H4- with dashed bond] | C₃₁H₃₅N₅O₃ | 526 [m + H]⁺ | 198-202 | 0.40 (D) |
| (cc) | —CH₃ | ![structure: C(=O)NH2-C6H4- with dashed bond] | C₂₆H₂₄N₄O₃ | 441 [m + H]⁺ | 290-295 | 0.25 (B) |
| (cd) | —CH₃ | ![structure: C(=O)NH-CH2CH2-N(CH2CH3)2-C6H4- with dashed bond] | C₃₂H₃₇N₅O₃ | 540 [m + H]⁺ | 120-126 | 0.40 (B) |
| (ce) | —CH₃ | ![structure: C(=O)-N-methylpiperazine on C6H4- with dashed bond] | C₃₁H₃₃N₅O₃ | 524 [m + H]⁺ | 100-105 | 0.50 (B) |

-continued
| Example | X | R⁴ | Formula | Mass spectrum | Melting point [° C.] | R_f-value* |
|---|---|---|---|---|---|---|
| (cf) | —H | 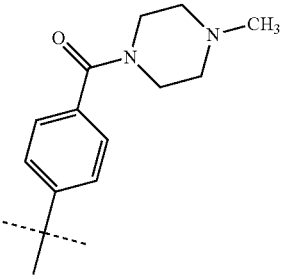 | C₃₀H₃₁N₅O₃ | 510 [m + H]⁺ | 288-292 | 0.40 (A) |
| (cg) | —CH₃ | 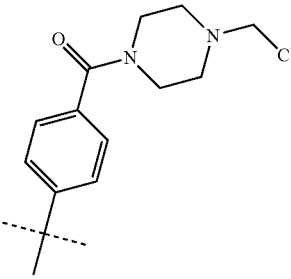 | C₃₂H₃₅N₅O₃ | 538 [m + H]⁺ | 157-163 | 0.30 (B) |
| (ch) | —CH₃ | 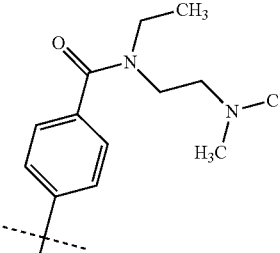 | C₃₂H₃₇N₅O₃ | 540 [m + H]⁺ | 162-169 | 0.20 (B) |
| (ci) | —CH₂CH₃ | 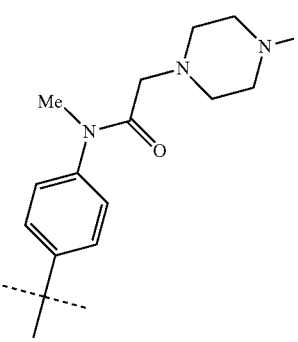 | C₃₄H₄₀N₆O₃ | 581 [m + H]⁺ | 195-198 | 0.50 (E) |
| (cj) | —CH₃ | 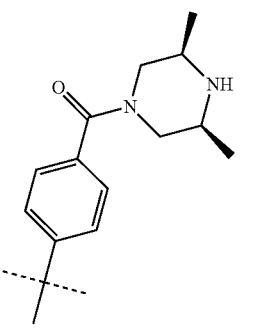 | C₃₂H₃₅N₅O₃ | 538 [m + H]⁺ | 238-242 | 0.35 (B) |

-continued

| Example | X | R⁴ | Formula | Mass spectrum | Melting point [° C.] | R_f value* |
|---|---|---|---|---|---|---|
| (ck) | —H | (4-piperazinyl-N-ethyl benzoyl group) | $C_{31}H_{33}N_5O_3$ | 524 [m + H]⁺ | 127-130 | 0.50 (D) |
| (cl) | —H | (N-(2-diethylaminoethyl)benzamide group) | $C_{31}H_{35}N_5O_3$ | 526 [m + H]⁺ | 250-253 | 0.40 (D) |
| (cm) | —H | (2,5-dimethylpiperazinyl benzoyl group) | $C_{32}H_{35}N_5O_3$ | 524 [m + H]⁺ | 217-220 | 0.40 (D) |
| (cn) | —H | (methanesulfonamido-N-(3-dimethylaminopropyl)phenyl group) | $C_{29}H_{33}N_5O_4S$ | 560 [m − H]⁻ | 171-175 | 0.45 (D) |

*Solvents:
(A): silica gel, methylene chloride/methanol 9:1
(B): silica gel, methylene chloride/methanol/ammonia 9:1:0.1
(C): aluminum oxide, methylene chloride/methanol 9:1
(D): aluminum oxide, methylene chloride/methanol 19:1
(E): Reversed Phase RP8, acetonitrile/water/trifluoroacetic acid = 1:1:0.01

EXAMPLES (co) TO (cq)

Preparation of the starting compounds:

(VI) 1-acetyl-3-(1-ethoxy-methylene)-6-methoxycarbonyl-2-indolinone 8.00 g 1-acetyl-6-methoxycarbonyl-2-indolinone and 17.2 ml triethyl orthoformate are dissolved in 70 ml of acetic anhydride and stirred for 5.5 hrs at 110° C. After cooling the residue is filtered off, washed with ether and vacuum-dried at 100° C.

Yield: 8.80 g (89% of theory)

R_f value: 0.35 (silica gel, petrol ether/methylene chloride/ethylacetate=5:4:1)

Melting point: 187-189° C.

$C_{15}H_{15}NO_5$

Mass spectrum: m/z=290 [m+H]⁺

Preparation of the final compounds:

The following compounds of general formula VI are prepared analogously to the compounds described in WO 01/27081:

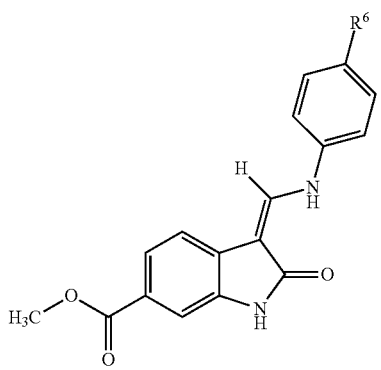

(VI)

| Example | R$^6$ | Formula | Mass spectrum | Melting point [° C.] | R$_f$ value* |
|---|---|---|---|---|---|
| (co) | —NMe—(CO)—CH$_2$—NMe$_2$ | C$_{22}$H$_{24}$N$_4$O$_4$ | 409 [m + H]$^+$ | 250-255 | 0.40 (A) |
| (cp) | —CH$_2$—NMe$_2$ | C$_{20}$H$_{21}$N$_3$O$_3$ | 352 [m + H]$^+$ | 234-238 | 0.35 (A) |
| (cq) | 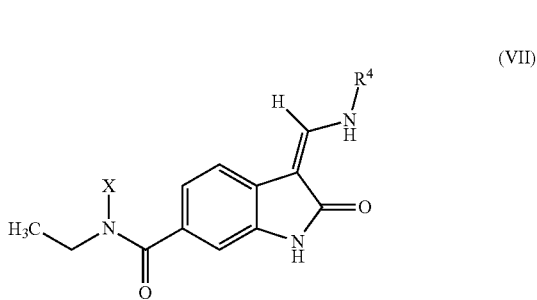 | C$_{25}$H$_{29}$N$_5$O$_4$ | 464 [m + H]$^+$ | 203-207 | 0.45 (A) |

*Solvents:
(A): silica gel, methylene chloride/methanol/ammonia 9:1:0.1

EXAMPLES (cr) TO (cu)

Preparation of the starting compounds:
(VII) 3-(1-hydroxy-methylene)-6-carboxy-2-indolinone 5.00 g 1-acetyl-3-(1-ethoxy-methylene)-6-methoxycarbonyl-2-indolinone (starting material VI) are dissolved in 150 ml of methanol and 86.4 ml of 1N sodium hydroxide solution are added. The mixture is refluxed for 8.5 hrs. After that time 86.4 ml of 1N hydrochloric acid are added. The residue is filtered off and dried at 90° C.

Yield: 2.50 g (71% of theory)
C$_{10}$H$_7$NO$_4$
Mass spectrum: m/z=206 [m+H]$^+$ (VIII) 3-(1-hydroxy-methylene)-6-ethylcarbamoyl-2-indolinone 400 mg 3-(1-hydroxy-methylene)-6-carboxy-2-indolinone (starting material VII), 689 mg TBTU, 291 mg HOBt and 1.35 ml triethylamine are dissolved in 20 ml of dimethylformamide. At 0° C. 1.95 ml of a 2M ethylamine-solution in THF are added and the mixture is stirred for additional 12 hrs at ambient temperature. After that time the solvent is evaporated and the residue is purified over a silica gel column with methylene chloride/ethanol/acetic acid (5:1: 0.01) as eluant.

Yield: 160 mg (35% of theory)
R$_f$ value: 0.20 (silica gel, methylene chloride/ethanol/acetic acid=5:1:0.01)
Melting point: 146-150° C.
C$_{12}$H$_{12}$N$_2$O$_3$
Mass spectrum: m/z=233 [m+H]$^+$ Preparation of the final compounds:
(cr) 3-Z-[1-(4-(N-(4-methyl-piperazin-1-yl-methylcarbonyl)-N-methyl-amino)-anilino)-methylene]-6-ethylcarbamoyl-2-indolinone 160 mg 3-(1-hydroxy-methylene)-6-ethylcarbamoyl-2-indolinone (starting material VIII) and 543 mg N-[(4-methyl-piperazin-1-yl)-methylcarbonyl]-N-methyl-p-phenylendiamine are dissolved in 3 ml of tetrahydrofuran, 506 ml trimethylsilylimidazole are added and the mixture is stirred for 25 minutes at 170° C. in a microwave oven. After cooling the solvent is evaporated and the residue is purified over an aluminum oxide column (activity 2-3) with methylene chloride/ethanol (19:1) as eluant. The residue is recrystallized from ether and vacuum-dried at 80° C.

Yield: 0.17 g (52% of theory),
R$_f$ value: 0.60 (aluminum oxide, methylene chloride/methanol=9:1)
Melting point: 255-260° C.
C$_{26}$H$_{32}$N$_6$O$_3$
Mass spectrum: m/z=477 [m+H]$^+$ The following compounds of general formula VII are prepared analogously to the above compound (ct), following the procedures described in WO 01/27081:

(VII)

| Example | X | R⁴ | Formula | Mass spectrum | Melting point [° C.] | $R_f$-value* |
|---|---|---|---|---|---|---|
| (cs) | —H | 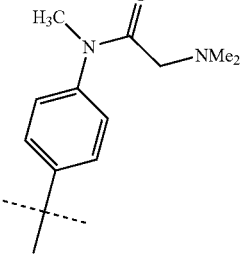 | $C_{23}H_{27}N_5O_3$ | 422 [m + H]⁺ | 280-283 | 0.70 (A) |
| (ct) | —H | 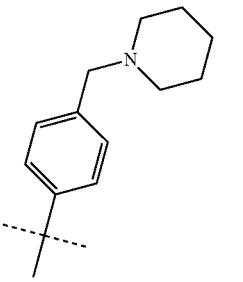 | $C_{24}H_{28}N_4O_2$ | 405 [m + H]⁺ | 245-248 | 0.80 (A) |
| (cu) | —H | 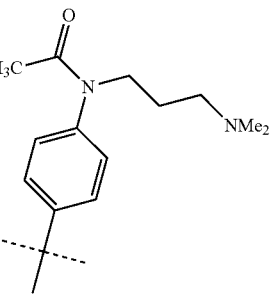 | $C_{25}H_{31}N_5O_3$ | 450 [m + H]⁺ | 130 | 0.40 (B) |

*Solvents:
(A): aluminum oxide, methylene chloride/methanol 9:1
(B): silica gel, methylene chloride/ethanol/ammonia 5:2:0.01

Tautomers, stereoisomers or physiologically acceptable salts of these compounds are also contemplated within the scope of the present invention, and may be obtained using the methods described in WO 01/27081, the content of which is herein incorporated by reference.

A particularly preferred compound is the monoethanesulphonate salt of 3-Z-[1-(4-(N-((4-methyl-piperazin-1-yl)-methylcarbonyl)-N-methyl-amino)-anilino)-1-phenyl-methylene]-6-methoxycarbonyl-2-indolinone, disclosed for example in WO 04/13099, the content of which is incorporated herein by reference.

The metabolites of the compound 3-Z-[1-(4-(N-((4-methyl-piperazin-1-yl)-methylcarbonyl)-N-methyl-amino)-anilino)-1-phenyl-methylene]-6-methoxycarbonyl-2-indolinone-monoethanesulphonate and the prodrugs of this compound or of these metabolites obtained via, for example, chemical or non-chemical derivatization of the entire molecule or of one or more chemical groups on the molecule, are also contemplated compounds within the meaning of the present invention. In this matter, reference is made to WO 04/13099, which describes metabolites and prodrugs of the compound 3-Z-[1-(4-(N-((4-methyl-piperazin-1-yl)-methylcarbonyl)-N-methyl-amino)-anilino)-1-phenyl-methylene]-6-methoxycarbonyl-2-indolinone-monoethanesulphonate.

The following list of specific compounds is illustrative of the present invention, without constituting any limitation of its scope:
(1) 3-Z-(1-anilino-1-phenyl-methylene)-6-ethoxycarbonyl-2-indolinone
(2) 3-Z-[1-(4-nitro-anilino)-1-phenyl-methylene]-6-ethoxycarbonyl-2-indolinone
(3) 3-Z-[1-(4-fluoro-anilino)-1-phenyl-methylene]-6-ethoxy-carbonyl-2-indolinone
(4) 3-Z-[1-(4-chloro-anilino)-1-phenyl-methylene]-6-ethoxy-carbonyl-2-indolinone
(5) 3-Z-[1-(4-iodo-anilino)-1-phenyl-methylene]-6-ethoxy-carbonyl-2-indolinone
(6) 3-Z-[1-(4-cyano-anilino)-1-phenyl-methylene]-6-ethoxy-carbonyl-2-indolinone
(7) 3-Z-[1-(4-methoxy-anilino)-1-phenyl-methylene]-6-ethoxycarbonyl-2-indolinone
(8) 3-Z-[1-(4-ethoxy-anilino)-1-phenyl-methylene]-6-ethoxycarbonyl-2-indolinone
(9) 3-Z-[1-(4-trifluoromethyl-anilino)-1-phenyl-methylene]-6-ethoxycarbonyl-2-indolinone
(10) 3-Z-[1-(4-methyl-anilino)-1-phenyl-methylene]-6-ethoxycarbonyl-2-indolinone
(11) 3-Z-[1-(4-methylmercapto-anilino)-1-phenyl-methylene]-6-ethoxycarbonyl-2-indolinone

(12) 3-Z-[1-(4-aminomethyl-anilino)-1-phenyl-methylene]-6-ethoxycarbonyl-2-indolinone
(13) 3-Z-[1-(4-(isopropylaminomethyl)-anilino)-1-phenyl-methylene]-6-ethoxycarbonyl-2-indolinone
(14) 3-Z-[1-(4-(anilinomethyl)-anilino)-1-phenyl-methylene]-6-ethoxycarbonyl-2-indolinone
(15) 3-Z-[1-(4-(propylaminomethyl)-anilino)-1-phenyl-methylene]-6-ethoxycarbonyl-2-indolinone
(16) 3-Z-[1-(4-(butylaminomethyl)-anilino)-1-phenyl-methylene]-6-ethoxycarbonyl-2-indolinone
(17) 3-Z-[1-(4-(isobutylaminomethyl)-anilino)-1-phenyl-methylene]-6-ethoxycarbonyl-2-indolinone
(18) 3-Z-[1-(4-(cyclohexylaminomethyl)-anilino)-1-phenyl-methylene]-6-ethoxycarbonyl-2-indolinone
(19) 3-Z-[1-(4-(benzylaminomethyl)-anilino)-1-phenyl-methylene]-6-ethoxycarbonyl-2-indolinone
(20) 3-Z-[1-(4-((N-ethyl-N-methyl-amino)-methyl)-anilino)-1-phenyl-methylene]-6-ethoxycarbonyl-2-indolinone
(21) 3-Z-[1-(4-((N-methyl-N-propyl-amino)-methyl)-anilino)-1-phenyl-methylene]-6-ethoxycarbonyl-2-indolinone
(22) 3-Z-[1-(4-((N-isopropyl-N-methyl-amino)-methyl)-anilino)-1-phenyl-methylene]-6-ethoxycarbonyl-2-indolinone
(23) 3-Z-[1-(4-((N-ethyl-N-propyl-amino)-methyl)-anilino)-1-phenyl-methylene]-6-ethoxycarbonyl-2-indolinone
(24) 3-Z-[1-(4-((N-ethyl-N-isopropyl-amino)-methyl)-anilino)-1-phenyl-methylene]-6-ethoxycarbonyl-2-indolinone
(25) 3-Z-[1-(4-(dipropylaminomethyl)-anilino)-1-phenyl-methylene]-6-ethoxycarbonyl-2-indolinone
(26) 3-Z-[1-(4-(diisopropylaminomethyl)-anilino)-1-phenyl-methylene]-6-ethoxycarbonyl-2-indolinone
(27) 3-Z-[1-(4-((N-benzyl-N-ethyl-amino)-methyl)-anilino)-1-phenyl-methylene]-6-ethoxycarbonyl-2-indolinone
(28) 3-Z-[1-(4-(dibenzylaminomethyl)-anilino)-1-phenyl-methylene]-6-ethoxycarbonyl-2-indolinone
(29) 3-Z-[1-(4-(3,6-dihydro-2H-pyridin-1-yl-methyl)-anilino)-1-phenyl-methylene]-6-ethoxycarbonyl-2-indolinone
(30) 3-Z-[1-(4-(3,5-dimethyl-piperidin-1-yl-methyl)-anilino)-1-phenyl-methylene]-6-ethoxycarbonyl-2-indolinone
(31) 3-Z-[1-(4-(azepan-1-yl-methyl)-anilino)-1-phenyl-methylene]-6-ethoxycarbonyl-2-indolinone
(32) 3-Z-[1-(4-(piperazin-1-yl-methyl)-anilino)-1-phenyl-methylene]-6-ethoxycarbonyl-2-indolinone
(33) 3-Z-[1-(4-(morpholin-4-yl-methyl)-anilino)-1-phenyl-methylene]-6-ethoxycarbonyl-2-indolinone
(34) 3-Z-[1-(4-(thiomorpholin-4-yl-methyl)-anilino)-1-phenyl-methylene]-6-ethoxycarbonyl-2-indolinone
(35) 3-Z-[1-(4-(1-oxo-thiomorpholin-4-yl-methyl)-anilino)-1-phenyl-methylene]-6-ethoxycarbonyl-2-indolinone
(36) 3-Z-[1-(4-(1,1-dioxo-thiomorpholin-4-yl-methyl)-anilino)-1-phenyl-methylene]-6-ethoxycarbonyl-2-indolinone
(37) 3-Z-[1-(4-(acetylamino-methyl)-anilino)-1-phenyl-methylene]-6-ethoxycarbonyl-2-indolinone
(38) 3-Z-[1-(4-(2-amino-ethyl)-anilino)-1-phenyl-methylene]-6-ethoxycarbonyl-2-indolinone
(39) 3-Z-[1-(4-(2-methylamino-ethyl)-anilino)-1-phenyl-methylene]-6-ethoxycarbonyl-2-indolinone
(40) 3-Z-[1-(4-(2-ethylamino-ethyl)-anilino)-1-phenyl-methylene]-6-ethoxycarbonyl-2-indolinone
(41) 3-Z-[1-(4-(2-diethylamino-ethyl)-anilino)-1-phenyl-methylene]-6-ethoxycarbonyl-2-indolinone
(42) 3-Z-[1-(4-(2-piperidin-1-yl-ethyl)-anilino)-1-phenyl-methylene]-6-ethoxycarbonyl-2-indolinone
(43) 3-Z-[1-(4-(2-acetylamino-ethyl)-anilino)-1-phenyl-methylene]-6-ethoxycarbonyl-2-indolinone
(44) 3-Z-[1-(4-(3-amino-propyl)-anilino)-1-phenyl-methylene]-6-ethoxycarbonyl-2-indolinone
(45) 3-Z-[1-(4-(3-dimethylamino-propyl)-anilino)-1-phenyl-methylene]-6-ethoxycarbonyl-2-indolinone
(46) 3-Z-[1-(4-(N-aminomethylcarbonyl-N-methyl-amino)-anilino)-1-phenyl-methylene]-6-ethoxycarbonyl-2-indolinone
(47) 3-Z-[1-(4-(N-methylaminomethylcarbonyl-N-methyl-amino)-anilino)-1-phenyl-methylene]-6-ethoxycarbonyl-2-indolinone
(48) 3-Z-[1-(4-(N-ethylaminomethylcarbonyl-N-methyl-amino)-anilino)-1-phenyl-methylene]-6-ethoxycarbonyl-2-indolinone
(49) 3-Z-[1-(4-(N-diethylaminomethylcarbonyl-N-methyl-amino)-anilino)-1-phenyl-methylene]-6-ethoxycarbonyl-2-indolinone
(50) 3-Z-[1-(4-(N-(piperidin-1-yl-methylcarbonyl)-N-methyl-amino)-anilino)-1-phenyl-methylene]-6-ethoxycarbonyl-2-indolinone
(51) 3-Z-[1-(4-(N-(morpholin-4-yl-methylcarbonyl)-N-methyl-amino)-anilino)-1-phenyl-methylene]-6-ethoxycarbonyl-2-indolinone
(52) 3-Z-[1-(4-(N-(piperazin-1-yl-methylcarbonyl)-N-methyl-amino]-anilino)-1-phenyl-methylene]-6-ethoxycarbonyl-2-indolinone
(53) 3-Z-[1-(4-(N-(2-amino-ethylcarbonyl)-N-methyl-amino)-anilino)-1-phenyl-methylene]-6-ethoxycarbonyl-2-indolinone
(54) 3-Z-[1-(4-(N-(2-methylamino-ethylcarbonyl)-N-methyl-amino)-anilino)-1-phenyl-methylene]-6-ethoxycarbonyl-2-indolinone
(55) 3-Z-[1-(4-(N-(2-diethylamino-ethylcarbonyl)-N-methyl-amino)-anilino)-1-phenyl-methylene]-6-ethoxycarbonyl-2-indolinone
(56) 3-Z-[1-(4-(N-acetyl-N-(2-aminoethyl)-amino)-anilino)-1-phenyl-methylene]-6-ethoxycarbonyl-2-indolinone
(57) 3-Z-[1-(4-(N-acetyl-N-(2-methylamino-ethyl)-amino)-anilino)-1-phenyl-methylene]-6-ethoxycarbonyl-2-indolinone
(58) 3-Z-[1-(4-(N-acetyl-N-(2-methylamino-propyl)-amino)-anilino)-1-phenyl-methylene]-6-ethoxycarbonyl-2-indolinone
(59) 3-Z-[1-(4-(N-acetyl-N-(2-piperidin-1-yl-ethyl)-amino)-anilino)-1-phenyl-methylene]-6-ethoxycarbonyl-2-indolinone
(60) 3-Z-[1-(4-(N-acetyl-N-(aminocarbonylmethyl)-amino)-anilino)-1-phenyl-methylene]-6-ethoxycarbonyl-2-indolinone
(61) 3-Z-[1-(4-(N-acetyl-N-(dimethylaminocarbonylmethyl)-amino)-anilino)-1-phenyl-methylene]-6-ethoxycarbonyl-2-indolinone
(62) 3-Z-[1-(4-(N-acetyl-N-(piperidin-1-yl-carbonylmethyl)-amino)-anilino)-1-phenyl-methylene]-6-ethoxycarbonyl-2-indolinone
(63) 3-Z-[1-(4-(N-methyl-N-(aminocarbonyl)-amino)-anilino)-1-phenyl-methylene]-6-ethoxycarbonyl-2-indolinone
(64) 3-Z-[1-(4-(N-methyl-N-(methylaminocarbonyl)-amino)-anilino)-1-phenyl-methylene]-6-ethoxycarbonyl-2-indolinone

(65) 3-Z-[1-(4-(N-methyl-N-(dimethylaminocarbonyl)-amino)-anilino)-1-phenyl-methylene]-6-ethoxycarbonyl-2-indolinone
(66) 3-Z-[1-(4-(N-methyl-N-(piperidin-1-yl-carbonyl)-amino)-anilino)-1-phenyl-methylene]-6-ethoxycarbonyl-2-indolinone
(67) 3-Z-[1-(4-(N-(2-aminoethyl)-N-methylsulphonyl-amino)-anilino)-1-phenyl-methylene]-6-ethoxycarbonyl-2-indolinone
(68) 3-Z-[1-(4-(N-(2-methylamino-ethyl)-N-methylsulphonyl-amino)-anilino)-1-phenyl-methylene]-6-ethoxycarbonyl-2-indolinone
(69) 3-Z-[1-(4-(N-(2-ethylamino-ethyl)-N-methylsulphonyl-amino)-anilino)-1-phenyl-methylene]-6-ethoxycarbonyl-2-indolinone
(70) 3-Z-[1-(4-(N-(2-diethylamino-ethyl)-N-methylsulphonyl-amino)-anilino)-1-phenyl-methylene]-6-ethoxycarbonyl-2-indolinone
(71) 3-Z-[1-(4-(N-(2-pyrrolidin-1-yl-ethyl)-N-methylsulphonyl-amino)-anilino)-1-phenyl-methylene]-6-ethoxycarbonyl-2-indolinone
(72) 3-Z-[1-(4-(N-(2-piperidin-1-yl-ethyl)-N-methylsulphonyl-amino)-anilino)-1-phenyl-methylene]-6-ethoxycarbonyl-2-indolinone
(73) 3-Z-[1-(4-(N-(2-piperazin-1-yl-ethyl)-N-methylsulphonyl-amino)-anilino)-1-phenyl-methylene]-6-ethoxycarbonyl-2-indolinone
(74) 3-Z-[1-(4-(N-(2-(morpholin-4-yl)-ethyl)-N-methylsulphonyl-amino)-anilino)-1-phenyl-methylene]-6-ethoxycarbonyl-2-indolinone
(75) 3-Z-[1-(4-(N-(aminocarbonylmethyl)-N-methylsulphonyl-amino)-anilino)-1-phenyl-methylene]-6-ethoxycarbonyl-2-indolinone
(76) 3-Z-[1-(4-(N-(methylaminocarbonylmethyl)-N-methylsulphonyl-amino)-anilino)-1-phenyl-methylene]-6-ethoxycarbonyl-2-indolinone
(77) 3-Z-[1-(4-(N-(ethylaminocarbonylmethyl)-N-methylsulphonyl-amino)-anilino)-1-phenyl-methylene]-6-ethoxycarbonyl-2-indolinone
(78) 3-Z-[1-(4-(N-(N-(2-dimethylamino-ethyl)-N-methyl-amino)-carbonylmethyl)-N-methylsulphonyl-amino)-anilino)-1-phenyl-methylene]-6-ethoxycarbonyl-2-indolinone
(79) 3-Z-[1-(4-(N-(diethylaminocarbonylmethyl)-N-methylsulphonyl-amino)-anilino)-1-phenyl-methylene]-6-ethoxycarbonyl-2-indolinone
(80) 3-Z-[1-(4-(N-(pyrrolidin-1-yl-carbonylmethyl)-N-methyl-sulphonyl-amino)-anilino)-1-phenyl-methylene]-6-ethoxycarbonyl-2-indolinone
(81) 3-Z-[1-(4-(N-(piperidin-1-yl-carbonylmethyl)-N-methylsulphonyl-amino)-anilino)-1-phenyl-methylene]-6-ethoxycarbonyl-2-indolinone
(82) 3-Z-[1-(4-(N-(piperazin-1-yl-carbonylmethyl)-N-methylsulphonyl-amino)-anilino)-1-phenyl-methylene]-6-ethoxycarbonyl-2-indolinone
(83) 3-Z-[1-(4-(N-((morpholin-4-yl)-carbonylmethyl)-N-methylsulphonyl-amino)-anilino)-1-phenyl-methylene]-6-ethoxycarbonyl-2-indolinone
(84) 3-Z-[1-(4-(2-dimethylamino-ethoxy)-anilino)-1-phenyl-methylene]-6-ethoxycarbonyl-2-indolinone
(85) 3-Z-[1-(4-(3-dimethylamino-propoxy)-anilino)-1-phenyl-methylene]-6-ethoxycarbonyl-2-indolinone
(86) 3-Z-[1-(4-(aminocarbonylmethyl)-anilino)-1-phenyl-methylene]-6-ethoxycarbonyl-2-indolinone
(87) 3-Z-[1-(4-(2-aminocarbonyl-ethyl)-anilino)-1-phenyl-methylene]-6-ethoxycarbonyl-2-indolinone
(88) 3-Z-[1-(4-(pyridin-2-yl)-anilino)-1-phenyl-methylene]-6-ethoxycarbonyl-2-indolinone
(89) 3-Z-[1-(4-(pyridine-3-yl)-anilino)-1-phenyl-methylene]-6-ethoxycarbonyl-2-indolinone
(90) 3-Z-[1-(4-(pyridin-4-yl)-anilino)-1-phenyl-methylene]-6-ethoxycarbonyl-2-indolinone
(91) 3-Z-[1-(4-(N-acetyl-N-methyl-amino)-anilino)-1-phenyl-methylene]-6-ethoxycarbonyl-2-indolinone
(92) 3-Z-[1-(4-(N-ethylcarbonyl-N-(dimethylaminocarbonyl-methyl)-amino)-anilino)-1-phenyl-methylene]-6-ethoxycarbonyl-2-indolinone
(93) 3-Z-[1-(carbamoylmethyl-anilino)-1-phenyl-methylene]-6-ethoxycarbonyl-2-indolinone
(94) 3-Z-[1-(4-dimethylcarbamoylmethyl-anilino)-1-phenyl-methylene]-6-ethoxycarbonyl-2-indolinone
(95) 3-Z-[1-(4-(piperidin-1-yl-methyl)-anilino)-methylene]-6-ethoxycarbonyl-2-indolinone
(96) 3-Z-[1-(4-(piperidin-1-yl-methyl)-anilino)-propylidene]-6-ethoxycarbonyl-2-indolinone
(97) 3-Z-[1-(4-(piperidin-1-yl-methyl)-anilino)-butylidene]-6-ethoxycarbonyl-2-indolinone
(98) 3-Z-[1-(4-(N-(3-dimethylamino-propyl)-N-acetyl-amino)-anilino)-methylene]-6-ethoxycarbonyl-2-indolinone
(99) 3-Z-[1-(4-(N-(3-dimethylamino-propyl)-N-acetyl-amino)-anilino)-ethylidene]-6-ethoxycarbonyl-2-indolinone
(100) 3-Z-[1-(4-(N-(3-dimethylamino-propyl)-N-acetyl-amino)-anilino)-propylidene]-6-ethoxycarbonyl-2-indolinone
(101) 3-Z-[1-(4-(N-(3-dimethylamino-propyl)-N-acetyl-amino)-anilino)-butylidene]-6-ethoxycarbonyl-2-indolinone
(102) 3-Z-[1-(4-(N-(2-dimethylamino-ethyl)-N-methylsulphonyl-amino)-anilino)-methylene]-6-ethoxycarbonyl-2-indolinone
(103) 3-Z-[1-(4-(N-(2-dimethylamino-ethyl)-N-methylsulphonyl-amino)-anilino)-propylidene]-6-ethoxycarbonyl-2-indolinone
(104) 3-Z-[1-(4-(N-(2-dimethylamino-ethyl)-N-methylsulphonyl-amino)-anilino)-butylidene]-6-ethoxycarbonyl-2-indolinone
(105) 3-Z-[1-(4-tetrazol-5-yl-anilino)-methylene]-6-ethoxycarbonyl-2-indolinone
(106) 3-Z-[1-(4-tetrazol-5-yl-anilino)-ethylidene]-6-ethoxycarbonyl-2-indolinone
(107) 3-Z-[1-(4-tetrazol-5-yl-anilino)-propylidene]-6-ethoxycarbonyl-2-indolinone
(108) 3-Z-[1-(4-tetrazol-5-yl-anilino)-butylidene]-6-ethoxycarbonyl-2-indolinone
(109) 3-Z-[1-(4-carboxy-anilino)-methylene]-6-ethoxycarbonyl-2-indolinone
(110) 3-Z-[1-(4-carboxy-anilino)-propylidene]-6-ethoxycarbonyl-2-indolinone
(111) 3-Z-[1-(4-carboxy-anilino)-butylidene]-6-ethoxycarbonyl-2-indolinone
(112) 3-Z-[1-(4-(N-(3-dimethylamino-propionyl)-N-dimethylaminocarbonylmethyl-amino)-anilino)-1-phenyl-methylene]-6-ethoxycarbonyl-2-indolinone
(113) 3-Z-[1-(4-(N-(4-dimethylamino-butyryl)-N-dimethyl-aminocarbonylmethyl-amino)-anilino)-1-phenyl-methylene]-6-ethoxycarbonyl-2-indolinone
(114) 3-Z-[1-(4-(N-dimethylaminocarbonylmethyl-N-(2-dimethylamino-ethylsulphonyl)-amino)-anilino)-1-phenyl-methylene]-6-ethoxycarbonyl-2-indolinone (115) 3-Z-[1-(4-(N-dimethylaminocarbonylmethyl-N-(3-dimethylamino-propylsulphonyl)-amino)-anilino)-1-phenyl-methylene]-6-ethoxycarbonyl-2-indolinone
(116) 3-Z-[1-(4-((2-hydroxy-ethyl)-amino-methyl)-anilino)-1-phenyl-methylene]-6-ethoxycarbonyl-2-indolinone
(117) 3-Z-[1-(4-((2-methoxy-ethyl)-amino-methyl)-anilino)-1-phenyl-methylene]-6-ethoxycarbonyl-2-indolinone
(118) 3-Z-[1-(4-((2-dimethylamino-ethyl)-amino-methyl)-anilino)-1-phenyl-methylene]-6-ethoxycarbonyl-2-indolinone
(119) 3-Z-[1-(4-((3-dimethylamino-propyl)-amino-methyl)-anilino)-1-phenyl-methylene]-6-ethoxycarbonyl-2-indolinone
(120) 3-Z-[1-(4-((N-tert.butoxycarbonyl-2-amino-ethyl)-amino-methyl)-anilino)-1-phenyl-methylene]-6-ethoxycarbonyl-2-indolinone
(121) 3-Z-[1-(4-((N-tert.butoxycarbonyl-3-amino-propyl)-amino-methyl)-anilino)-1-phenyl-methylene]-6-ethoxycarbonyl-2-indolinone
(122) 3-Z-[1-(4-((2-amino-ethyl)-amino-methyl)-anilino)-1-phenyl-methylene]-6-ethoxycarbonyl-2-indolinone
(123) 3-Z-[1-(4-((3-amino-propyl)-amino-methyl)-anilino)-1-phenyl-methylene]-6-ethoxycarbonyl-2-indolinone
(124) 3-Z-[1-(4-((2-acetylamino-ethyl)-amino-methyl)-anilino)-1-phenyl-methylene]-6-ethoxycarbonyl-2-indolinone
(125) 3-Z-[1-(4-((3-acetylamino-propyl)-amino-methyl)-anilino)-1-phenyl-methylene]-6-ethoxycarbonyl-2-indolinone
(126) 3-Z-[1-(4-((2-methylsulphonylamino-ethyl)-amino-methyl)-anilino)-1-phenyl-methylene]-6-ethoxycarbonyl-2-indolinone
(127) 3-Z-[1-(4-((3-methylsulphonylamino-propyl)-amino-methyl)-anilino)-1-phenyl-methylene]-6-ethoxycarbonyl-2-indolinone
(128) 3-Z-[1-(4-(N-(N-tert.butoxycarbonyl-2-amino-ethyl)-N-methyl-amino-methyl)-anilino)-1-phenyl-methylene]-6-ethoxycarbonyl-2-indolinone
(129) 3-Z-[1-(4-(N-(2-amino-ethyl)-N-methyl-amino-methyl)-anilino)-1-phenyl-methylene]-6-ethoxycarbonyl-2-indolinone
(130) 3-Z-[1-(4-(N-(2-acetylamino-ethyl)-N-methyl-amino-methyl)-anilino)-1-phenyl-methylene]-6-ethoxycarbonyl-2-indolinone
(131) 3-Z-[1-(4-(N-(2-methylsulphonylamino-ethyl)-N-methyl-amino-methyl)-anilino)-1-phenyl-methylene]-6-ethoxycarbonyl-2-indolinone
(132) 3-Z-[1-(4-(carboxymethyl-amino-methyl)-anilino)-1-phenyl-methylene]-6-ethoxycarbonyl-2-indolinone
(133) 3-Z-[1-(4-(ethoxycarbonylmethyl-amino-methyl)-anilino)-1-phenyl-methylene]-6-ethoxycarbonyl-2-indolinone
(134) 3-Z-[1-(4-(carbamoylmethyl-amino-methyl)-anilino)-1-phenyl-methylene]-6-ethoxycarbonyl-2-indolinone
(135) 3-Z-[1-(4-(dimethylcarbamoyl-methyl-amino-methyl)-anilino)-1-phenyl-methylene]-6-ethoxycarbonyl-2-indolinone
(136) 3-Z-[1-(4-(methylcarbamoyl-methyl-amino-methyl)-anilino)-1-phenyl-methylene]-6-ethoxycarbonyl-2-indolinone
(137) 3-Z-[1-(4-(N-dimethylaminomethylcarbonyl-N-methyl-amino)-3-amino-anilino)-1-phenyl-methylene]-6-ethoxycarbonyl-2-indolinone
(138) 3-Z-[1-(4-(N-dimethylaminomethylcarbonyl-N-methyl-amino)-3-nitro-anilino)-1-phenyl-methylene]-6-ethoxycarbonyl-2-indolinone
(139) 3-Z-[1-(4-(N-dimethylaminomethylcarbonyl-N-methyl-amino)-3-acetylamino-anilino)-1-phenyl-methylene]-6-ethoxycarbonyl-2-indolinone
(140) 3-Z-[1-(4-(N-dimethylaminomethylcarbonyl-N-methyl-amino)-3-methylsulphonylamino-anilino)-1-phenyl-methylene]-6-ethoxycarbonyl-2-indolinone
(141) 3-Z-[1-(4-(N-dimethylaminomethylcarbonyl-N-methyl-amino)-3-cyano-anilino)-1-phenyl-methylene]-6-ethoxycarbonyl-2-indolinone
(142) 3-Z-[1-(4-(N-dimethylaminomethylcarbonyl-N-methyl-amino)-3-hydroxy-anilino)-1-phenyl-methylene]-6-ethoxycarbonyl-2-indolinone
(143) 3-Z-[1-(4-(N-dimethylaminomethylcarbonyl-N-methyl-amino)-3-methoxy-anilino)-1-phenyl-methylene]-6-ethoxycarbonyl-2-indolinone
(144) 3-Z-[1-(4-(N-dimethylaminomethylcarbonyl-N-methyl-amino)-3-ethoxycarbonyl-anilino)-1-phenyl-methylene]-6-ethoxycarbonyl-2-indolinone
(145) 3-Z-[1-(4-(N-dimethylaminomethylcarbonyl-N-methyl-amino)-3-carboxy-anilino)-1-phenyl-methylene]-6-ethoxycarbonyl-2-indolinone
(146) 3-Z-[1-(4-(N-dimethylaminomethylcarbonyl-N-methyl-amino)-3-carbamoyl-anilino)-1-phenyl-methylene]-6-ethoxycarbonyl-2-indolinone
(147) 3-Z-[1-(4-(N-dimethylaminomethylcarbonyl-N-methyl-amino)-3-chloro-anilino)-1-phenyl-methylene]-6-ethoxycarbonyl-2-indolinone
(148) 3-Z-[1-(4-(N-dimethylaminomethylcarbonyl-N-methyl-amino)-3-fluoro-anilino)-1-phenyl-methylene]-6-ethoxycarbonyl-2-indolinone
(149) 3-Z-[1-(4-(N-dimethylaminomethylcarbonyl-N-methyl-amino)-3-bromo-anilino)-1-phenyl-methylene]-6-ethoxycarbonyl-2-indolinone
(150) 3-Z-[1-(4-(N-dimethylaminomethylcarbonyl-N-methyl-amino)-3-methyl-anilino)-1-phenyl-methylene]-6-ethoxycarbonyl-2-indolinone
(151) 3-Z-[1-(4-(N-dimethylaminomethylcarbonyl-N-methyl-amino)-3-trifluoromethyl-anilino)-1-phenyl-methylene]-6-ethoxycarbonyl-2-indolinone
(152) 3-Z-[1-(4-(N-dimethylaminomethylcarbonyl-N-methyl-amino)-3,5-dibromo-anilino)-1-phenyl-methylene]-6-ethoxycarbonyl-2-indolinone
(153) 3-Z-[1-(4-(N-dimethylaminomethylcarbonyl-N-methyl-amino)-3,5-dichloro-anilino)-1-phenyl-methylene]-6-ethoxycarbonyl-2-indolinone
(154) 3-Z-[1-(4-(dimethylaminomethyl)-3-amino-anilino)-1-phenyl-methylene]-6-ethoxycarbonyl-2-indolinone
(155) 3-Z-[1-(4-(dimethylaminomethyl)-3-nitro-anilino)-1-phenyl-methylene]-6-ethoxycarbonyl-2-indolinone
(156) 3-Z-[1-(4-(dimethylaminomethyl)-3-acetylamino-anilino)-1-phenyl-methylene]-6-ethoxycarbonyl-2-indolinone
(157) 3-Z-[1-(4-(dimethylaminomethyl)-3-(methylsulphonylamino)-anilino)-1-phenyl-methylene]-6-ethoxycarbonyl-2-indolinone
(158) 3-Z-[1-(4-(dimethylaminomethyl)-3-cyano-anilino)-1-phenyl-methylene]-6-ethoxycarbonyl-2-indolinone
(159) 3-Z-[1-(4-(dimethylaminomethyl)-3-hydroxy-anilino)-1-phenyl-methylene]-6-ethoxycarbonyl-2-indolinone
(160) 3-Z-[1-(4-(dimethylaminomethyl)-3-methoxy-anilino)-1-phenyl-methylene]-6-ethoxycarbonyl-2-indolinone
(161) 3-Z-[1-(4-(dimethylaminomethyl)-3-(ethoxycarbonyl)-anilino)-1-phenyl-methylene]-6-ethoxycarbonyl-2-indolinone (162) 3-Z-[1-(4-(dimethylaminomethyl)-3-carboxy-anilino)-1-phenyl-methylene]-6-ethoxycarbonyl-2-indolinone
(163) 3-Z-[1-(4-(dimethylaminomethyl)-3-carbamoyl-anilino)-1-phenyl-methylene]-6-ethoxycarbonyl-2-indolinone
(164) 3-Z-[1-(4-(dimethylaminomethyl)-3-chloro-anilino)-1-phenyl-methylene]-6-ethoxycarbonyl-2-indolinone
(165) 3-Z-[1-(4-(dimethylaminomethyl)-3-fluoro-anilino)-1-phenyl-methylene]-6-ethoxycarbonyl-2-indolinone
(166) 3-Z-[1-(4-(dimethylaminomethyl)-3-bromo-anilino)-1-phenyl-methylene]-6-ethoxycarbonyl-2-indolinone
(167) 3-Z-[1-(4-(dimethylaminomethyl)-3-methyl-anilino)-1-phenyl-methylene]-6-ethoxycarbonyl-2-indolinone
(168) 3-Z-[1-(4-(dimethylaminomethyl)-3-trifluoromethyl-anilino)-1-phenyl-methylene]-6-ethoxycarbonyl-2-indolinone
(169) 3-Z-[1-(4-(dimethylaminomethyl)-3,5-dibromo-anilino)-1-phenyl-methylene]-6-ethoxycarbonyl-2-indolinone
(170) 3-Z-[1-(4-(dimethylaminomethyl)-3,5-dichloro-anilino)-1-phenyl-methylene]-6-ethoxycarbonyl-2-indolinone
(171) 3-Z-[1-(4-(N-((4-methyl-piperazin-1-yl)-methylcarbonyl)-N-methyl-amino)-anilino)-1-phenyl-methylene]-6-ethoxycarbonyl-2-indolinone
(172) 3-Z-[1-(4-(N-(imidazo-1-yl-methylcarbonyl)-N-methyl-amino)-anilino)-1-phenyl-methylene]-6-ethoxycarbonyl-2-indolinone
(173) 3-Z-[1-(4-(N-(phthalimido-2-yl-methylcarbonyl)-N-methyl-amino)-anilino)-1-phenyl-methylene]-6-ethoxycarbonyl-2-indolinone
(174) 3-Z-[1-(4-(N-aminomethylcarbonyl-N-methyl-amino)-anilino)-1-phenyl-methylene]-6-ethoxycarbonyl-2-indolinone
(175) 3-Z-[1-(4-(N-acetylaminomethylcarbonyl-N-methyl-amino)-anilino)-1-phenyl-methylene]-6-ethoxycarbonyl-2-indolinone
(176) 3-Z-[1-(4-(N-methylsulphonylaminomethylcarbonyl-N-methyl-amino)-anilino)-1-phenyl-methylene]-6-ethoxycarbonyl-2-indolinone
(177) 3-Z-[1-(4-(N-((N-(2-methoxyethyl)-N-methyl-amino)-methylcarbonyl)-N-methyl-amino)-anilino)-1-phenyl-methylene]-6-ethoxycarbonyl-2-indolinone
(178) 3-Z-[1-(4-(N-((N-(2-dimethylaminoethyl)-N-methyl-amino)-methylcarbonyl)-N-methyl-amino)-anilino)-1-phenyl-methylene]-6-ethoxycarbonyl-2-indolinone
(179) 3-Z-[1-(4-(N-((di-(2-hydroxyethyl)-amino)-methylcarbonyl)-N-methyl-amino)-anilino)-1-phenyl-methylene]-6-ethoxycarbonyl-2-indolinone
(180) 3-Z-[1-(4-(N-dimethylaminomethylcarbonyl-N-methyl-amino)-anilino)-methylene]-6-ethoxycarbonyl-2-indolinone
(181) 3-Z-[1-(4-(N-dimethylaminomethylcarbonyl-N-methyl-amino)-anilino)-ethylidene]-6-ethoxycarbonyl-2-indolinone
(182) 3-Z-[1-(4-(N-dimethylaminomethylcarbonyl-N-methyl-amino)-anilino)-propylidene]-6-ethoxycarbonyl-2-indolinone
(183) 3-Z-[1-(4-(N-dimethylaminomethylcarbonyl-N-methyl-amino)-anilino)-butylidene]-6-ethoxycarbonyl-2-indolinone
(184) 3-Z-[1-(4-(dimethylaminomethyl)-anilino)-methylene]-6-ethoxycarbonyl-2-indolinone
(185) 3-Z-[1-(4-(dimethylaminomethyl)-anilino)-ethylidene]-6-ethoxycarbonyl-2-indolinone
(186) 3-Z-[1-(4-(dimethylaminomethyl)-anilino)-propylidene]-6-ethoxycarbonyl-2-indolinone
(187) 3-Z-[1-(4-(dimethylaminomethyl)-anilino)-butylidene]-6-ethoxycarbonyl-2-indolinone
(188) 3-Z-[1-(4-(N-dimethylaminocarbonylmethyl-amino)-anilino)-1-phenyl-methylene]-6-ethoxycarbonyl-2-indolinone
(189) 3-Z-[1-(4-(N-(3-dimethylamino-propyl)-N-acetyl-amino)-anilino)-1-phenyl-methylene]-6-ethoxycarbonyl-2-indolinone
(190) 3-Z-[1-(4-((imidazolidin-2,4-dion-5-ylidene)-methyl)-anilino)-1-phenyl-methylene]-6-ethoxycarbonyl-2-indolinone
(191) 3-Z-[1-(4-(N-((2-dimethylamino-ethyl)-carbonyl)-N-methyl-amino)-anilino)-1-phenyl-methylene]-6-ethoxycarbonyl-2-indolinone
(192) 3-Z-[1-(4-(N-tert.butoxycarbonyl-aminomethyl)-anilino)-1-phenyl-methylene]-6-ethoxycarbonyl-2-indolinone
(193) 3-Z-[1-(4-(2-oxo-pyrrolidin-1-yl-methyl)-anilino)-1-phenyl-methylene]-6-ethoxycarbonyl-2-indolinone
(194) 3-Z-[1-(4-(N-aminocarbonylmethyl-N-methylsulphonyl-amino)-anilino)-1-phenyl-methylene]-6-ethoxycarbonyl-2-indolinone
(195) 3-Z-[1-(4-(N-cyanomethyl-N-methylsulphonyl-amino)-anilino)-1-phenyl-methylene]-6-ethoxycarbonyl-2-indolinone
(196) 3-Z-[1-(4-(2-(imidazol-4-yl)-ethyl)-anilino)-1-phenyl-methylene]-6-ethoxycarbonyl-2-indolinone
(197) 3-Z-[1-(4-((2-(N-benzyl-N-methyl-amino)-ethyl)-N-methylsulphonyl-amino)-anilino)-1-phenyl-methylene]-6-ethoxycarbonyl-2-indolinone
(198) 3-Z-[1-(4-cyclohexylamino-anilino)-1-phenyl-methylene]-6-ethoxycarbonyl-2-indolinone
(199) 3-Z-[1-(4-(imidazol-1-yl-methyl)-anilino)-1-phenyl-methylene]-6-ethoxycarbonyl-2-indolinone
(200) 3-Z-[1-(4-(imidazol-1-yl-methyl)-anilino)-1-phenyl-methylene]-6-ethoxycarbonyl-2-indolinone
(201) 3-Z-[1-(N-methyl-piperidine-4-yl-amino)-1-phenyl-methylene]-6-ethoxycarbonyl-2-indolinone
(202) 3-Z-[1-(4-(imidazol-4-yl-methyl)-anilino)-1-phenyl-methylene]-6-ethoxycarbonyl-2-indolinone
(203) 3-Z-[1-(4-((4-hydroxy-piperidin-1-yl)-methyl)-anilino)-1-phenyl-methylene]-6-ethoxycarbonyl-2-indolinone
(204) 3-Z-[1-(4-((4-methoxy-piperidin-1-yl)-methyl)-anilino)-1-phenyl-methylene]-6-ethoxycarbonyl-2-indolinone
(205) 3-Z-[1-(4-benzyl-anilino)-1-phenyl-methylene]-6-ethoxycarbonyl-2-indolinone
(206) 3-Z-[1-(4-(N-(3-trifluoroacetylamino-propyl)-N-methylsulphonyl-amino)-anilino)-1-phenyl-methylene]-6-ethoxycarbonyl-2-indolinone
(207) 3-Z-[1-(4-(4-tert.butoxycarbonyl-piperazin-1-yl-methyl)-anilino)-1-phenyl-methylene]-6-ethoxycarbonyl-2-indolinone
(208) 3-Z-[1-(4-(1-methyl-imidazol-2-yl)-anilino)-1-phenyl-methylene]-6-ethoxycarbonyl-2-indolinone
(209) 3-Z-[1-(4-(1-methyl-imidazol-2-yl)-anilino)-1-phenyl-methylene]-6-ethoxycarbonyl-2-indolinone
(210) 3-Z-[1-(4-(N-(2-dimethylamino-ethyl)-N-methylsulphonyl-amino)-3-amino-anilino)-1-phenyl-methylene]-6-ethoxycarbonyl-2-indolinone
(211) 3-Z-[1-(4-((3-(N-benzyl-N-methyl-amino)-propyl)-N-methylsulphonyl-amino)-anilino)-1-phenyl-methylene]-6-ethoxycarbonyl-2-indolinone (212) 3-Z-[1-(4-(N-(2-dimethylamino-ethyl)-N-acetyl-amino)-anilino)-1-phenyl-methylene]-6-ethoxycarbonyl-2-indolinone
(213) 3-Z-[1-(4-(N-(2-dimethylamino-ethyl)-N-butyryl-amino)-anilino)-1-phenyl-methylene]-6-ethoxycarbonyl-2-indolinone
(214) 3-Z-[1-(4-(N-(2-dimethylamino-ethyl)-N-isobutyryl-amino)-anilino)-1-phenyl-methylene]-6-ethoxycarbonyl-2-indolinone
(215) 3-Z-[1-(4-(N-(2-dimethylamino-ethyl)-N-benzoyl-amino)-anilino)-1-phenyl-methylene]-6-ethoxycarbonyl-2-indolinone
(216) 3-Z-[1-(4-(N-(2-dimethylamino-ethyl)-N-acetyl-amino)-3-amino-anilino)-1-phenyl-methylene]-6-ethoxycarbonyl-2-indolinone
(217) 3-Z-[1-(4-(4-hydroxymethyl-piperidin-1-yl-methyl)-anilino)-1-phenyl-methylene]-6-ethoxycarbonyl-2-indolinone
(218) 3-Z-[1-(4-(2-(4-hydroxy-piperidin-1-yl)-ethyl)-anilino)-1-phenyl-methylene]-6-ethoxycarbonyl-2-indolinone
(219) 3-Z-[1-(4-(N-(2-dimethylamino-ethyl)-N-propylsulphonyl-amino)-anilino)-1-phenyl-methylene]-6-ethoxycarbonyl-2-indolinone
(220) 3-Z-[1-(4-(N-(2-dimethylamino-ethyl)-N-butylsulphonyl-amino)-anilino)-1-phenyl-methylene]-6-ethoxycarbonyl-2-indolinone
(221) 3-Z-[1-(4-(N-(2-dimethylamino-ethyl)-N-phenylsulphonyl-amino)-anilino)-1-phenyl-methylene]-6-ethoxycarbonyl-2-indolinone
(222) 3-Z-[1-(4-(N-(2-dimethylamino-ethyl)-N-benzylsulphonyl-amino)-anilino)-1-phenyl-methylene]-6-ethoxycarbonyl-2-indolinone
(223) 3-Z-[1-(4-((imidazolidin-2,4-dion-5-yl)-methyl)-anilino)-1-phenyl-methylene]-6-ethoxycarbonyl-2-indolinone
(224) 3-Z-[1-(4-((3-hydroxy-pyrrolidin-1-yl)-methyl)-anilino)-1-phenyl-methylene]-6-ethoxycarbonyl-2-indolinone
(225) 3-Z-[1-(4-(cyclohexylyl-methyl)-anilino)-1-phenyl-methylene]-6-ethoxycarbonyl-2-indolinone
(226) 3-Z-[1-(4-(cyclohexyl-carbonyl)-anilino)-1-phenyl-methylene]-6-ethoxycarbonyl-2-indolinone
(227) 3-Z-[1-(4-diethylaminomethyl-anilino)-1-phenyl-methylene]-6-ethoxycarbonyl-2-indolinone
(228) 3-Z-[1-(4-(N-(n-hexyl)-N-methyl-aminomethyl)-anilino)-1-phenyl-methylene]-6-ethoxycarbonyl-2-indolinone
(229) 3-Z-[1-(4-(N-(2-dimethylamino-ethyl)-N-(furan-2-carbonyl)-amino)-anilino)-1-phenyl-methylene]-6-ethoxycarbonyl-2-indolinone
(230) 3-Z-[1-(4-(N-(2-dimethylamino-ethyl)-N-(2-methoxy-benzoyl)-amino)-anilino)-1-phenyl-methylene]-6-ethoxycarbonyl-2-indolinone
(231) 3-Z-[1-(4-(N-(2-dimethylamino-ethyl)-N-(pyridine-3-carbonyl)-amino)-anilino)-1-phenyl-methylene]-6-ethoxycarbonyl-2-indolinone
(232) 3-Z-[1-(4-(N-(2-dimethylamino-ethyl)-N-(phenyl-acetyl)-amino)-anilino)-1-phenyl-methylene]-6-ethoxycarbonyl-2-indolinone
(233) 3-Z-[1-(4-(imidazol-2-yl)-anilino)-1-phenyl-methylene]-6-ethoxycarbonyl-2-indolinone
(234) 3-Z-[1-(4-(1-ethyl-imidazol-2-yl)-anilino)-1-phenyl-methylene]-6-ethoxycarbonyl-2-indolinone
(235) 3-Z-[1-(4-(1-benzyl-imidazol-2-yl)-anilino)-1-phenyl-methylene]-6-ethoxycarbonyl-2-indolinone
(236) 3-Z-[1-(4-(N-(2-dimethylamino-ethyl)-N-isopropyl-sulphonyl-amino)-anilino)-1-phenyl-methylene]-6-ethoxycarbonyl-2-indolinone
(237) 3-Z-[1-(4-(N-((4-benzyl-piperazin-1-yl)-methylcarbonyl)-N-methyl-amino)-anilino)-1-phenyl-methylene]-6-ethoxycarbonyl-2-indolinone
(238) 3-Z-[1-(4-(N-(pyrrolidin-1-yl-methylcarbonyl)-N-methyl-amino)-anilino)-1-phenyl-methylene]-6-ethoxycarbonyl-2-indolinone
(239) 3-Z-[1-(4-(N-(2-dimethylamino-ethyl)-N-acetyl-amino)-3-bromo-anilino)-1-phenyl-methylene]-6-ethoxycarbonyl-2-indolinone
(240) 3-Z-[1-(4-(5-methyl-imidazol-4-yl)-anilino)-1-phenyl-methylene]-6-ethoxycarbonyl-2-indolinone
(241) 3-Z-[1-(4-(N-((2-dimethylamino-ethyl)-carbonyl)-N-isopropyl-amino)-anilino)-1-phenyl-methylene]-6-ethoxycarbonyl-2-indolinone
(242) 3-Z-[1-(4-(N-((2-dimethylamino-ethyl)-carbonyl)-N-benzyl-amino)-anilino)-1-phenyl-methylene]-6-ethoxycarbonyl-2-indolinone
(243) 3-Z-[1-(4-(N-butyl-N-tert.butoxycarbonyl-aminomethyl)-anilino)-1-phenyl-methylene]-6-ethoxycarbonyl-2-indolinone
(244) 3-Z-[1-(4-(N-((N-aminocarbonylmethyl-N-methyl-amino)-methylcarbonyl)-N-methyl-amino)-anilino)-1-phenyl-methylene]-6-ethoxycarbonyl-2-indolinone
(245) 3-Z-[1-(4-(N-((N-benzyl-N-methyl-amino)-methylcarbonyl)-N-methyl-amino)-anilino)-1-phenyl-methylene]-6-ethoxycarbonyl-2-indolinone
(246) 3-Z-[1-(4-(N-(di-(2-methoxyethyl)-amino-methylcarbonyl)-N-methyl-amino)-anilino)-1-phenyl-methylene]-6-ethoxycarbonyl-2-indolinone
(247) 3-Z-[1-(4-(N-((2-(4-tert.butoxycarbonyl-piperazin-1-yl)-ethyl)-carbonyl)-N-methyl-amino)-anilino)-1-phenyl-methylene]-6-ethoxycarbonyl-2-indolinone
(248) 3-Z-[1-(4-(N-((2-(piperidin-1-yl)-ethyl)-carbonyl)-N-methyl-amino)-anilino)-1-phenyl-methylene]-6-ethoxycarbonyl-2-indolinone
(249) 3-Z-[1-(4-(N-((2-(N-benzyl-N-methyl-amino)-ethyl)-carbonyl)-N-methyl-amino)-anilino)-1-phenyl-methylene]-6-ethoxycarbonyl-2-indolinone
(250) 3-Z-[1-(4-(N-dimethylaminomethylcarbonyl-N-isopropyl-amino)-anilino)-1-phenyl-methylene]-6-ethoxycarbonyl-2-indolinone
(251) 3-Z-[1-(4-(N-(piperidin-1-yl-methylcarbonyl)-N-isopropyl-amino)-anilino)-1-phenyl-methylene]-6-ethoxycarbonyl-2-indolinone
(252) 3-Z-[1-(4-(N-((4-tert.butoxycarbonyl-piperazin-1-yl)-methylcarbonyl)-N-isopropyl-amino)-anilino)-1-phenyl-methylene]-6-ethoxycarbonyl-2-indolinone
(253) 3-Z-[1-(4-(N-((N-benzyl-N-methyl-amino)-methylcarbonyl)-N-benzyl-amino)-anilino)-1-phenyl-methylene]-6-ethoxycarbonyl-2-indolinone
(254) 3-Z-[1-(4-(N-dimethylaminomethylcarbonyl-N-benzyl-amino)-anilino)-1-phenyl-methylene]-6-ethoxycarbonyl-2-indolinone
(255) 3-Z-[1-(4-(N-(piperidin-1-yl-methylcarbonyl)-N-benzyl-amino)-anilino)-1-phenyl-methylene]-6-ethoxycarbonyl-2-indolinone
(256) 3-Z-[1-(4-(1,2,4-triazol-2-yl-methyl)-anilino)-1-phenyl-methylene]-6-ethoxycarbonyl-2-indolinone
(257) 3-Z-[1-(4-(1,2,3-triazol-2-yl-methyl)-anilino)-1-phenyl-methylene]-6-ethoxycarbonyl-2-indolinone
(258) 3-Z-[1-(4-(1,2,3-triazol-1-yl-methyl)-anilino)-1-phenyl-methylene]-6-ethoxycarbonyl-2-indolinone (259) 3-Z-[1-(4-((N-aminocarbonylmethyl-N-methyl-amino)-methyl)-anilino)-1-phenyl-methylene]-6-ethoxycarbonyl-2-indolinone
(260) 3-Z-[1-(4-((di-(2-methoxy-ethyl)-amino)-methyl)-anilino)-1-phenyl-methylene]-6-ethoxycarbonyl-2-indolinone
(261) 3-Z-[1-(4-((di-(2-hydroxy-ethyl)-amino)-methyl)-anilino)-1-phenyl-methylene]-6-ethoxycarbonyl-2-indolinone
(262) 3-Z-[1-(4-((N-ethoxycarbonylmethyl-N-methyl-amino)-methyl)-anilino)-1-phenyl-methylene]-6-ethoxycarbonyl-2-indolinone
(263) 3-Z-[1-(4-(azetidin-1-yl-methyl)-anilino)-1-phenyl-methylene]-6-ethoxycarbonyl-2-indolinone
(264) 3-Z-[1-(4-(N-propyl-N-tert.butoxycarbonyl-aminomethyl)-anilino)-1-phenyl-methylene]-6-ethoxycarbonyl-2-indolinone
(265) 3-Z-[1-(4-((N-(2-(2-methoxy-ethoxy)-ethyl)-N-methyl-amino)-methyl)-anilino)-1-phenyl-methylene]-6-ethoxycarbonyl-2-indolinone
(266) 3-Z-[1-(4-((N-(tert.butoxycarbonyl-3-amino-propyl)-N-methyl-amino)-methyl)-anilino)-1-phenyl-methylene]-6-ethoxycarbonyl-2-indolinone
(267) 3-Z-[1-(4-((N-(methylcarbamoyl-methyl)-N-methyl-amino)-methyl)-anilino)-1-phenyl-methylene]-6-ethoxycarbonyl-2-indolinone
(268) 3-Z-[1-(4-((N-(dimethylcarbamoyl-methyl)-N-methyl-amino)-methyl)-anilino)-1-phenyl-methylene]-6-ethoxycarbonyl-2-indolinone
(269) 3-Z-[1-(4-((N-propyl-N-methyl-amino)-methyl)-anilino)-1-phenyl-methylene]-6-ethoxycarbonyl-2-indolinone
(270) 3-Z-[1-(4-((N-(2-dimethylamino-ethyl)-N-methyl-amino)-methyl)-anilino)-1-phenyl-methylene]-6-ethoxycarbonyl-2-indolinone
(271) 3-Z-[1-(4-((N-(3-dimethylamino-propyl)-N-methyl-amino)-methyl)-anilino)-1-phenyl-methylene]-6-ethoxycarbonyl-2-indolinone
(272) 3-Z-[1-(4-((N-(2-methoxy-ethyl)-N-methyl-amino)-methyl)-anilino)-1-phenyl-methylene]-6-ethoxycarbonyl-2-indolinone
(273) 3-Z-[1-(4-((N-(2-hydroxy-ethyl)-N-methyl-amino)-methyl)-anilino)-1-phenyl-methylene]-6-ethoxycarbonyl-2-indolinone
(274) 3-Z-[1-(4-((N-(dioxolan-2-yl-methyl)-N-methyl-amino)-methyl)-anilino)-1-phenyl-methylene]-6-ethoxycarbonyl-2-indolinone
(275) 3-Z-[1-(4-(3-oxo-piperazin-1-yl-methyl)-anilino)-1-phenyl-methylene]-6-ethoxycarbonyl-2-indolinone
(276) 3-Z-[1-(4-(N-(piperazin-1-yl-methylcarbonyl)-N-isopropyl-amino)-anilino)-1-phenyl-methylene]-6-ethoxycarbonyl-2-indolinone
(277) 3-Z-[1-(4-(N-((2-(piperazin-1-yl)-ethyl)-carbonyl)-N-methyl-amino)-anilino)-1-phenyl-methylene]-6-ethoxycarbonyl-2-indolinone
(278) 3-Z-[1-(4-((N-(3-amino-propyl)-N-methyl-amino)-methyl)-anilino)-1-phenyl-methylene]-6-ethoxycarbonyl-2-indolinone
(279) 3-Z-[1-(4-(N-(3-methylamino-propyl)-N-methylsulphonyl-amino)-anilino)-1-phenyl-methylene]-6-ethoxycarbonyl-2-indolinone
(280) 3-Z-[1-(4-Ureidomethyl-anilino)-1-phenyl-methylene]-6-ethoxycarbonyl-2-indolinone
(281) 3-Z-[1-(4-guanidinomethyl-anilino)-1-phenyl-methylene]-6-ethoxycarbonyl-2-indolinone
(282) 3-Z-[1-(4-(N-methylsulphonyl-aminomethyl)-anilino)-1-phenyl-methylene]-6-ethoxycarbonyl-2-indolinone
(283) 3-Z-[1-(4-(4-benzoyl-piperazin-1-yl-methyl)-anilino)-1-phenyl-methylene]-6-ethoxycarbonyl-2-indolinone
(284) 3-Z-[1-(4-((N-(3-acetylamino-propyl)-N-methyl-amino)-methyl)-anilino)-1-phenyl-methylene]-6-ethoxycarbonyl-2-indolinone
(285) 3-Z-[1-(4-((N-(3-methylsulphonylamino-propyl)-N-methyl-amino)-methyl)-anilino)-1-phenyl-methylene]-6-ethoxycarbonyl-2-indolinone
(286) 3-Z-[1-(4-((N-carboxymethyl-N-methyl-amino)-methyl)-anilino)-1-phenyl-methylene]-6-ethoxycarbonyl-2-indolinone
(287) 3-Z-(1-anilino-1-phenyl-methylene)-6-methoxycarbonyl-2-indolinone
(288) 3-Z-[1-(4-nitro-anilino)-1-phenyl-methylene]-6-methoxycarbonyl-2-indolinone
(289) 3-Z-[1-(4-fluoro-anilino)-1-phenyl-methylene]-6-methoxycarbonyl-2-indolinone
(290) 3-Z-[1-(4-chloro-anilino)-1-phenyl-methylene]-6-methoxycarbonyl-2-indolinone
(291) 3-Z-[1-(4-bromo-anilino)-1-phenyl-methylene]-6-methoxycarbonyl-2-indolinone
(292) 3-Z-[1-(4-iodo-anilino)-1-phenyl-methylene]-6-methoxycarbonyl-2-indolinone
(293) 3-Z-[1-(4-cyano-anilino)-1-phenyl-methylene]-6-methoxycarbonyl-2-indolinone
(294) 3-Z-[1-(4-carboxy-anilino)-1-phenyl-methylene]-6-methoxycarbonyl-2-indolinone
(295) 3-Z-[1-(4-methoxy-anilino)-1-phenyl-methylene]-6-methoxycarbonyl-2-indolinone
(296) 3-Z-[1-(4-ethoxy-anilino)-1-phenyl-methylene]-6-methoxycarbonyl-2-indolinone
(297) 3-Z-[1-(4-trifluoromethyl-anilino)-1-phenyl-methylene]-6-methoxycarbonyl-2-indolinone
(298) 3-Z-[1-(4-methylmercapto-anilino)-1-phenyl-methylene]-6-methoxycarbonyl-2-indolinone
(299) 3-Z-[1-(4-(isopropylaminomethyl)-anilino)-1-phenyl-methylene]-6-methoxycarbonyl-2-indolinone
(300) 3-Z-[1-(4-(anilinomethyl)-anilino)-1-phenyl-methylene]-6-methoxycarbonyl-2-indolinone
(301) 3-Z-[1-(4-(isobutylaminomethyl)-anilino)-1-phenyl-methylene]-6-methoxycarbonyl-2-indolinone
(302) 3-Z-[1-(4-(cyclohexylaminomethyl)-anilino)-1-phenyl-methylene]-6-methoxycarbonyl-2-indolinone
(303) 3-Z-[1-(4-(benzylaminomethyl)-anilino)-1-phenyl-methylene]-6-methoxycarbonyl-2-indolinone
(304) 3-Z-[1-(4-((N-methyl-N-propyl-amino)-methyl)-anilino)-1-phenyl-methylene]-6-methoxycarbonyl-2-indolinone
(305) 3-Z-[1-(4-((N-isopropyl-N-methyl-amino)-methyl)-anilino)-1-phenyl-methylene]-6-methoxycarbonyl-2-indolinone
(306) 3-Z-[1-(4-((N-ethyl-N-propyl-amino)-methyl)-anilino)-1-phenyl-methylene]-6-methoxycarbonyl-2-indolinone
(307) 3-Z-[1-(4-((N-ethyl-N-isopropyl-amino)-methyl)-anilino)-1-phenyl-methylene]-6-methoxycarbonyl-2-indolinone
(308) 3-Z-[1-(4-(dipropylaminomethyl)-anilino)-1-phenyl-methylene]-6-methoxycarbonyl-2-indolinone
(309) 3-Z-[1-(4-(diisopropylaminomethyl)-anilino)-1-phenyl-methylene]-6-methoxycarbonyl-2-indolinone (310) 3-Z-[1-(4-((N-benzyl-N-ethyl-amino)-methyl)-anilino)-1-phenyl-methylene]-6-methoxycarbonyl-2-indolinone
(311) 3-Z-[1-(4-(dibenzylaminomethyl)-anilino)-1-phenyl-methylene]-6-methoxycarbonyl-2-indolinone
(312) 3-Z-[1-(4-(3,6-dihydro-2H-pyridin-1-yl-methyl)-anilino)-1-phenyl-methylene]-6-methoxycarbonyl-2-indolinone
(313) 3-Z-[1-(4-(3,5-dimethyl-piperidin-1-yl-methyl)-anilino)-1-phenyl-methylene]-6-methoxycarbonyl-2-indolinone
(314) 3-Z-[1-(4-(azepan-1-yl-methyl)-anilino)-1-phenyl-methylene]-6-methoxycarbonyl-2-indolinone
(315) 3-Z-[1-(4-(2-amino-ethyl)-anilino)-1-phenyl-methylene]-6-methoxycarbonyl-2-indolinone
(316) 3-Z-[1-(4-(2-methylamino-ethyl)-anilino)-1-phenyl-methylene]-6-methoxycarbonyl-2-indolinone
(317) 3-Z-[1-(4-(2-ethylamino-ethyl)-anilino)-1-phenyl-methylene]-6-methoxycarbonyl-2-indolinone
(318) 3-Z-[1-(4-(2-dimethylamino-ethyl)-anilino)-1-phenyl-methylene]-6-methoxycarbonyl-2-indolinone
(319) 3-Z-[1-(4-(2-diethylamino-ethyl)-anilino)-1-phenyl-methylene]-6-methoxycarbonyl-2-indolinone
(320) 3-Z-[1-(4-(2-piperidin-1-yl-ethyl)-anilino)-1-phenyl-methylene]-6-methoxycarbonyl-2-indolinone
(321) 3-Z-[1-(4-(2-acetylamino-ethyl)-anilino)-1-phenyl-methylene]-6-methoxycarbonyl-2-indolinone
(322) 3-Z-[1-(4-(3-amino-propyl)-anilino)-1-phenyl-methylene]-6-methoxycarbonyl-2-indolinone
(323) 3-Z-[1-(4-(3-dimethylamino-propyl)-anilino)-1-phenyl-methylene]-6-methoxycarbonyl-2-indolinone
(324) 3-Z-[1-(4-(N-aminomethylcarbonyl-N-methyl-amino)-anilino)-1-phenyl-methylene]-6-methoxycarbonyl-2-indolinone
(325) 3-Z-[1-(4-(N-ethylaminomethylcarbonyl-N-methyl-amino)-anilino)-1-phenyl-methylene]-6-methoxycarbonyl-2-indolinone
(326) 3-Z-[1-(4-(N-diethylaminomethylcarbonyl-N-methyl-amino)-anilino)-1-phenyl-methylene]-6-methoxycarbonyl-2-indolinone
(327) 3-Z-[1-(4-(N-dipropylaminomethylcarbonyl-N-methyl-amino)-anilino)-1-phenyl-methylene]-6-methoxycarbonyl-2-indolinone
(328) 3-Z-[1-(4-(N-((N-ethyl-N-methyl-amino)-methylcarbonyl)-N-methyl-amino)-anilino)-1-phenyl-methylene]-6-methoxycarbonyl-2-indolinone
(329) 3-Z-[1-(4-(N-((N-ethyl-N-propyl-amino)-methylcarbonyl)-N-methyl-amino)-anilino)-1-phenyl-methylene]-6-methoxycarbonyl-2-indolinone
(330) 3-Z-[1-(4-(N-((N-methyl-N-propyl-amino)-methylcarbonyl)-N-methyl-amino)-anilino)-1-phenyl-methylene]-6-methoxycarbonyl-2-indolinone
(331) 3-Z-[1-(4-(N-dimethylaminomethylcarbonyl-N-ethyl-amino)-anilino)-1-phenyl-methylene]-6-methoxycarbonyl-2-indolinone
(332) 3-Z-[1-(4-(N-dimethylaminomethylcarbonyl-N-propyl-amino)-anilino)-1-phenyl-methylene]-6-methoxycarbonyl-2-indolinone
(333) 3-Z-[1-(4-(N-dimethylaminomethylcarbonyl-N-butyl-amino)-anilino)-1-phenyl-methylene]-6-methoxycarbonyl-2-indolinone
(334) 3-Z-[1-(4-(N-(2-amino-ethylcarbonyl)-N-methyl-amino)-anilino)-1-phenyl-methylene]-6-methoxycarbonyl-2-indolinone
(335) 3-Z-[1-(4-(N-(2-diethylamino-ethylcarbonyl)-N-methyl-amino)-anilino)-1-phenyl-methylene]-6-methoxycarbonyl-2-indolinone
(336) 3-Z-[1-(4-(N-acetyl-N-(2-aminoethyl)-amino)-anilino)-1-phenyl-methylene]-6-methoxycarbonyl-2-indolinone
(337) 3-Z-[1-(4-(N-acetyl-N-(2-methylamino-ethyl)-amino)-anilino)-1-phenyl-methylene]-6-methoxycarbonyl-2-indolinone
(338) 3-Z-[1-(4-(N-acetyl-N-(3-methylamino-propyl)-amino)-anilino)-1-phenyl-methylene]-6-methoxycarbonyl-2-indolinone
(339) 3-Z-[1-(4-(N-acetyl-N-(2-piperidin-1-yl-ethyl)-amino)-anilino)-1-phenyl-methylene]-6-methoxycarbonyl-2-indolinone
(340) 3-Z-[1-(4-(N-acetyl-N-(aminocarbonylmethyl)-amino)-anilino)-1-phenyl-methylene]-6-methoxycarbonyl-2-indolinone
(341) 3-Z-[1-(4-(N-acetyl-N-(piperidin-1-yl-carbonylmethyl)-amino)-anilino)-1-phenyl-methylene]-6-methoxycarbonyl-2-indolinone
(342) 3-Z-[1-(4-(N-methyl-N-(aminocarbonyl)-amino)-anilino)-1-phenyl-methylene]-6-methoxycarbonyl-2-indolinone
(343) 3-Z-[1-(4-(N-methyl-N-(methylaminocarbonyl)-amino)-anilino)-1-phenyl-methylene]-6-methoxycarbonyl-2-indolinone
(344) 3-Z-[1-(4-(N-methyl-N-(dimethylaminocarbonyl)-amino)-anilino)-1-phenyl-methylene]-6-methoxycarbonyl-2-indolinone
(345) 3-Z-[1-(4-(N-methyl-N-(piperidin-1-yl-carbonyl)-amino)-anilino)-1-phenyl-methylene]-6-methoxycarbonyl-2-indolinone
(346) 3-Z-[1-(4-(N-(2-ethylamino-ethyl)-N-methylsulphonyl-amino)-anilino)-1-phenyl-methylene]-6-methoxycarbonyl-2-indolinone
(347) 3-Z-[1-(4-(N-(2-diethylamino-ethyl)-N-methylsulphonyl-amino)-anilino)-1-phenyl-methylene]-6-methoxycarbonyl-2-indolinone
(348) 3-Z-[1-(4-(N-(2-pyrrolidin-1-yl-ethyl)-N-methylsulphonyl-amino)-anilino)-1-phenyl-methylene]-6-methoxycarbonyl-2-indolinone
(349) 3-Z-[1-(4-(N-(2-piperidin-1-yl-ethyl)-N-methylsulphonyl-amino)-anilino)-1-phenyl-methylene]-6-methoxycarbonyl-2-indolinone
(350) 3-Z-[1-(4-(N-(2-piperazin-1-yl-ethyl)-N-methylsulphonyl-amino)-anilino)-1-phenyl-methylene]-6-methoxycarbonyl-2-indolinone
(351) 3-Z-[1-(4-(N-(2-(4-morpholin-1-yl)-ethyl)-N-methylsulphonyl-amino)-anilino)-1-phenyl-methylene]-6-methoxycarbonyl-2-indolinone
(352) 3-Z-[1-(4-(N-(ethylaminocarbonylmethyl)-N-methylsulphonyl-amino)-anilino)-1-phenyl-methylene]-6-methoxycarbonyl-2-indolinone
(353) 3-Z-[1-(4-(N-(diethylaminocarbonylmethyl)-N-methylsulphonyl-amino)-anilino)-1-phenyl-methylene]-6-methoxycarbonyl-2-indolinone
(354) 3-Z-[1-(4-(N-(pyrrolidin-1-yl-carbonylmethyl)-N-methylsulphonyl-amino)-anilino)-1-phenyl-methylene]-6-methoxycarbonyl-2-indolinone
(355) 3-Z-[1-(4-(N-(piperidin-1-yl-carbonylmethyl)-N-methyl-sulphonyl-amino)-anilino)-1-phenyl-methylene]-6-methoxycarbonyl-2-indolinone
(356) 3-Z-[1-(4-(N-(piperazin-1-yl-carbonylmethyl)-N-methyl-sulphonyl-amino)-anilino)-1-phenyl-methylene]-6-methoxycarbonyl-2-indolinone
(357) 3-Z-[1-(4-(N-((morpholin-4-yl)-carbonylmethyl)-N-methylsulphonyl-amino)-anilino)-1-phenyl-methylene]-6-methoxycarbonyl-2-indolinone (358) 3-Z-[1-(4-(2-dimethylamino-ethoxy)-anilino)-1-phenyl-methylene]-6-methoxycarbonyl-2-indolinone
(359) 3-Z-[1-(4-(3-dimethylamino-propoxy)-anilino)-1-phenyl-methylene]-6-methoxycarbonyl-2-indolinone
(360) 3-Z-[1-(4-(aminocarbonylmethyl)-anilino)-1-phenyl-methylene]-6-methoxycarbonyl-2-indolinone
(361) 3-Z-[1-(4-(2-aminocarbonyl-ethyl)-anilino)-1-phenyl-methylene]-6-methoxycarbonyl-2-indolinone
(362) 3-Z-[1-(4-(pyridin-2-yl)-anilino)-1-phenyl-methylene]-6-methoxycarbonyl-2-indolinone
(363) 3-Z-[1-(4-(pyridine-3-yl)-anilino)-1-phenyl-methylene]-6-methoxycarbonyl-2-indolinone
(364) 3-Z-[1-(4((N-phenethyl-N-methyl-amino)-methyl)-anilino)-1-phenyl-methylene]-6-methoxycarbonyl-2-indolinone
(365) 3-Z-[1-(4-(N-acetyl-N-methyl-amino)-anilino)-1-phenyl-methylene]-6-methoxycarbonyl-2-indolinone
(366) 3-Z-[1-(4-(N-ethylcarbonyl-N-(dimethylaminocarbonyl-methyl)-amino)-anilino)-1-phenyl-methylene]-6-methoxycarbonyl-2-indolinone
(367) 3-Z-[1-(4-(N-methyl-N-methylsulphonyl-amino)-anilino)-1-phenyl-methylene]-6-methoxycarbonyl-2-indolinone
(368) 3-Z-[1-(4-carboxymethyl-anilino)-1-phenyl-methylene]-6-methoxycarbonyl-2-indolinone
(369) 3-Z-[1-(4-carbamoylmethyl-anilino)-1-phenyl-methylene]-6-methoxycarbonyl-2-indolinone
(370) 3-Z-[1-(4-dimethylcarbamoylmethyl-anilino)-1-phenyl-methylene]-6-methoxycarbonyl-2-indolinone
(371) 3-Z-[1-(4-tetrazol-5-yl-anilino)-1-phenyl-methylene]-6-methoxycarbonyl-2-indolinone
(372) 3-Z-[1-(4-(piperidin-1-yl-methyl)-anilino)-methylene]-6-methoxycarbonyl-2-indolinone
(373) 3-Z-[1-(4-(piperidin-1-yl-methyl)-anilino)-ethylidene]-6-methoxycarbonyl-2-indolinone
(374) 3-Z-[1-(4-(piperidin-1-yl-methyl)-anilino)-propylidene]-6-methoxycarbonyl-2-indolinone
(375) 3-Z-[1-(4-(piperidin-1-yl-methyl)-anilino)-butylidene]-6-methoxycarbonyl-2-indolinone
(376) 3-Z-[1-(4-(N-(3-dimethylamino-propyl)-N-acetyl-amino)-anilino)-methylene]-6-methoxycarbonyl-2-indolinone
(377) 3-Z-[1-(4-(N-(3-dimethylamino-propyl)-N-acetyl-amino)-anilino)-ethylidene]-6-methoxycarbonyl-2-indolinone
(378) 3-Z-[1-(4-(N-(3-dimethylamino-propyl)-N-acetyl-amino)-anilino)-propylidene]-6-methoxycarbonyl-2-indolinone
(379) 3-Z-[1-(4-(N-(3-dimethylamino-propyl)-N-acetyl-amino)-anilino)-butylidene]-6-methoxycarbonyl-2-indolinone
(380) 3-Z-[1-(4-(N-(2-dimethylamino-ethyl)-N-methylsulphonyl-amino)-anilino)-methylene]-6-methoxycarbonyl-2-indolinone
(381) 3-Z-[1-(4-(N-(2-dimethylamino-ethyl)-N-methylsulphonyl-amino)-anilino)-ethylidene]-6-methoxycarbonyl-2-indolinone
(382) 3-Z-[1-(4-(N-(2-dimethylamino-ethyl)-N-methylsulphonyl-amino)-anilino)-propylidene]-6-methoxycarbonyl-2-indolinone
(383) 3-Z-[1-(4-(N-(2-dimethylamino-ethyl)-N-methylsulphonyl-amino)-anilino)-butylidene]-6-methoxycarbonyl-2-indolinone
(384) 3-Z-[1-(4-tetrazol-5-yl-anilino)-methylene]-6-methoxy-carbonyl-2-indolinone
(385) 3-Z-[1-(4-tetrazol-5-yl-anilino)-ethylidene]-6-methoxycarbonyl-2-indolinone
(386) 3-Z-[1-(4-tetrazol-5-yl-anilino)-propylidene]-6-methoxycarbonyl-2-indolinone
(387) 3-Z-[1-(4-tetrazol-5-yl-anilino)-butylidene]-6-methoxycarbonyl-2-indolinone
(388) 3-Z-[1-(4-carboxy-anilino)-methylene]-6-methoxycarbonyl-2-indolinone
(389) 3-Z-[1-(4-carboxy-anilino)-ethylidene]-6-methoxycarbonyl-2-indolinone
(390) 3-Z-[1-(4-carboxy-anilino)-propylidene]-6-methoxycarbonyl-2-indolinone
(391) 3-Z-[1-(4-carboxy-anilino)-butylidene]-6-methoxycarbonyl-2-indolinone
(392) 3-Z-[1-(4-(N-benzyl-N-methyl-aminomethyl)-anilino)-1-methyl-methylene]-6-methoxycarbonyl-2-indolinone
(393) 3-Z-[1-(4-(2,3,4,5-tetrahydro-benzo(d)azepin-3-yl-methyl)-anilino)-1-methyl-methylene]-6-methoxycarbonyl-2-indolinone
(394) 3-Z-[1-(4-((benzo(1,3)dioxol-5-yl-methyl)-methyl-amino-methyl)-anilino)-1-methyl-methylene]-6-methoxycarbonyl-2-indolinone
(395) 3-Z-[1-(4-(N-phenethyl-N-methyl-aminomethyl)-anilino)-1-methyl-methylene]-6-methoxycarbonyl-2-indolinone
(396) 3-Z-[1-(4-(N-(3,4-dimethoxy-benzyl)-N-methyl-amino-methyl)-anilino)-1-methyl-methylene]-6-methoxycarbonyl-2-indolinone
(397) 3-Z-[1-(4-(N-(4-chloro-benzyl)-N-methyl-amino-methyl)-anilino)-1-methyl-methylene]-6-methoxycarbonyl-2-indolinone
(398) 3-Z-[1-(4-(N-(4-methylbenzyl)-N-methyl-amino-methyl)-anilino)-1-methyl-methylene]-6-methoxycarbonyl-2-indolinone
(399) 3-Z-[1-(4-(N-(4-fluoro-benzyl)-N-methyl-amino-methyl)-anilino)-1-methyl-methylene]-6-methoxycarbonyl-2-indolinone
(400) 3-Z-[1-(4-(N-(4-bromo-benzyl)-N-methyl-amino-methyl)-anilino)-1-methyl-methylene]-6-methoxycarbonyl-2-indolinone
(401) 3-Z-[1-(4-(N-(3-dimethylamino-propionyl)-N-dimethylaminocarbonylmethyl-amino)-anilino)-1-phenyl-methylene]-6-methoxycarbonyl-2-indolinone
(402) 3-Z-[1-(4-(N-(4-dimethylamino-butyryl)-N-dimethyl-aminocarbonylmethyl-amino)-anilino)-1-phenyl-methylene]-6-methoxycarbonyl-2-indolinone
(403) 3-Z-[1-(4-(N-dimethylaminocarbonylmethyl-N-(2-dimethylamino-ethylsulphonyl)-amino)-anilino)-1-phenyl-methylene]-6-methoxycarbonyl-2-indolinone
(404) 3-Z-[1-(4-(N-dimethylaminocarbonylmethyl-N-(3-dimethylamino-propylsulphonyl)-amino)-anilino)-1-phenyl-methylene]-6-methoxycarbonyl-2-indolinone
(405) 3-Z-[1-(4-((2-hydroxy-ethyl)-amino-methyl)-anilino)-1-phenyl-methylene]-6-methoxycarbonyl-2-indolinone
(406) 3-Z-[1-(4-((2-methoxy-ethyl)-amino-methyl)-anilino)-1-phenyl-methylene]-6-methoxycarbonyl-2-indolinone
(407) 3-Z-[1-(4-((2-dimethylamino-ethyl)-amino-methyl)-anilino)-1-phenyl-methylene]-6-methoxycarbonyl-2-indolinone
(408) 3-Z-[1-(4-((3-dimethylamino-propyl)-amino-methyl)-anilino)-1-phenyl-methylene]-6-methoxycarbonyl-2-indolinone
(409) 3-Z-[1-(4-((N-tert.butoxycarbonyl-2-amino-ethyl)-amino-methyl)-anilino)-1-phenyl-methylene]-6-methoxycarbonyl-2-indolinone (410) 3-Z-[1-(4-((N-tert.butoxycarbonyl-3-amino-propyl)-amino-methyl)-anilino)-1-phenyl-methylene]-6-methoxycarbonyl-2-indolinone
(411) 3-Z-[1-(4-((2-amino-ethyl)-amino-methyl)-anilino)-1-phenyl-methylene]-6-methoxycarbonyl-2-indolinone
(412) 3-Z-[1-(4-((3-amino-propyl)-amino-methyl)-anilino)-1-phenyl-methylene]-6-methoxycarbonyl-2-indolinone
(413) 3-Z-[1-(4-((2-acetylamino-ethyl)-amino-methyl)-anilino)-1-phenyl-methylene]-6-methoxycarbonyl-2-indolinone
(414) 3-Z-[1-(4-((3-acetylamino-propyl)-amino-methyl)-anilino)-1-phenyl-methylene]-6-methoxycarbonyl-2-indolinone
(415) 3-Z-[1-(4-((2-methylsulphonylamino-ethyl)-amino-methyl)-anilino)-1-phenyl-methylene]-6-methoxycarbonyl-2-indolinone
(416) 3-Z-[1-(4-((3-methylsulphonylamino-propyl)-amino-methyl)-anilino)-1-phenyl-methylene]-6-methoxycarbonyl-2-indolinone
(417) 3-Z-[1-(4-(N-(N-tert.butoxycarbonyl-2-amino-ethyl)-N-methyl-amino-methyl)-anilino)-1-phenyl-methylene]-6-methoxycarbonyl-2-indolinone
(418) 3-Z-[1-(4-(N-(2-amino-ethyl)-N-methyl-amino-methyl)-anilino)-1-phenyl-methylene]-6-methoxycarbonyl-2-indolinone
(419) 3-Z-[1-(4-(N-(2-acetylamino-ethyl)-N-methyl-amino-methyl)-anilino)-1-phenyl-methylene]-6-methoxycarbonyl-2-indolinone
(420) 3-Z-[1-(4-(N-(2-methylsulphonylamino-ethyl)-N-methyl-amino-methyl)-anilino)-1-phenyl-methylene]-6-methoxycarbonyl-2-indolinone
(421) 3-Z-[1-(4-(carboxymethyl-amino-methyl)-anilino)-1-phenyl-methylene]-6-methoxycarbonyl-2-indolinone
(422) 3-Z-[1-(4-(ethoxycarbonylmethyl-amino-methyl)-anilino)-1-phenyl-methylene]-6-methoxycarbonyl-2-indolinone
(423) 3-Z-[1-(4-(carbamoylmethyl-amino-methyl)-anilino)-1-phenyl-methylene]-6-methoxycarbonyl-2-indolinone
(424) 3-Z-[1-(4-(dimethylcarbamoyl-methyl-amino-methyl)-anilino)-1-phenyl-methylene]-6-methoxycarbonyl-2-indolinone
(425) 3-Z-[1-(4-(methylcarbamoyl-methyl-amino-methyl)-anilino)-1-phenyl-methylene]-6-methoxycarbonyl-2-indolinone
(426) 3-Z-[1-(4-(N-dimethylaminomethylcarbonyl-N-methyl-amino)-3-amino-anilino)-1-phenyl-methylene]-6-methoxycarbonyl-2-indolinone
(427) 3-Z-[1-(4-(N-dimethylaminomethylcarbonyl-N-methyl-amino)-3-nitro-anilino)-1-phenyl-methylene]-6-methoxycarbonyl-2-indolinone
(428) 3-Z-[1-(4-(N-dimethylaminomethylcarbonyl-N-methyl-amino)-3-acetylamino-anilino)-1-phenyl-methylene]-6-methoxycarbonyl-2-indolinone
(429) 3-Z-[1-(4-(N-dimethylaminomethylcarbonyl-N-methyl-amino)-3-methylsulphonylamino-anilino)-1-phenyl-methylene]-6-methoxycarbonyl-2-indolinone
(430) 3-Z-[1-(4-(N-dimethylaminomethylcarbonyl-N-methyl-amino)-3-cyano-anilino)-1-phenyl-methylene]-6-methoxycarbonyl-2-indolinone
(431) 3-Z-[1-(4-(N-dimethylaminomethylcarbonyl-N-methyl-amino)-3-hydroxy-anilino)-1-phenyl-methylene]-6-methoxycarbonyl-2-indolinone
(432) 3-Z-[1-(4-(N-dimethylaminomethylcarbonyl-N-methyl-amino)-3-methoxy-anilino)-1-phenyl-methylene]-6-methoxycarbonyl-2-indolinone
(433) 3-Z-[1-(4-(N-dimethylaminomethylcarbonyl-N-methyl-amino)-3-ethoxycarbonyl-anilino)-1-phenyl-methylene]-6-methoxycarbonyl-2-indolinone
(434) 3-Z-[1-(4-(N-dimethylaminomethylcarbonyl-N-methyl-amino)-3-carboxy-anilino)-1-phenyl-methylene]-6-methoxycarbonyl-2-indolinone
(435) 3-Z-[1-(4-(N-dimethylaminomethylcarbonyl-N-methyl-amino)-3-carbamoyl-anilino)-1-phenyl-methylene]-6-methoxycarbonyl-2-indolinone
(436) 3-Z-[1-(4-(N-dimethylaminomethylcarbonyl-N-methyl-amino)-3-chloro-anilino)-1-phenyl-methylene]-6-methoxycarbonyl-2-indolinone
(437) 3-Z-[1-(4-(N-dimethylaminomethylcarbonyl-N-methyl-amino)-3-fluoro-anilino)-1-phenyl-methylene]-6-methoxycarbonyl-2-indolinone
(438) 3-Z-[1-(4-(N-dimethylaminomethylcarbonyl-N-methyl-amino)-3-bromo-anilino)-1-phenyl-methylene]-6-methoxycarbonyl-2-indolinone
(439) 3-Z-[1-(4-(N-dimethylaminomethylcarbonyl-N-methyl-amino)-3-methyl-anilino)-1-phenyl-methylene]-6-methoxycarbonyl-2-indolinone
(440) 3-Z-[1-(4-(N-dimethylaminomethylcarbonyl-N-methyl-amino)-3-trifluoromethyl-anilino)-1-phenyl-methylene]-6-methoxycarbonyl-2-indolinone
(441) 3-Z-[1-(4-(N-dimethylaminomethylcarbonyl-N-methyl-amino)-3,5-dibromo-anilino)-1-phenyl-methylene]-6-methoxycarbonyl-2-indolinone
(442) 3-Z-[1-(4-(N-dimethylaminomethylcarbonyl-N-methyl-amino)-3,5-dichloro-anilino)-1-phenyl-methylene]-6-methoxycarbonyl-2-indolinone
(443) 3-Z-[1-(4-(dimethylaminomethyl)-3-amino-anilino)-1-phenyl-methylene]-6-methoxycarbonyl-2-indolinone
(444) 3-Z-[1-(4-(dimethylaminomethyl)-3-nitro-anilino)-1-phenyl-methylene]-6-methoxycarbonyl-2-indolinone
(445) 3-Z-[1-(4-(dimethylaminomethyl)-3-acetylamino-anilino)-1-phenyl-methylene]-6-methoxycarbonyl-2-indolinone
(446) 3-Z-[1-(4-(dimethylaminomethyl)-3-methylsulphonylamino-anilino)-1-phenyl-methylene]-6-methoxycarbonyl-2-indolinone
(447) 3-Z-[1-(4-(dimethylaminomethyl)-3-cyano-anilino)-1-phenyl-methylene]-6-methoxycarbonyl-2-indolinone
(448) 3-Z-[1-(4-(dimethylaminomethyl)-3-hydroxy-anilino)-1-phenyl-methylene]-6-methoxycarbonyl-2-indolinone
(449) 3-Z-[1-(4-(dimethylaminomethyl)-3-methoxy-anilino)-1-phenyl-methylene]-6-methoxycarbonyl-2-indolinone
(450) 3-Z-[1-(4-(dimethylaminomethyl)-3-ethoxycarbonyl-anilino)-1-phenyl-methylene]-6-methoxycarbonyl-2-indolinone
(451) 3-Z-[1-(4-(dimethylaminomethyl)-3-carboxy-anilino)-1-phenyl-methylene]-6-methoxycarbonyl-2-indolinone
(452) 3-Z-[1-(4-(dimethylaminomethyl)-3-carbamoyl-anilino)-1-phenyl-methylene]-6-methoxycarbonyl-2-indolinone
(453) 3-Z-[1-(4-(dimethylaminomethyl)-3-chloro-anilino)-1-phenyl-methylene]-6-methoxycarbonyl-2-indolinone
(454) 3-Z-[1-(4-(dimethylaminomethyl)-3-fluoro-anilino)-1-phenyl-methylene]-6-methoxycarbonyl-2-indolinone
(455) 3-Z-[1-(4-(dimethylaminomethyl)-3-bromo-anilino)-1-phenyl-methylene]-6-methoxycarbonyl-2-indolinone
(456) 3-Z-[1-(4-(dimethylaminomethyl)-3-methyl-anilino)-1-phenyl-methylene]-6-methoxycarbonyl-2-indolinone (457) 3-Z-[1-(4-(dimethylaminomethyl)-3-trifluoromethyl-anilino)-1-phenyl-methylene]-6-methoxycarbonyl-2-indolinone
(458) 3-Z-[1-(4-dimethylaminomethyl-3,5-dibromo-anilino)-1-phenyl-methylene]-6-methoxycarbonyl-2-indolinone
(459) 3-Z-[1-(4-(dimethylaminomethyl)-3,5-dichloro-anilino)-1-phenyl-methylene]-6-methoxycarbonyl-2-indolinone
(460) 3-Z-[1-(4-(dimethylaminomethyl)-anilino)-1-phenyl-methylene]-6-[(2-hydroxy-ethoxy)-carbonyl]-2-indolinone
(461) 3-Z-[1-(4-(dimethylaminomethyl)-anilino)-1-phenyl-methylene]-6-[(ethoxycarbonyl-methoxy)-carbonyl]-2-indolinone
(462) 3-Z-[1-(4-(dimethylaminomethyl)-anilino)-1-phenyl-methylene]-6-[(carboxy-methoxy)-carbonyl]-2-indolinone
(463) 3-Z-[1-(4-(dimethylaminomethyl)-anilino)-1-phenyl-methylene]-6-[(carbamoyl-methoxy)-carbonyl]-2-indolinone
(464) 3-Z-[1-(4-(N-dimethylaminomethylcarbonyl-N-methyl-amino)-anilino)-1-phenyl-methylene]-6-[(2-hydroxy-ethoxy)-carbonyl]-2-indolinone
(465) 3-Z-[1-(4-(N-dimethylaminomethylcarbonyl-N-methyl-amino)-anilino)-1-phenyl-methylene]-6-[(ethoxycarbonyl-methoxy)-carbonyl]-2-indolinone
(466) 3-Z-[1-(4-(N-dimethylaminomethylcarbonyl-N-methyl-amino)-anilino)-1-phenyl-methylene]-6-[(carboxy-methoxy)-carbonyl]-2-indolinone
(467) 3-Z-[1-(4-(N-dimethylaminomethylcarbonyl-N-methyl-amino)-anilino)-1-phenyl-methylene]-6-[(carbamoyl-methoxy)-carbonyl]-2-indolinone
(468) 3-Z-[1-(4-(N-dimethylaminomethylcarbonyl-N-methyl-amino)-anilino)-1-phenyl-methylene]-6-[(2-methoxy-ethoxy)-carbonyl]-2-indolinone
(469) 3-Z-[1-(4-(N-dimethylaminomethylcarbonyl-N-methyl-amino)-anilino)-1-phenyl-methylene]-6-[(2-dimethylamino-ethoxy)-carbonyl]-2-indolinone
(470) 3-Z-[1-(4-(N-dimethylaminomethylcarbonyl-N-methyl-amino)-anilino)-1-phenyl-methylene]-6-[(2-(N-tert.butoxycarbonyl-amino)-ethoxy)-carbonyl]-2-indolinone
(471) 3-Z-[1-(4-(N-dimethylaminomethylcarbonyl-N-methyl-amino)-anilino)-1-phenyl-methylene]-6-[(2-amino-ethoxy)-carbonyl]-2-indolinone
(472) 3-Z-[1-(4-(N-dimethylaminomethylcarbonyl-N-methyl-amino)-anilino)-1-phenyl-methylene]-6-[(2,2,2-trifluoroethoxy)-carbonyl]-2-indolinone
(473) 3-Z-[1-(4-(N-((4-methyl-piperazin-1-yl)-methylcarbonyl)-N-methyl-amino)-anilino)-1-phenyl-methylene]-6-methoxycarbonyl-2-indolinone
(474) 3-Z-[1-(4-(N-(imidazo-1-yl-methylcarbonyl)-N-methyl-amino)-anilino)-1-phenyl-methylene]-6-methoxycarbonyl-2-indolinone
(475) 3-Z-[1-(4-(N-(phthalimido-2-yl-methylcarbonyl)-N-methyl-amino)-anilino)-1-phenyl-methylene]-6-methoxycarbonyl-2-indolinone
(476) 3-Z-[1-(4-(N-aminomethylcarbonyl-N-methyl-amino)-anilino)-1-phenyl-methylene]-6-methoxycarbonyl-2-indolinone
(477) 3-Z-[1-(4-(N-acetylaminomethylcarbonyl-N-methyl-amino)-anilino)-1-phenyl-methylene]-6-methoxycarbonyl-2-indolinone
(478) 3-Z-[1-(4-(N-methylsulphonylaminomethylcarbonyl-N-methyl-amino)-anilino)-1-phenyl-methylene]-6-methoxycarbonyl-2-indolinone
(479) 3-Z-[1-(4-(N-((N-(2-methoxyethyl)-N-methyl-amino)-methylcarbonyl)-N-methyl-amino)-anilino)-1-phenyl-methylene]-6-methoxycarbonyl-2-indolinone
(480) 3-Z-[1-(4-(N-((N-(2-dimethylaminoethyl)-N-methyl-amino)-methylcarbonyl)-N-methyl-amino)-anilino)-1-phenyl-methylene]-6-methoxycarbonyl-2-indolinone
(481) 3-Z-[1-(4-(N-((di-(2-hydroxyethyl)-amino)-methylcarbonyl)-N-methyl-amino)-anilino)-1-phenyl-methylene]-6-methoxycarbonyl-2-indolinone
(482) 3-Z-[1-(4-tert.butoxycarbonylmethyl-anilino)-1-phenyl-methylene]-6-methoxycarbonyl-2-indolinone
(483) 3-Z-[1-(4-(N-dimethylaminomethylcarbonyl-N-methyl-amino)-anilino)-methylene]-6-methoxycarbonyl-2-indolinone
(484) 3-Z-[1-(4-(N-dimethylaminomethylcarbonyl-N-methyl-amino)-anilino)-ethylidene]-6-methoxycarbonyl-2-indolinone
(485) 3-Z-[1-(4-(N-dimethylaminomethylcarbonyl-N-methyl-amino)-anilino)-propylidene]-6-methoxycarbonyl-2-indolinone
(486) 3-Z-[1-(4-(N-dimethylaminomethylcarbonyl-N-methyl-amino)-anilino)-butylidene]-6-methoxycarbonyl-2-indolinone
(487) 3-Z-[1-(4-(dimethylaminomethyl)-anilino)-methylene]-6-methoxycarbonyl-2-indolinone
(488) 3-Z-[1-(4-(dimethylaminomethyl)-anilino)-ethylidene]-6-methoxycarbonyl-2-indolinone
(489) 3-Z-[1-(4-(dimethylaminomethyl)-anilino)-propylidene]-6-methoxycarbonyl-2-indolinone
(490) 3-Z-[1-(4-(dimethylaminomethyl)-anilino)-butylidene]-6-methoxycarbonyl-2-indolinone
(491) 3-Z-[1-(4-tert.butyloxycarbonyl-anilino)-1-phenyl-methylene]-6-methoxycarbonyl-2-indolinone
(492) 3-Z-[1-(4-(N-(2-dimethylamino-ethyl)-N-methyl-amino)-anilino)-1-phenyl-methylene]-6-methoxycarbonyl-2-indolinone
(493) 3-Z-[1-(4-(N-(3-dimethylamino-propyl)-N-methyl-amino)-anilino)-1-phenyl-methylene]-6-methoxycarbonyl-2-indolinone
(494) 3-Z-[1-(4-(N-methyl-acetylamino)-anilino)-1-phenyl-methylene]-6-methoxycarbonyl-2-indolinone
(495) 3-Z-[1-(4-(imidazol-4-yl)-anilino)-1-phenyl-methylene]-6-methoxycarbonyl-2-indolinone
(496) 3-Z-[1-(4-((N-(dioxolan-2-yl-methyl)-N-methyl-amino)-methyl)-anilino)-1-phenyl-methylene]-6-methoxycarbonyl-2-indolinone
(497) 3-Z-[1-(4-(N-benzyl-N-methyl-amino-methyl)-anilino)-1-methyl-methylene]-6-carbamoyl-2-indolinone
(498) 3-Z-[1-(4-(2,3,4,5-tetrahydro-benzo(d)azepin-3-yl-methyl)-anilino)-1-methyl-methylene]-6-carbamoyl-2-indolinone
(499) 3-Z-[1-(4-((benzo(1,3)dioxol-5-yl-methyl)-methyl-amino-methyl)-anilino)-1-methyl-methylene]-6-carbamoyl-2-indolinone
(500) 3-Z-[1-(4-(N-phenethyl-N-methyl-amino-methyl)-anilino)-1-methyl-methylene]-6-carbamoyl-2-indolinone
(501) 3-Z-[1-(4-(N-(3,4-dimethoxy-benzyl)-N-methyl-amino-methyl)-anilino)-1-methyl-methylene]-6-carbamoyl-2-indolinone
(502) 3-Z-[1-(4-(N-(4-chloro-benzyl)-N-methyl-amino-methyl)-anilino)-1-methyl-methylene]-6-carbamoyl-2-indolinone
(503) 3-Z-[1-(4-(N-(4-methyl-benzyl)-N-methyl-amino-methyl)-anilino)-1-methyl-methylene]-6-carbamoyl-2-indolinone (504) 3-Z-[1-(4-(N-(4-fluoro-benzyl)-N-methyl-aminomethyl)-anilino)-1-methyl-methylene]-6-carbamoyl-2-indolinone
(505) 3-Z-[1-(4-(N-(4-bromo-benzyl)-N-methyl-aminomethyl)-anilino)-1-methyl-methylene]-6-carbamoyl-2-indolinone
(506) 3-Z-[1-(4-((N-(2-methoxy-ethyl)-N-methyl-amino)-methyl)-anilino)-1-phenyl-methylene]-6-methoxycarbonyl-2-indolinone
(507) 3-Z-[1-(4-(dimethylaminomethyl)-anilino)-1-phenyl-methylene]-6-[(2-amino-ethoxy)-carbonyl]-2-indolinone
(508) 3-Z-[1-(4-((N-(3-methylsulfonylamino-propyl)-N-methyl-amino)-methyl)-anilino)-1-phenyl-methylene]-6-methoxycarbonyl-2-indolinone
(509) 3-Z-[1-(4-(piperidin-1-yl-methyl)-anilino)-1-phenyl-methylene]-6-carbamoyl-2-indolinone-trifluoroacetate
(510) 3-Z-(1-anilino-1-phenyl-methylene)-6-carbamoyl-2-indolinone
(511) 3-Z-[1-(4-dimethylaminomethyl-anilino)-1-phenyl-methylene]-6-carbamoyl-2-indolinone-trifluoroacetate
(512) 3-Z-[1-(4-(2-diethylamino-ethyl)-anilino)-1-phenyl-methylene]-6-carbamoyl-2-indolinone-trifluoroacetate
(513) 3-Z-[1-(4-(morpholin-4-yl-methyl)-anilino)-1-phenyl-methylene]-6-carbamoyl-2-indolinone-trifluoroacetate
(514) 3-Z-[1-(4-(1-oxo-thiomorpholin-4-yl-methyl)-anilino)-1-phenyl-methylene]-6-carbamoyl-2-indolinone-trifluoroacetate
(515) 3-Z-[1-(4-(1,1-dioxo-thiomorpholin-4-yl-methyl)-anilino)-1-phenyl-methylene]-6-carbamoyl-2-indolinone-trifluoroacetate
(516) 3-Z-[1-(4-(benzylaminomethyl)-anilino)-1-phenyl-methylene]-6-carbamoyl-2-indolinone-trifluoroacetate
(517) 3-Z-[1-(4-(amino-methyl)-anilino)-1-phenyl-methylene]-6-carbamoyl-2-indolinone-trifluoroacetate
(518) 3-Z-[1-(4-(2,6-dimethylpiperidin-1-yl-methyl)-anilino)-1-phenyl-methylene]-6-carbamoyl-2-indolinone-trifluoroacetate
(519) 3-Z-[1-(4-(pyrrolidin-1-yl-methyl)-anilino)-1-phenyl-methylene]-6-carbamoyl-2-indolinone-trifluoroacetate
(520) 3-Z-[1-(3-(dimethylaminomethyl)-anilino)-1-phenyl-methylene]-6-carbamoyl-2-indolinone-trifluoroacetate
(521) 3-Z-[1-(3-(N-methyl-N-ethyl-aminomethyl)-anilino)-1-phenyl-methylene]-6-carbamoyl-2-indolinone-trifluoroacetate
(522) 3-Z-[1-(3-(methylaminomethyl)-anilino)-1-phenyl-methylene]-6-carbamoyl-2-indolinone-trifluoroacetate
(523) 3-Z-[1-(3-hydroxymethyl-anilino)-1-phenyl-methylene]-6-carbamoyl-2-indolinone
(524) 3-Z-[1-(4-(methoxycarbonylmethyl-aminomethyl)-anilino)-1-phenyl-methylene]-6-carbamoyl-2-indolinone-trifluoroacetate
(525) 3-Z-[1-(4-(N-methylsulphonyl-N-(dimethylaminocarbonyl-methyl)-amino)-anilino)-1-phenyl-methylene]-6-carbamoyl-2-indolinone
(526) 3-Z-[1-(4-(N-acetyl-aminomethyl)-anilino)-1-phenyl-methylene]-6-carbamoyl-2-indolinone
(527) 3-Z-[1-(3,4-dimethoxy-anilino)-1-phenyl-methylene]-6-carbamoyl-2-indolinone
(528) 3-Z-[1-(4-(morpholin-4-yl)-anilino)-1-phenyl-methylene]-6-carbamoyl-2-indolinone-trifluoroacetate
(529) 3-Z-[1-(4-acetylamino-anilino)-1-phenyl-methylene]-6-carbamoyl-2-indolinone
(530) 3-Z-[1-(4-amino-anilino)-1-phenyl-methylene]-6-carbamoyl-2-indolinone
(531) 3-Z-[1-(4-N-methyl-N-acetyl-amino-anilino)-1-phenyl-methylene]-6-carbamoyl-2-indolinone
(532) 3-Z-[1-(4-ethoxycarbonyl-anilino)-1-phenyl-methylene]-6-carbamoyl-2-indolinone
(533) 3-Z-[1-(4-carboxy-anilino)-1-phenyl-methylene]-6-carbamoyl-2-indolinone
(534) 3-Z-[1-(4-benzylcarbamoyl-anilino)-1-phenyl-methylene]-6-carbamoyl-2-indolinone
(535) 3-Z-[1-(cyclohexyl-amino)-1-phenyl-methylene]-6-carbamoyl-2-indolinone
(536) 3-Z-[1-(4-amino-cyclohexyl-amino)-1-phenyl-methylene]-6-carbamoyl-2-indolinone-trifluoroacetate
(537) 3-Z-[1-(N-methyl-piperidine-4-yl-amino)-1-phenyl-methylene]-6-carbamoyl-2-indolinone-trifluoroacetate
(538) 3-Z-[1-(4-(piperidin-1-yl-methyl)-anilino)-1-methyl-methylene]-6-carbamoyl-2-indolinone-trifluoroacetate
(539) 3-Z-[1-(3-dimethylaminomethyl-anilino)-1-methyl-methylene]-6-carbamoyl-2-indolinone-trifluoroacetate
(540) 3-Z-[1-(4-(N-methyl-N-benzyl-aminomethyl)-anilino)-1-methyl-methylene]-6-carbamoyl-2-indolinone-trifluoroacetate
(541) 3-Z-[1-(4-(N-methylsulphonyl-N-(2-dimethylamino-ethyl)-amino)-anilino)-1-methyl-methylene]-6-carbamoyl-2-indolinone-trifluoroacetate
(542) 3-Z-[1-(4-chloro-anilino)-1-methyl-methylene]-6-carbamoyl-2-indolinone
(543) 3-Z-[1-(3-chloro-anilino)-1-methyl-methylene]-6-carbamoyl-2-indolinone
(544) 3-Z-[1-(4-methoxycarbonyl-anilino)-1-methyl-methylene]-6-carbamoyl-2-indolinone
(545) 3-Z-[1-(4-carboxy-anilino)-1-methyl-methylene]-6-carbamoyl-2-indolinone
(546) 3-Z-[1-(4-methyl-3-nitro-anilino)-1-methyl-methylene]-6-carbamoyl-2-indolinone
(547) 3-Z-[1-(4-(piperidin-1-yl-methyl)-anilino)-1-propyl-methylene]-6-carbamoyl-2-indolinone-trifluoroacetate
(548) 3-Z-[1-(3-dimethylaminomethyl-anilino)-1-propyl-methylene]-6-carbamoyl-2-indolinone-trifluoroacetate
(549) 3-Z-[1-(4-(N-methyl-N-benzyl-aminomethyl)-anilino)-1-propyl-methylene]-6-carbamoyl-2-indolinone-trifluoroacetate
(550) 3-Z-[1-(4-(N-methylsulphonyl-N-(2-dimethylamino-ethyl)-amino)-anilino)-1-propyl-methylene]-6-carbamoyl-2-indolinone-trifluoroacetate
(551) 3-Z-[1-(4-chloro-anilino)-1-propyl-methylene]-6-carbamoyl-2-indolinone
(552) 3-Z-[1-(3-chloro-anilino)-1-propyl-methylene]-6-carbamoyl-2-indolinone
(553) 3-Z-[1-(4-methoxycarbonyl-anilino)-1-propyl-methylene]-6-carbamoyl-2-indolinone
(554) 3-Z-[1-(4-carboxy-anilino)-1-propyl-methylene]-6-carbamoyl-2-indolinone
(555) 3-Z-[1-(4-methyl-3-nitro-anilino)-1-propyl-methylene]-6-carbamoyl-2-indolinone
(556) 3-Z-[1-(3-(piperidin-1-yl-methyl)-anilino)-1-phenyl-methylene]-6-carbamoyl-2-indolinone-trifluoroacetate
(557) 3-Z-[1-(3-(diethylaminomethyl)-anilino)-1-phenyl-methylene]-6-carbamoyl-2-indolinone-trifluoroacetate
(558) 3-Z-[1-(3-(benzylaminomethyl)-anilino)-1-phenyl-methylene]-6-carbamoyl-2-indolinone-trifluoroacetate
(559) 3-Z-[1-(3-(N-methyl-N-benzyl-aminomethyl)-anilino)-1-phenyl-methylene]-6-carbamoyl-2-indolinone-trifluoroacetate
(560) 3-Z-[1-(3-(butylaminomethyl)-anilino)-1-phenyl-methylene]-6-carbamoyl-2-indolinone-trifluoroacetate
(561) 3-Z-[1-(3-(aminomethyl)-anilino)-1-phenyl-methylene]-6-carbamoyl-2-indolinone-trifluoroacetate (562) 3-Z-[1-(3-(N-(3-dimethylaminopropyl)-N-methyl-amino-methyl)-anilino)-1-phenyl-methylene]-6-carbamoyl-2-indolinone-trifluoroacetate
(563) 3-Z-[1-(3-(N-(2-dimethylaminoethyl)-N-methyl-aminomethyl)-anilino)-1-phenyl-methylene]-6-carbamoyl-2-indolinone-trifluoroacetate
(564) 3-Z-[1-(4-(piperidin-1-yl-methyl)-anilino)-1-phenyl-methylene]-6-ethoxycarbonyl-2-indolinone
(565) 3-Z-[1-(4-bromo-anilino)-1-phenyl-methylene]-6-ethoxy-carbonyl-2-indolinone
(566) 3-Z-[1-(3-(dimethylaminomethyl)-anilino)-1-phenyl-methylene]-6-ethoxycarbonyl-2-indolinone
(567) 3-Z-[1-(4-(dimethylaminomethyl)-anilino)-1-phenyl-methylene]-6-ethoxycarbonyl-2-indolinone
(568) 3-Z-[1-(4-[(2,6-dimethyl-piperidin-1-yl)-methyl]-anilino)-1-phenyl-methylene]-6-ethoxycarbonyl-2-indolinone
(569) 3-Z-[1-(4-(2-dimethylamino-ethyl)-anilino)-1-phenyl-methylene]-6-ethoxycarbonyl-2-indolinone
(570) 3-Z-[1-(4-(N-(2-dimethylamino-ethyl)-N-acetyl-amino)-anilino)-1-phenyl-methylene]-6-ethoxycarbonyl-2-indolinone
(571) 3-Z-[1-(4-tert.butyloxycarbonyl-anilino)-1-phenyl-methylene]-6-ethoxycarbonyl-2-indolinone
(572) 3-Z-[1-(4-(N-(3-dimethylamino-propyl)-N-acetyl-amino)-anilino)-1-phenyl-methylene]-6-ethoxycarbonyl-2-indolinone
(573) 3-Z-[1-(4-(N-(2-dimethylamino-ethyl)-N-methylsulphonyl-amino)-anilino)-1-phenyl-methylene]-6-ethoxy-carbonyl-2-indolinone
(574) 3-Z-[1-(4-(4-methyl-piperazin-1-yl)-anilino)-1-phenyl-methylene]-6-ethoxycarbonyl-2-indolinone
(575) 3-Z-[1-(4-(N-(2-dimethylamino-ethyl)-N-methyl-amino)-anilino)-1-phenyl-methylene]-6-ethoxycarbonyl-2-indolinone
(576) 3-Z-[1-(4-(N-(3-dimethylamino-propyl)-N-methyl-amino)-anilino)-1-phenyl-methylene]-6-ethoxycarbonyl-2-indolinone
(577) 3-Z-[1-(4-(N-methyl-acetylamino)-anilino)-1-phenyl-methylene]-6-ethoxycarbonyl-2-indolinone
(578) 3-Z-[1-(4-(N-methyl-methylsulphonylamino)-anilino)-1-phenyl-methylene]-6-ethoxycarbonyl-2-indolinone
(579) 3-Z-[1-(4-(N-(3-dimethylamino-propyl)-N-methyl-sulphonyl-amino)-anilino)-1-phenyl-methylene]-6-ethoxycarbonyl-2-indolinone
(580) 3-Z-[1-(4-(N-dimethylaminocarbonylmethyl-N-methylsulphonyl-amino)-anilino)-1-phenyl-methylene]-6-ethoxycarbonyl-2-indolinone
(581) 3-Z-[1-(4-(imidazol-4-yl)-anilino)-1-phenyl-methylene]-6-ethoxycarbonyl-2-indolinone
(582) 3-Z-[1-(4-(tetrazol-5-yl)-anilino)-1-phenyl-methylene]-6-ethoxycarbonyl-2-indolinone
(583) 3-Z-[1-(4-(N-benzyl-N-methyl-aminomethyl)-anilino)-1-phenyl-methylene]-6-ethoxycarbonyl-2-indolinone
(584) 3-Z-[1-(4-(N-(2-dimethylamino-ethyl)-N-propionyl-amino)-anilino)-1-phenyl-methylene]-6-ethoxycarbonyl-2-indolinone
(585) 3-Z-[1-(4-(pyrrolidin-1-yl-methyl)-anilino)-1-phenyl-methylene]-6-ethoxycarbonyl-2-indolinone
(586) 3-Z-[1-(4-(N-methyl-N-phenethyl-aminomethyl)-anilino)-1-phenyl-methylene]-6-ethoxycarbonyl-2-indolinone
(587) 3-Z-[1-(4-(N-dimethylaminomethylcarbonyl-N-methyl-amino)-anilino)-1-phenyl-methylene]-6-ethoxy-carbonyl-2-indolinone
(588) 3-Z-[1-(4-(N-(2-dimethylamino-ethyl)-N-ethylsulphonyl-amino)-anilino)-1-phenyl-methylene]-6-ethoxycarbonyl-2-indolinone
(589) 3-Z-[1-(4-(N-tert.butoxycarbonyl-N-ethyl-aminomethyl)-anilino)-1-phenyl-methylene]-6-ethoxycarbonyl-2-indolinone
(590) 3-Z-[1-(4-(piperidin-1-yl-methyl)-anilino)-1-ethyl-methylene]-6-ethoxycarbonyl-2-indolinone
(591) 3-Z-[1-(4-(N-(2-dimethylamino-ethyl)-N-methylsulphonyl-amino)-anilino)-1-ethyl-methylene]-6-ethoxycarbonyl-2-indolinone
(592) 3-Z-[1-(4-(dimethylaminomethyl)-anilino)-1-phenyl-methylene]-6-methoxycarbonyl-2-indolinone
(593) 3-Z-[1-(4-[(2,6-dimethyl-piperidin-1-yl)-methyl]-anilino)-1-phenyl-methylene]-6-methoxycarbonyl-2-indolinone
(594) 3-Z-[1-(4-(N-(2-dimethylamino-ethyl)-N-methylsulphonyl-amino)-anilino)-1-phenyl-methylene]-6-methoxycarbonyl-2-indolinone
(595) 3-Z-[1-(4-(N-(3-dimethylamino-propyl)-N-methyl-sulphonyl-amino)-anilino)-1-phenyl-methylene]-6-methoxycarbonyl-2-indolinone
(596) 3-Z-[1-(4-(N-dimethylaminocarbonylmethyl-N-methylsulphonyl-amino)-anilino)-1-phenyl-methylene]-6-methoxycarbonyl-2-indolinone
(597) 3-Z-[1-(4-(N-acetyl-N-dimethylaminocarbonylmethyl-amino)-anilino)-1-phenyl-methylene]-6-methoxy-carbonyl-2-indolinone
(598) 3-Z-[1-(4-(N-dimethylaminocarbonylmethyl-amino)-anilino)-1-phenyl-methylene]-6-methoxycarbonyl-2-indolinone
(599) 3-Z-[1-(4-(N-(3-dimethylamino-propyl)-N-acetyl-amino)-anilino)-1-phenyl-methylene]-6-methoxycarbonyl-2-indolinone
(600) 3-Z-[1-(4-(N-methylaminocarbonylmethyl-N-methylsulphonyl-amino)-anilino)-1-phenyl-methylene]-6-methoxycarbonyl-2-indolinone
(601) 3-Z-[1-(4-((imidazolidin-2,4-dion-5-ylidene)-methyl)-anilino)-1-phenyl-methylene]-6-methoxycarbonyl-2-indolinone
(602) 3-Z-[1-(4-(N-((2-dimethylamino-ethyl)-carbonyl)-N-methyl-amino)-anilino)-1-phenyl-methylene]-6-methoxycarbonyl-2-indolinone
(603) 3-Z-[1-(4-(N-tert.butoxycarbonyl-aminomethyl)-anilino)-1-phenyl-methylene]-6-methoxycarbonyl-2-indolinone
(604) 3-Z-[1-(4-(2-oxo-pyrrolidin-1-yl-methyl)-anilino)-1-phenyl-methylene]-6-methoxycarbonyl-2-indolinone
(605) 3-Z-[1-(4-(N-aminocarbonylmethyl-N-methylsulphonyl-amino)-anilino)-1-phenyl-methylene]-6-methoxycarbonyl-2-indolinone
(606) 3-Z-[1-(4-(thiomorpholin-4-yl-methyl)-anilino)-1-phenyl-methylene]-6-methoxycarbonyl-2-indolinone
(607) 3-Z-[1-(4-(1,1-dioxo-thiomorpholin-4-yl-methyl)-anilino)-1-phenyl-methylene]-6-methoxycarbonyl-2-indolinone
(608) 3-Z-[1-(4-(N-cyanomethyl-N-methylsulphonyl-amino)-anilino)-1-phenyl-methylene]-6-methoxycarbonyl-2-indolinone
(609) 3-Z-[1-(4-(N-tert.butoxycarbonyl-ethylaminomethyl)-anilino)-1-phenyl-methylene]-6-methoxycarbonyl-2-indolinone
(610) 3-Z-[1-(4-(N-benzyl-N-methyl-aminomethyl)-anilino)-1-phenyl-methylene]-6-methoxycarbonyl-2-indolinone (611) 3-Z-[1-(4-(1-oxo-thiomorpholin-4-yl-methyl)-anilino)-1-phenyl-methylene]-6-methoxycarbonyl-2-indolinone
(612) 3-Z-[1-(4-(2-(imidazol-4-yl)-ethyl)-anilino)-1-phenyl-methylene]-6-methoxycarbonyl-2-indolinone
(613) 3-Z-[1-(4-(morpholin-4-yl-methyl)-anilino)-1-phenyl-methylene]-6-methoxycarbonyl-2-indolinone
(614) 3-Z-[1-(4-((4-methyl-piperazin-1-yl)-methyl)-anilino)-1-phenyl-methylene]-6-methoxycarbonyl-2-indolinone
(615) 3-Z-[1-(4-((2-(N-benzyl-N-methyl-amino)-ethyl)-N-methylsulphonyl-amino)-anilino)-1-phenyl-methylene]-6-methoxycarbonyl-2-indolinone
(616) 3-Z-[1-(4-cyclohexylamino-anilino)-1-phenyl-methylene]-6-methoxycarbonyl-2-indolinone
(617) 3-Z-[1-(4-(pyridin-4-yl-methyl)-anilino)-1-phenyl-methylene]-6-methoxycarbonyl-2-indolinone
(618) 3-Z-[1-(4-(imidazol-1-yl-methyl)-anilino)-1-phenyl-methylene]-6-methoxycarbonyl-2-indolinone
(619) 3-Z-[1-(4-(imidazol-1-yl-methyl)-anilino)-1-phenyl-methylene]-6-methoxycarbonyl-2-indolinone
(620) 3-Z-[1-(N-methyl-piperidine-4-yl-amino)-1-phenyl-methylene]-6-methoxycarbonyl-2-indolinone
(621) 3-Z-[1-(4-(imidazol-4-yl-methyl)-anilino)-1-phenyl-methylene]-6-methoxycarbonyl-2-indolinone
(622) 3-Z-[1-(4-((4-hydroxy-piperidin-1-yl))-methyl)-anilino)-1-phenyl-methylene]-6-methoxycarbonyl-2-indolinone
(623) 3-Z-[1-(4-((4-methoxy-piperidin-1-yl)-methyl)-anilino)-1-phenyl-methylene]-6-methoxycarbonyl-2-indolinone
(624) 3-Z-[1-(4-benzyl-anilino)-1-phenyl-methylene]-6-methoxycarbonyl-2-indolinone
(625) 3-Z-[1-(4-(N-(3-trifluoroacetylamino-propyl)-N-methylsulphonyl-amino)-anilino)-1-phenyl-methylene]-6-methoxycarbonyl-2-indolinone
(626) 3-Z-[1-(4-tert.butoxycarbonylmethyl-anilino)-1-phenyl-methylene]-6-ethoxycarbonyl-2-indolinone
(627) 3-Z-[1-(4-tert.butoxycarbonyl-anilino)-1-ethyl-methylene]-6-ethoxycarbonyl-2-indolinone
(628) 3-Z-[1-(4-(4-tert.butoxycarbonyl-piperazin-1-yl-methyl)-anilino)-1-phenyl-methylene]-6-methoxycarbonyl-2-indolinone
(629) 3-Z-[1-(4-(1-methyl-imidazol-2-yl)-anilino)-1-phenyl-methylene]-6-methoxycarbonyl-2-indolinone
(630) 3-Z-[1-(4-(N-(2-dimethylamino-ethyl)-N-methylsulphonyl-amino)-3-nitro-anilino)-1-phenyl-methylene]-6-methoxycarbonyl-2-indolinone
(631) 3-Z-[1-(4-(N-(2-dimethylamino-ethyl)-N-methylsulphonyl-amino)-3-amino-anilino)-1-phenyl-methylene]-6-methoxycarbonyl-2-indolinone
(632) 3-Z-[1-(4-((3-(N-benzyl-N-methyl-amino)-propyl)-N-methylsulphonyl-amino)-anilino)-1-phenyl-methylene]-6-methoxycarbonyl-2-indolinone
(633) 3-Z-[1-(4-(N-(2-dimethylamino-ethyl)-N-methylsulphonyl-amino)-3-chloro-anilino)-1-phenyl-methylene]-6-methoxycarbonyl-2-indolinone
(634) 3-Z-[1-(4-(N-dimethylaminomethylcarbonyl-N-methyl-amino)-anilino)-1-phenyl-methylene]-6-methoxycarbonyl-2-indolinone
(635) 3-Z-[1-(4-(N-(2-dimethylamino-ethyl)-N-acetyl-amino)-anilino)-1-phenyl-methylene]-6-methoxycarbonyl-2-indolinone
(636) 3-Z-[1-(4-(N-(2-dimethylamino-ethyl)-N-propionyl-amino)-anilino)-1-phenyl-methylene]-6-methoxycarbonyl-2-indolinone
(637) 3-Z-[1-(4-(N-(2-dimethylamino-ethyl)-N-butyryl-amino)-anilino)-1-phenyl-methylene]-6-methoxycarbonyl-2-indolinone
(638) 3-Z-[1-(4-(N-(2-dimethylamino-ethyl)-N-isobutyryl-amino)-anilino)-1-phenyl-methylene]-6-methoxycarbonyl-2-indolinone
(639) 3-Z-[1-(4-(N-(2-dimethylamino-ethyl)-N-benzoyl-amino)-anilino)-1-phenyl-methylene]-6-methoxycarbonyl-2-indolinone
(640) 3-Z-[1-(4-(N-(2-dimethylamino-ethyl)-N-acetyl-amino)-3-amino-anilino)-1-phenyl-methylene]-6-methoxycarbonyl-2-indolinone
(641) 3-Z-[1-(4-(4-hydroxymethyl-piperidin-1-yl-methyl)-anilino)-1-phenyl-methylene]-6-methoxycarbonyl-2-indolinone
(642) 3-Z-[1-(4-(2-(4-hydroxy-piperidin-1-yl)-ethyl)-anilino)-1-phenyl-methylene]-6-methoxycarbonyl-2-indolinone
(643) 3-Z-[1-(4-(N-(2-dimethylamino-ethyl)-N-propylsulphonyl-amino)-anilino)-1-phenyl-methylene]-6-methoxycarbonyl-2-indolinone
(644) 3-Z-[1-(4-(N-(2-dimethylamino-ethyl)-N-butylsulphonyl-amino)-anilino)-1-phenyl-methylene]-6-methoxycarbonyl-2-indolinone
(645) 3-Z-[1-(4-(N-(2-dimethylamino-ethyl)-N-phenylsulphonyl-amino)-anilino)-1-phenyl-methylene]-6-methoxycarbonyl-2-indolinone
(646) 3-Z-[1-(4-(N-(2-dimethylamino-ethyl)-N-benzylsulphonyl-amino)-anilino)-1-phenyl-methylene]-6-methoxycarbonyl-2-indolinone
(647) 3-Z-[1-(4-(N-(2-dimethylamino-ethyl)-N-ethylsulphonyl-amino)-anilino)-1-phenyl-methylene]-6-methoxycarbonyl-2-indolinone
(648) 3-Z-[1-(4-((imidazolidin-2,4-dion-5-yl)-methyl)-anilino)-1-phenyl-methylene]-6-methoxycarbonyl-2-indolinone
(649) 3-Z-[1-(4-((3-hydroxy-pyrrolidin-1-yl)-methyl)-anilino)-1-phenyl-methylene]-6-methoxycarbonyl-2-indolinone
(650) 3-Z-[1-(4-(cyclohexylyl-methyl)-anilino)-1-phenyl-methylene]-6-methoxycarbonyl-2-indolinone
(651) 3-Z-[1-(4-(cyclohexyl-carbonyl)-anilino)-1-phenyl-methylene]-6-methoxycarbonyl-2-indolinone
(652) 3-Z-[1-(4-diethylaminomethyl-anilino)-1-phenyl-methylene]-6-methoxycarbonyl-2-indolinone
(653) 3-Z-[1-(4-(N-(n-hexyl)-N-methyl-aminomethyl)-anilino)-1-phenyl-methylene]-6-methoxycarbonyl-2-indolinone
(654) 3-Z-[1-(4-(N-(2-dimethylamino-ethyl)-N-(furan-2-carbonyl)-amino)-anilino)-1-phenyl-methylene]-6-methoxycarbonyl-2-indolinone
(655) 3-Z-[1-(4-(N-(2-dimethylamino-ethyl)-N-(2-methoxy-benzoyl)-amino)-anilino)-1-phenyl-methylene]-6-methoxy-carbonyl-2-indolinone
(656) 3-Z-[1-(4-(N-(2-dimethylamino-ethyl)-N-(pyridine-3-carbonyl)-amino)-anilino)-1-phenyl-methylene]-6-methoxycarbonyl-2-indolinone
(657) 3-Z-[1-(4-(N-(2-dimethylamino-ethyl)-N-(phenyl-acetyl)-amino)-anilino)-1-phenyl-methylene]-6-methoxycarbonyl-2-indolinone
(658) 3-Z-[1-(4-(N-ethyl-N-methyl-aminomethyl)-anilino)-1-phenyl-methylene]-6-methoxycarbonyl-2-indolinone
(659) 3-Z-[1-(4-(imidazol-2-yl)-anilino)-1-phenyl-methylene]-6-methoxycarbonyl-2-indolinone
(660) 3-Z-[1-(4-(1-ethyl-imidazol-2-yl)-anilino)-1-phenyl-methylene]-6-methoxycarbonyl-2-indolinone (661) 3-Z-[1-(4-(1-benzyl-imidazol-2-yl)-anilino)-1-phenyl-methylene]-6-methoxycarbonyl-2-indolinone
(662) 3-Z-[1-(4-(N-(2-dimethylamino-ethyl)-N-isopropyl-sulphonyl-amino)-anilino)-1-phenyl-methylene]-6-methoxycarbonyl-2-indolinone
(663) 3-Z-[1-(4-(N-(piperidin-1-yl-methylcarbonyl)-N-methyl-amino)-anilino)-1-phenyl-methylene]-6-methoxycarbonyl-2-indolinone
(664) 3-Z-[1-(4-(N-(morpholin-4-yl-methylcarbonyl)-N-methyl-amino)-anilino)-1-phenyl-methylene]-6-methoxycarbonyl-2-indolinone
(665) 3-Z-[1-(4-(N-((4-benzyl-piperazin-1-yl)-methylcarbonyl)-N-methyl-amino)-anilino)-1-phenyl-methylene]-6-methoxycarbonyl-2-indolinone
(666) 3-Z-[1-(4-(N-(pyrrolidin-1-yl-methylcarbonyl)-N-methyl-amino)-anilino)-1-phenyl-methylene]-6-methoxycarbonyl-2-indolinone
(667) 3-Z-[1-(4-(N-(2-dimethylamino-ethyl)-N-acetyl-amino)-3-bromo-anilino)-1-phenyl-methylene]-6-methoxycarbonyl-2-indolinone
(668) 3-Z-[1-(4-(5-methyl-imidazol-4-yl)-anilino)-1-phenyl-methylene]-6-methoxycarbonyl-2-indolinone
(669) 3-Z-[1-(4-(N-((2-dimethylamino-ethyl)-carbonyl)-N-isopropyl-amino)-anilino)-1-phenyl-methylene]-6-methoxycarbonyl-2-indolinone
(670) 3-Z-[1-(4-(N-((2-dimethylamino-ethyl)-carbonyl)-N-benzyl-amino)-anilino)-1-phenyl-methylene]-6-methoxycarbonyl-2-indolinone
(671) 3-Z-[1-(4-(N-butyl-N-tert.butoxycarbonyl-aminomethyl)-anilino)-1-phenyl-methylene]-6-methoxycarbonyl-2-indolinone
(672) 3-Z-[1-(4-(N-((N-aminocarbonylmethyl-N-methyl-amino)-methylcarbonyl)-N-methyl-amino)-anilino)-1-phenyl-methylene]-6-methoxycarbonyl-2-indolinone
(673) 3-Z-[1-(4-(N-((N-benzyl-N-methyl-amino)-methylcarbonyl)-N-methyl-amino)-anilino)-1-phenyl-methylene]-6-methoxycarbonyl-2-indolinone
(674) 3-Z-[1-(4-(N-(di-(2-methoxyethyl)-amino-methylcarbonyl)-N-methyl-amino)-anilino)-1-phenyl-methylene]-6-methoxycarbonyl-2-indolinone
(675) 3-Z-[1-(4-(N-((2-(4-tert.butoxycarbonyl-piperazin-1-yl)-ethyl)-carbonyl)-N-methyl-amino)-anilino)-1-phenyl-methylene]-6-methoxycarbonyl-2-indolinone
(676) 3-Z-[1-(4-(N-((2-(piperidin-1-yl)-ethyl)-carbonyl)-N-methyl-amino)-anilino)-1-phenyl-methylene]-6-methoxycarbonyl-2-indolinone
(677) 3-Z-[1-(4-(N-((2-(N-benzyl-N-methyl-amino)-ethyl)-carbonyl)-N-methyl-amino)-anilino)-1-phenyl-methylene]-6-methoxycarbonyl-2-indolinone
(678) 3-Z-[1-(4-(N-dimethylaminomethylcarbonyl-N-isopropyl-amino)-anilino)-1-phenyl-methylene]-6-methoxycarbonyl-2-indolinone
(679) 3-Z-[1-(4-(N-(piperidin-1-yl-methylcarbonyl)-N-isopropyl-amino)-anilino)-1-phenyl-methylene]-6-methoxycarbonyl-2-indolinone
(680) 3-Z-[1-(4-(N-((4-tert.butoxycarbonyl-piperazin-1-yl)-methylcarbonyl)-N-isopropyl-amino)-anilino)-1-phenyl-methylene]-6-methoxycarbonyl-2-indolinone
(681) 3-Z-[1-(4-(N-((N-benzyl-N-methyl-amino)-methylcarbonyl)-N-benzyl-amino)-anilino)-1-phenyl-methylene]-6-methoxycarbonyl-2-indolinone
(682) 3-Z-[1-(4-(N-dimethylaminomethylcarbonyl-N-benzyl-amino)-anilino)-1-phenyl-methylene]-6-methoxycarbonyl-2-indolinone
(683) 3-Z-[1-(4-(N-(piperidin-1-yl-methylcarbonyl)-N-benzyl-amino)-anilino)-1-phenyl-methylene]-6-methoxycarbonyl-2-indolinone
(684) 3-Z-[1-(4-(1,2,4-triazol-2-yl-methyl)-anilino)-1-phenyl-methylene]-6-methoxycarbonyl-2-indolinone
(685) 3-Z-[1-(4-(1,2,3-triazol-2-yl-methyl)-anilino)-1-phenyl-methylene]-6-methoxycarbonyl-2-indolinone
(686) 3-Z-[1-(4-(1,2,3-triazol-1-yl-methyl)-anilino)-1-phenyl-methylene]-6-methoxycarbonyl-2-indolinone
(687) 3-Z-[1-(4-((N-aminocarbonylmethyl-N-methyl-amino)-methyl)-anilino)-1-phenyl-methylene]-6-methoxycarbonyl-2-indolinone
(688) 3-Z-[1-(4-((di-(2-methoxy-ethyl)-amino)-methyl)-anilino)-1-phenyl-methylene]-6-methoxycarbonyl-2-indolinone
(689) 3-Z-[1-(4-(pyrrolidin-1-yl-methyl)-anilino)-1-phenyl-methylene]-6-methoxycarbonyl-2-indolinone
(690) 3-Z-[1-(4-((di-(2-hydroxy-ethyl)-amino)-methyl)-anilino)-1-phenyl-methylene]-6-methoxycarbonyl-2-indolinone
(691) 3-Z-[1-(4-((N-ethoxycarbonylmethyl-N-methyl-amino)-methyl)-anilino)-1-phenyl-methylene]-6-methoxycarbonyl-2-indolinone
(692) 3-Z-[1-(4-(azetidin-1-yl-methyl)-anilino)-1-phenyl-methylene]-6-methoxycarbonyl-2-indolinone
(693) 3-Z-[1-(4-(N-propyl-N-tert.butoxycarbonyl-aminomethyl)-anilino)-1-phenyl-methylene]-6-methoxycarbonyl-2-indolinone
(694) 3-Z-[1-(4((N-(2-(2-methoxy-ethoxy)-ethyl)-N-methyl-amino)-methyl)-anilino)-1-phenyl-methylene]-6-methoxycarbonyl-2-indolinone
(695) 3-Z-[1-(4-((N-(tert.butoxycarbonyl-3-amino-propyl)-N-methyl-amino)-methyl)-anilino)-1-phenyl-methylene]-6-methoxycarbonyl-2-indolinone
(696) 3-Z-[1-(4-((N-(methylcarbamoyl-methyl)-N-methyl-amino)-methyl)-anilino)-1-phenyl-methylene]-6-methoxycarbonyl-2-indolinone
(697) 3-Z-[1-(4-((N-(dimethylcarbamoyl-methyl)-N-methyl-amino)-methyl)-anilino)-1-phenyl-methylene]-6-methoxycarbonyl-2-indolinone
(698) 3-Z-[1-(4-methyl-anilino)-1-phenyl-methylene]-6-methoxycarbonyl-2-indolinone
(699) 3-Z-[1-(4-((N-propyl-N-methyl-amino)-methyl)-anilino)-1-phenyl-methylene]-6-methoxycarbonyl-2-indolinone
(700) 3-Z-[1-(4-((N-(2-hydroxy-ethyl)-N-methyl-amino)-methyl)-anilino)-1-phenyl-methylene]-6-methoxycarbonyl-2-indolinone
(701) 3-Z-[1-(4-((N-(2-dimethylamino-ethyl)-N-methyl-amino)-methyl)-anilino)-1-phenyl-methylene]-6-methoxycarbonyl-2-indolinone
(702) 3-Z-[1-(4-((N-(3-dimethylamino-propyl)-N-methyl-amino)-methyl)-anilino)-1-phenyl-methylene]-6-methoxycarbonyl-2-indolinone
(703) 3-Z-[1-(4-(3-oxo-piperazin-1-yl-methyl)-anilino)-1-phenyl-methylene]-6-methoxycarbonyl-2-indolinone
(704) 3-Z-[1-(4-carboxy-anilino)-1-phenyl-methylene]-6-ethoxy-carbonyl-2-indolinone
(705) 3-Z-[1-(4-aminomethyl-anilino)-1-phenyl-methylene]-6-methoxycarbonyl-2-indolinone
(706) 3-Z-[1-(4-ethylaminomethyl-anilino)-1-phenyl-methylene]-6-methoxycarbonyl-2-indolinone
(707) 3-Z-[1-(4-carboxymethyl-anilino)-1-phenyl-methylene]-6-ethoxycarbonyl-2-indolinone
(708) 3-Z-[1-(4-carboxy-anilino)-1-ethyl-methylene]-6-ethoxy-carbonyl-2-indolinone
(709) 3-Z-[1-(4-(piperazin-1-yl-methyl)-anilino)-1-phenyl-methylene]-6-methoxycarbonyl-2-indolinone
(710) 3-Z-[1-(4-butylaminomethyl-anilino)-1-phenyl-methylene]-6-methoxycarbonyl-2-indolinone (711) 3-Z-[1-(4-ethylaminomethyl-anilino)-1-phenyl-methylene]-6-ethoxycarbonyl-2-indolinone (712) 3-Z-[1-(4-ethylaminomethyl-anilino)-1-phenyl-methylene]-6-carbamoyl-2-indolinone (713) 3-Z-[1-(4-(N-(piperazin-1-yl-methylcarbonyl)-N-isopropyl-amino)-anilino)-1-phenyl-methylene]-6-methoxycarbonyl-2-indolinone (714) 3-Z-[1-(4-(N-((2-(piperazin-1-yl)-ethyl)-carbonyl)-N-methyl-amino)-anilino)-1-phenyl-methylene]-6-methoxycarbonyl-2-indolinone (715) 3-Z-[1-(4-(N-propyl-aminomethyl)-anilino)-1-phenyl-methylene]-6-methoxycarbonyl-2-indolinone (716) 3-Z-[1-(4-((N-(3-amino-propyl)-N-methyl-amino)-methyl)-anilino)-1-phenyl-methylene]-6-methoxycarbonyl-2-indolinone (717) 3-Z-[1-(4-(2-dimethylamino-ethoxy)-anilino)-1-phenyl-methylene]-6-methoxycarbonyl-2-indolinone (718) 3-Z-[1-(3-cyano-4-(N-dimethylaminomethylcarbonyl-N-methyl-amino)-anilino)-1-phenyl-methylene]-6-methoxycarbonyl-2-indolinone (719) 3-Z-[1-(3-methoxy-4-(N-dimethylaminomethylcarbonyl-N-methyl-amino)-anilino)-1-phenyl-methylene]-6-methoxycarbonyl-2-indolinone (720) 3-Z-[1-(4-(N-aminomethylcarbonyl-N-methyl-amino)-anilino)-1-phenyl-methylene]-6-methoxycarbonyl-2-indolinone (721) 3-Z-[1-(4-(N-(N-(2-dimethylamino-ethyl)-N-methyl-aminomethylcarbonyl)-N-methyl-amino)-anilino)-1-phenyl-methylene]-6-methoxycarbonyl-2-indolinone (722) 3-Z-[1-(4-(N-(di-(2-hydroxy-ethyl)-amino-methylcarbonyl)-N-methyl-amino)-anilino)-1-phenyl-methylene]-6-methoxycarbonyl-2-indolinone (723) 3-Z-[1-(4-(N-(imidazol-1-yl-methylcarbonyl)-N-methyl-amino)-anilino)-1-phenyl-methylene]-6-methoxycarbonyl-2-indolinone (724) 3-Z-[1-(4-(N-dimethylaminomethylcarbonyl-amino)-anilino)-1-phenyl-methylene]-6-methoxycarbonyl-2-indolinone (725) 3-Z-[1-(4-(N-((4-methyl-[1,4]diazepan-1-yl)-methylcarbonyl)-N-methyl-amino)-anilino)-1-phenyl-methylene]-6-methoxycarbonyl-2-indolinone (726) 3-Z-[1-(4-(N-((1-methyl-piperidin-4-yl)-methylcarbonyl)-N-methyl-amino)-anilino)-1-phenyl-methylene]-6-methoxycarbonyl-2-indolinone (727) 3-Z-[1-(2,3-dimethyl-4-(N-((4-methyl-piperazin-1-yl)-methylcarbonyl)-amino)-anilino)-1-phenyl-methylene]-6-methoxycarbonyl-2-indolinone (728) 3-Z-[1-(4-(N-((4-methyl-piperazin-1-yl)-methylcarbonyl)-amino)-anilino)-1-phenyl-methylene]-6-methoxycarbonyl-2-indolinone (729) 3-Z-[1-(4-(N-((4-methyl-piperazin-1-yl)-carbonyl)-N-methyl-amino)-anilino)-1-phenyl-methylene]-6-methoxycarbonyl-2-indolinone (730) 3-Z-[1-(4-(N-(3-dimethylamino-propyl)-N-acetyl-amino)-anilino)-1-phenyl-methylene]-6-methoxycarbonyl-2-indolinone (731) 3-Z-[1-(4-(N-((3-dimethylamino-propyl)-aminocarbonyl)-N-methyl-amino)-anilino)-1-phenyl-methylene]-6-methoxycarbonyl-2-indolinone (732) 3-Z-[1-anilino-1-phenyl-methylene]-6-methoxycarbonyl-2-indolinone (733) 3-Z-[1-(4-(N-methyl-N-methylsulphonyl-amino)-anilino)-1-phenyl-methylene]-6-methoxycarbonyl-2-indolinone (734) 3-Z-[1-cyclohexylamino-1-phenyl-methylene]-6-methoxycarbonyl-2-indolinone (735) 3-Z-[1-(4-(4-methylpiperazin-1-yl-methyl)-anilino)-1-phenyl-methylene]-6-carboxy-2-indolinone (736) 3-Z-[1-(4-methylaminomethyl-anilino)-1-phenyl-methylene]-6-carboxy-2-indolinone (737) 3-Z-[1-(4-(morpholin-4-yl-methyl)-anilino)-1-phenyl-methylene]-6-carboxy-2-indolinone (738) 3-Z-[1-(4-(N-(2-dimethylamino-ethyl)-N-methylsulphonyl-amino)-anilino)-1-phenyl-methylene]-6-carboxy-2-indolinone (739) 3-Z-[1-(4-(di-(2-hydroxy-ethyl)-amino-methyl)-anilino)-1-phenyl-methylene]-6-carboxy-2-indolinone (740) 3-Z-[1-(4-(N-((4-methyl-piperazin-1-yl)-methylcarbonyl)-N-methyl-amino)-anilino)-1-phenyl-methylene]-6-carboxy-2-indolinone (741) 3-Z-[1-(4-(N-(morpholin-4-yl-methylcarbonyl)-N-methyl-amino)-anilino)-1-phenyl-methylene]-6-carboxy-2-indolinone (742) 3-Z-[1-(4-(N-(N-(2-dimethylamino-ethyl)-N-methyl-aminomethylcarbonyl)-N-methyl-amino)-anilino)-1-phenyl-methylene]-6-carboxy-2-indolinone (743) 3-Z-[1-(4-(2-dimethylamino-ethoxy)-anilino)-1-phenyl-methylene]-6-carboxy-2-indolinone (744) 3-Z-[1-cyclohexylamino-1-phenyl-methylene]-6-carboxy-2-indolinone (745) 3-Z-[1-(4-dimethylaminomethyl-anilino)-1-(3-(2-carboxy-ethyl)-phenyl)-methylene]-6-methoxycarbonyl-2-indolinone (746) 3-Z-[1-(4-(2-dimethylamino-ethyl)-anilino)-1-(3-(2-carboxy-ethyl)-phenyl)-methylene]-6-methoxycarbonyl-2-indolinone (747) 3-Z-[1-(4-(1-methyl-imidazol-2-yl)-anilino)-1-(3-(2-carboxy-ethyl)-phenyl)-methylene]-6-methoxycarbonyl-2-indolinone (748) 3-Z-[1-(4-dimethylaminomethyl-anilino)-1-(4-(2-carboxy-ethyl)-phenyl)-methylene]-6-methoxycarbonyl-2-indolinone (749) 3-Z-[1-(4-(2-dimethylamino-ethyl)-anilino)-1-phenyl-methylene]-6-ethylmethylcarbamoyl-2-indolinone (750) 3-Z-[1-(4-dimethylaminomethyl-anilino)-1-phenyl-methylene]-6-ethylmethylcarbamoyl-2-indolinone (751) 3-Z-[1-((1-methyl-piperidin-4-yl)-amino-1-phenyl-methylene]-6-ethylmethylcarbamoyl-2-indolinone (752) 3-Z-[1-(trans-4-dimethylamino-cyclohexylamino)-1-phenyl-methylene]-6-ethylmethylcarbamoyl-2-indolinone (753) 3-Z-[1-(4-(2-diethylamino-ethoxy)-anilino)-1-phenyl-methylene]-6-ethylmethylcarbamoyl-2-indolinone (754) 3-Z-[1-(4-(N-(3-dimethylamino-propyl)-N-propionyl-amino)-anilino)-1-phenyl-methylene]-6-ethylmethylcarbamoyl-2-indolinone (755) 3-Z-[1-(4-(N-((4-methyl-piperazin-1-yl)-methylcarbonyl)-N-methyl-amino)-anilino)-1-phenyl-methylene]-6-ethylmethylcarbamoyl-2-indolinone (756) 3-Z-[1-cyclohexylamino-1-phenyl-methylene]-6-ethylmethylcarbamoyl-2-indolinone (757) 3-Z-[1-(4-(N-(2-dimethylamino-ethyl)-N-acetyl-amino)-anilino)-1-phenyl-methylene]-6-ethylmethylcarbamoyl-2-indolinone (758) 3-Z-[1-(3-diethylaminomethyl-anilino)-1-phenyl-methylene]-6-ethylmethylcarbamoyl-2-indolinone (759) 3-Z-[1-(4-(N-dimethylaminomethylcarbonyl-N-methyl-amino)-anilino)-1-phenyl-methylene]-6-ethylmethylcarbamoyl-2-indolinone (760) 3-Z-[1-(4-(N-(2-dimethylamino-ethyl)-N-methylsulphonyl-amino)-anilino)-1-phenyl-methylene]-6-ethylmethylcarbamoyl-2-indolinone (761) 3-Z-[1-anilino-1-phenyl-methylene]-6-ethylmethylcarbamoyl-2-indolinone
(762) 3-Z-[1-(4-ethylaminomethyl-anilino)-1-phenyl-methylene]-6-ethylmethylcarbamoyl-2-indolinone
(763) 3-Z-[1-(4-((2-diethylamino-ethyl)-anilino)-1-phenyl-methylene]-6-ethylmethylcarbamoyl-2-indolinone
(764) 3-Z-[1-(4-(N-(3-dimethylamino-propyl)-N-acetyl-amino)-anilino)-1-phenyl-methylene]-6-ethylmethylcarbamoyl-2-indolinone
(765) 3-Z-[1-(4-(N-methyl-N-methylsulphonyl-amino)-anilino)-1-phenyl-methylene]-6-ethylmethylcarbamoyl-2-indolinone
(766) 3-Z-[1-(4-methoxycarbonyl-anilino)-1-phenyl-methylene]-6-ethylmethylcarbamoyl-2-indolinone
(767) 3-Z-[1-(4-carboxy-anilino)-1-phenyl-methylene]-6-ethylmethylcarbamoyl-2-indolinone
(768) 3-Z-[1-(4-(N-(dimethylamino-carbonylmethyl)-N-methylsulphonyl-amino)-anilino)-1-phenyl-methylene]-6-ethylmethylcarbamoyl-2-indolinone
(769) 3-Z-[1-(4-(2-dimethylamino-ethoxy)-anilino)-1-phenyl-methylene]-6-ethylcarbamoyl-2-indolinone
(770) 3-Z-[1-(4-(N-((4-methyl-piperazin-1-yl)-methylcarbonyl)-N-methyl-amino)-anilino)-1-phenyl-methylene]-6-ethylcarbamoyl-2-indolinone
(771) 3-Z-[1-(4-(N-(2-dimethylamino-ethyl)-N-methylsulphonyl-amino)-anilino)-1-phenyl-methylene]-6-ethylcarbamoyl-2-indolinone
(772) 3-Z-[1-(4-(2-dimethylamino-ethoxy)-anilino)-1-phenyl-methylene]-6-ethylmethylcarbamoyl-2-indolinone
(773) 3-Z-[1-(4-(N-dimethylaminomethylcarbonyl-N-methyl-amino)-anilino)-1-phenyl-methylene]-6-ethylcarbamoyl-2-indolinone
(774) 3-Z-[1-(4-dimethylaminomethyl-anilino)-1-phenyl-methylene]-6-ethylcarbamoyl-2-indolinone
(775) 3-Z-[1-(4-(N-(2-dimethylamino-ethyl)-N-acetyl-amino)-anilino)-1-phenyl-methylene]-6-ethylcarbamoyl-2-indolinone
(776) 3-Z-[1-(4-(N-(3-dimethylamino-propyl)-N-acetyl-amino)-anilino)-1-phenyl-methylene]-6-ethylcarbamoyl-2-indolinone
(777) 3-Z-[1-(4-carbamoyl-anilino)-1-phenyl-methylene]-6-ethylmethylcarbamoyl-2-indolinone
(778) 3-Z-[1-(4-(N-(2-diethylamino-ethyl)-carbamoyl)-anilino)-1-phenyl-methylene]-6-ethylmethylcarbamoyl-2-indolinone
(779) 3-Z-[1-(4-((4-methyl-piperazin-1-yl)-carbonyl)-anilino)-1-phenyl-methylene]-6-ethylmethylcarbamoyl-2-indolinone
(780) 3-Z-[1-(4-((4-methyl-piperazin-1-yl)-carbonyl)-anilino)-1-phenyl-methylene]-6-ethylcarbamoyl-2-indolinone
(781) 3-Z-[1-(4-((4-ethyl-piperazin-1-yl)-carbonyl)-anilino)-1-phenyl-methylene]-6-ethylmethylcarbamoyl-2-indolinone
(782) 3-Z-[1-(4-(N-ethyl-N-(2-dimethylamino-ethyl)-carbamoyl)-anilino)-1-phenyl-methylene]-6-ethylmethylcarbamoyl-2-indolinone
(783) 3-Z-[1-(4-(N-((4-methyl-piperazin-1-yl)-methylcarbonyl)-N-methyl-amino)-anilino)-1-phenyl-methylene]-6-diethylcarbamoyl-2-indolinone
(784) 3-Z-[1-(4-((cis-3,5-dimethyl-piperazin-1-yl)-carbonyl)-anilino)-1-phenyl-methylene]-6-ethylmethylcarbamoyl-2-indolinone
(785) 3-Z-[1-(4-((4-ethyl-piperazin-1-yl)-carbonyl)-anilino)-1-phenyl-methylene]-6-ethylcarbamoyl-2-indolinone
(786) 3-Z-[1-(4-(N-(2-diethylamino-ethyl)-carbamoyl)-anilino)-1-phenyl-methylene]-6-ethylmethylcarbamoyl-2-indolinone
(787) 3-Z-[1-(4-((cis-3,5-dimethyl-piperazin-1-yl)-carbonyl)-anilino)-1-phenyl-methylene]-6-ethylcarbamoyl-2-indolinone
(788) 3-Z-[1-(4-(N-(3-dimethylamino-propyl)-N-methylsulphonyl-amino)-anilino)-1-phenyl-methylene]-6-ethylcarbamoyl-2-indolinone
(789) 3-Z-[1-(4-(N-dimethylaminomethylcarbonyl-N-methyl-amino)-anilino)-methylene]-6-methoxycarbonyl-2-indolinone
(790) 3-Z-[1-(4-dimethylaminomethyl-anilino)-methylene]-6-methoxycarbonyl-2-indolinone
(791) 3-Z-[1-(4-(N-((4-methyl-piperazin-1-yl)-methylcarbonyl)-N-methyl-amino)-anilino)-methylene]-6-methoxycarbonyl-2-indolinone
(792) 3-Z-[1-(4-(N-((4-methyl-piperazin-1-yl)-methylcarbonyl)-N-methyl-amino)-anilino)-methylene]-6-ethylcarbamoyl-2-indolinone
(793) 3-Z-[1-(4-dimethylaminomethyl-anilino)-methylene]-6-ethylcarbamoyl-2-indolinone
(794) 3-Z-[1-(4-(piperidin-1-yl-methyl)-anilino)-methylene]-6-ethylcarbamoyl-2-indolinone
(795) 3-Z-[1-(4-(N-(3-dimethylamino-propyl)-N-acetyl-amino)-anilino)-methylene]-6-ethylcarbamoyl-2-indolinone as well as their tautomers, their stereoisomers or the physiologically acceptable salts thereof.

The compounds of general formula I, their tautomers, their stereoisomers or the physiologically acceptable salts thereof are thus suitable for the prevention or treatment of a specific fibrotic disease selected from the group consisting of:

Fibrosis and remodeling of lung tissue in chronic obstructive pulmonary disease (COPD), chronic bronchitis, and emphysema;

Lung fibrosis and pulmonary diseases with a fibrotic component including but not limited to idiopathic pulmonary fibrosis (IPF), giant cell interstitial pneumonia (GIP), sarcodosis, cystic fibrosis, respiratory distress syndrome (ARDS), granulomatosis, silicosis, drug-induced lung fibrosis (for example, induced by drugs such as bleomycin, bis-chloronitrosourea, cyclophosphamide, amiodarone, procainamide, penicillamine, gold or nitrofurantoin), silicosis, asbestosis, systemic scleroderma;

Fibrosis and remodeling in asthma;

Fibrosis in rheumatoid arthritis;

Virally induced hepatic cirrhosis, for example hepatitis C;

Radiation-induced fibrosis;

Restenosis, post angioplasty;

Renal disorders including chronic glomerulonephritis, renal fibrosis in patients receiving cyclosporine and renal fibrosis due to high blood pressure;

Diseases of the skin with a fibrotic component including but not limited to, scleroderma, sarcodosis, systemic lupus erythematosus;

Excessive scarring.

In a preferred embodiment in accordance with the present invention, the compounds of general formula I, their tautomers, their stereoisomers or the physiologically acceptable salts thereof are especially suitable for the prevention or treatment of idiopathic pulmonary fibrosis.

Biological Activity

The following experimental results illustrate the present invention without representing a limitation of its scope.

EXAMPLE B1

In the following experiments of Example B1, Example A denotes the compound 3-Z-[1-(4-(N-dimethylaminomethyl-carbonyl-N-methyl-amino)-anilino)-1-phenyl-methylene]-6-methoxycarbonyl-2-indolinone, which is compound (m) of the list of the preferred compounds.

(A) Effect of a Representative Compound on Lung Morphology Following Bleomycin-induced Pulmonary Fibrosis.

Materials and Methods

Bleomycin sulfate (Bleomycin HEXAL™) was purchased from a local pharmacy.

Bleomycin Administration and Treatment Protocols

All experiments were performed in accordance with German guidelines for animal welfare, performed by persons certified to work with animals and approved by the responsible authorities. Male Wistar rats were intratracheally injected with Bleomycin sulfate (10U/kg body weight in 300 µl saline) or saline alone (saline control) using a catheter (0.5 mm internal diameter, 1.0 mm external diameter) through the nasal passage, following exposure to the anaesthetic Isofluorane for 5 minutes. The following day, the rats were orally treated with Example A (compound (m)) or saline suspended in 1 ml 0.1% Natrosol. Control rats were administered 1 ml 0.1% Natrosol (vehicle control).

A total of 25 rats were investigated and were grouped and treated as shown in Table 1.

TABLE 1

| Intratracheal instillation | No. of animals | Compound | Treatment Schedule |
| --- | --- | --- | --- |
| Bleomycin 10 U/kg | 10 | Example A (Compound (m)) | Days 1-21 |
| Bleomycin 10 U/kg | 10 | Vehicle only | Days 1-21 |
| Saline (300 µl) | 5 | Vehicle only | Days 1-21 |

21 days following bleomycin instillation, the rats were killed with a lethal intraperitoneal injection of Narcoren™ (Pentobarbital Sodium, Rhone Merieux). The lungs were then removed, blotted dry and half was snap frozen in liquid nitrogen and stored at −80° C. The other half was fixed in 4% formalin for subsequent paraffin embedding and histology.

Histology

The lung tissues fixed in 4% formalin were embedded into paraffin and 5 µm sections were cut using a microtome (Leica SM200R) and placed on poly-L-lysine coated slides. The sections were then dried onto the slides (60° C. 2 hours) and then left to cool at room temperature. Collagen deposition was assessed using Masson's Trichrome staining.

Results

FIG. 1A shows the result obtained with the control group, which received saline and the vehicle instead of bleomycin intratracheally.

Figure 1B:
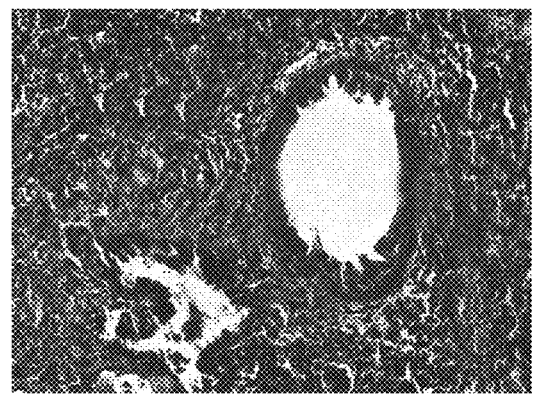
FIG. 1B depicts lung tissue removed from a rat from a group of the experiment described in Example B1(A) which was treated intratracheally with bleomycin and vehicle.

Rats treated intratracheally with bleomycin and the vehicle developed severe lung fibrosis, as seen in FIG. 1B. The alveoli have been largely replaced by fibroblasts and extracellular matrix and the normal lung structure is nearly obliterated.

Figure 1C:
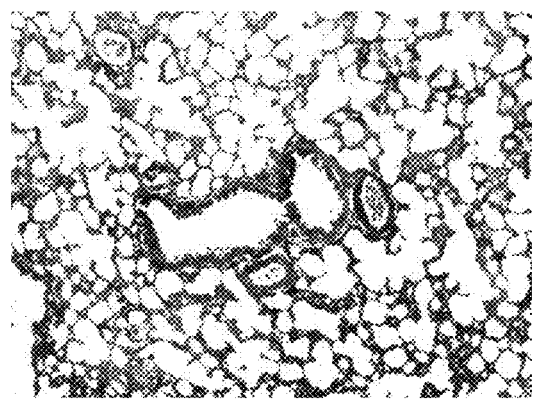
FIG. 1C depicts lung tissue removed from a rat from a group of the experiment described in Example B1(A) which were treated with bleomycin and also treated with Compound (m).

Daily treatment of bleomycin-treated rats with 50 mg/kg of Example A (compound (m)) showed a consistent, nearly complete reversal of lung fibrosis in this model. A typical example is shown in FIG. 1C. Alveoli are intact and little or no fibroblast infiltration or extracellular matrix deposition has occurred. Normal lung structure has been maintained, which is evidenced by a comparison of FIG. 1C with FIG. 1A.

(B) Effect of a Representative Compound on Expression of Fibrotic Marker Genes Following Bleomycin-induced Pulmonary Fibrosis.

mRNA Extractions and Synthesis of cDNA

One part of the frozen lung tissue dedicated to investigation of gene expression was cut into small pieces using a sterile scalpel blade. Approximately 100 mg of tissue was then placed into a 2 ml Eppendorf tube and 1.5 ml of Trizol (Invitrogen) was added. A sterile tungsten carbide bead (Qiagen) was then added to the tube and the tube was placed in a Retsch MM300 Tissue disruptor (Qiagen) at a frequency of 30.0 Hz for 8 minutes. After this time, the bead was removed and the sample centrifuged at 12000 rpm for 10 minutes to remove tissue debris. The RNA was extracted using a modified version of the manufacturer's protocol supplied with Trizol. Briefly, 0.3 ml chloroform was added to the tube and the tube shaken vigorously and then left to incubate at room temperature for 5 minutes, after which the tube was centrifuged for 15 minutes at 12000 rpm at 4° C. The upper colorless aqueous phase was then collected and added to 750 µl isopropanol. This was then shaken vigorously and stored at −80° C. overnight. The samples were then incubated at room temperature for 15 minutes, after which they were centrifuged for 40 minutes at 12000 rpm at 4° C. The supernatant was then removed and 500 µl of 70% ethanol was added to wash the pellet then the sample was centrifuged for 10 minutes at 12000 rpm an 4° C., this wash step was repeated twice, after which the pellet was left to dry for 10-15 minutes. Finally the pellet was resuspended in 20 µl RNase free water and stored at −80° C. The concentration of each sample was then measured using a spectrophotometer.

Using the Superscript™ III (Invitrogen, Paisley, UK) RT-first strand synthesis kit, 2 µg of each mRNA sample was reversed transcribed using a modified version of the manufacturer's protocol. Briefly, a mixture of 2 µg RNA, 1 µl random hexamer primers (50 ng/µl), 1 µl dNTP mix (10 mM) was made up to 10 µl with DEPC-treated water and incubated at 65° C. for 5 minutes, after which it was placed on ice for 5 minutes. Following this, to each reaction, 2 µl RT buffer (10×), 4 µl MgCl$_2$ (25 mM), 2 µl DTT (0.1M), 1 µl RNaseOUT™ (40 U/µl) and 1 µl SuperScript™ III enzyme (200 U/µl) was added and the mixture placed in a thermal cycler (Applied Biosystems) under the following conditions: 25° C. for 10 minutes, 50° C. for 50 minutes and 85° C. for 5 minutes, after which 1 µl of RNase H was added and incubated at 37° C. for 20 minutes. The synthesized cDNA was diluted to 5 ng/µl using the assumption that the RT reaction fully transcribed all of the mRNA to cDNA and was a concentration of 100 ng/µl.

Investigation of Gene Expression Using Real Time PCR

Gene expression was investigated in each of the samples using the Applied Biosystems 7700 sequence detection system. Primers for the 18S endogenous control and TGFb1 were purchased as pre-developed assay reagent kits, whereas primers and probes (see Table 2 below) for procollagen I and fibronectin were designed using PrimerExpress™ (Applied Biosystems), ensuring that at least one of the primers or probes in each set overlapped an intron/exon junction, thus eliminating the possibility of amplifying any contaminating genomic DNA in the cDNA sample. The purchased PDARs also amplified only cDNA.

TABLE 2

| Target | | Sequence |
|---|---|---|
| Fibro-<br>nectin | Forward<br>Reverse<br>Probe | 5'-GAT GCC GAT CAG AAG TTT GGA-3'<br>5'-TCG TTG GTC GTG CAG ATC TC-3'<br>5'-FAM-CTG CCC AAT GGC TGC CCA TGA-TAMRA-3' |
| Pro-<br>Colla-<br>gen I | Forward<br>Reverse<br>Probe | 5'-CAG ACT GGC AAC CTG AAG AAG TC-3'<br>5'-TCG CCC CTG AGC TCG AT-3'<br>5'-FAM-CTG CTC CTC CAG GGC TCC AAC GA-TAMRA3' |

Real Time PCR was carried out in 25 µl reactions, using 25 ng (5 µl) of cDNA per reaction. A quantitative PCR core kit was purchased (Eurogentec) and a master-mix was made up as follows for 100 reactions: 500 µl 10× reaction buffer, 500 µl MgCl$_2$ (50 mM), 200 µl dNTP mix solution (5 mM), 25 µl Hot Goldstar enzyme, 75 µl 18S PDAR, 22.5 µl forward primer, 22.5 µl reverse primer, 15 µl probe and 640 µl DEPC treated water. 20 µl of this master-mix was then added to 25 ng (5 µl) target cDNA. Each analysis was carried out in triplicate.

In order to quantify the gene expression, a standard curve was constructed for each primer set and was included on each plate. The standards were made up of a mix of all the cDNA's under investigation; this mix of cDNA's was serially diluted 10, 20, 50, 100, 100 times. A standard curve was constructed of the obtained C$_T$ (Cycle at which amplification reaches a set Threshold) against the LOG$_{10}$ of the dilution factor.

Curves were drawn for the target gene and the 18S rRNA endogenous control. The C$_T$ value for both targets for each of the samples was then converted to a fold dilution using the standard curve and the target gene value was normalized to the 18S gene value.

Statistics

All statistical analyses were carried out using GraphPad Prism V 4.02 software. Comparisons were made using a non-parametric T-test (Mann-Whitney U test) and a significant value was considered to be p. 0.05.

Results

Figure 2:
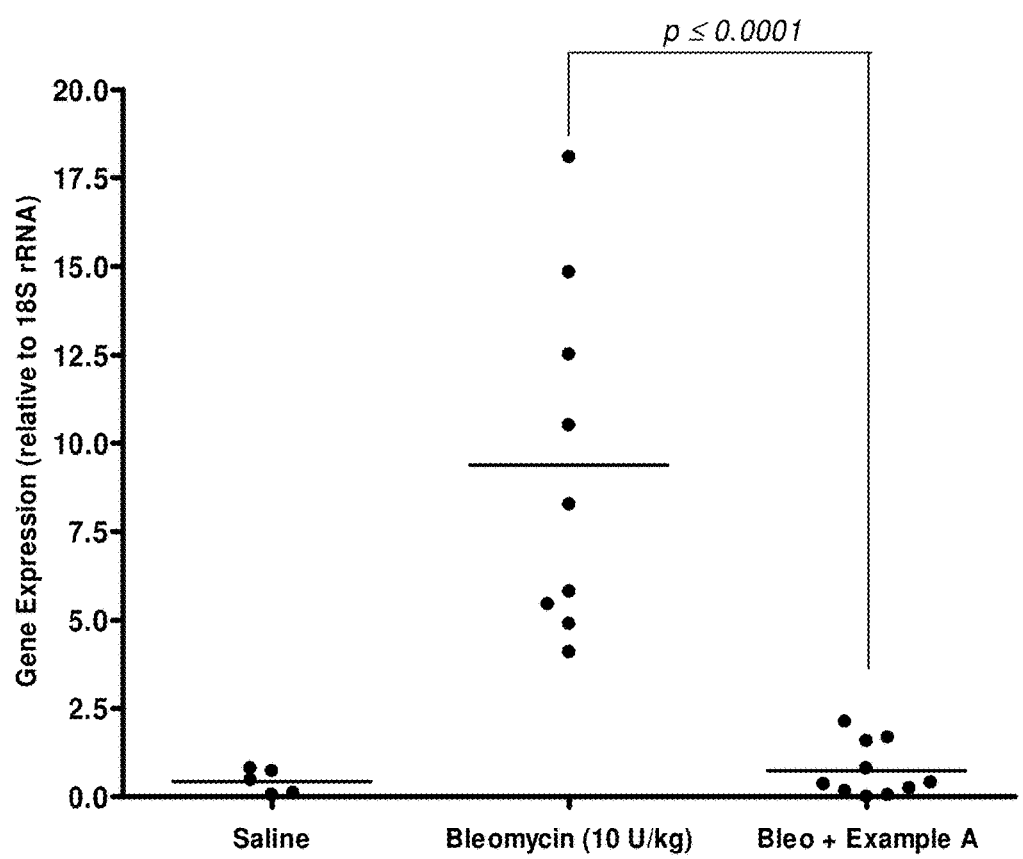
FIGS. 2 and 3 depict the results experiments described in Example B1(B) to determine the effect of Compound (m) on expression of fibrotic marker genes (procollagen I and fibronectin, respectively) following bleomycin-induced pulmonary fibrosis.

The results are shown in FIGS. 2 (procollagen I) and 3 (fibronectin). Each data point represents RNA isolated from the lung of a single rat.

Figure 3:
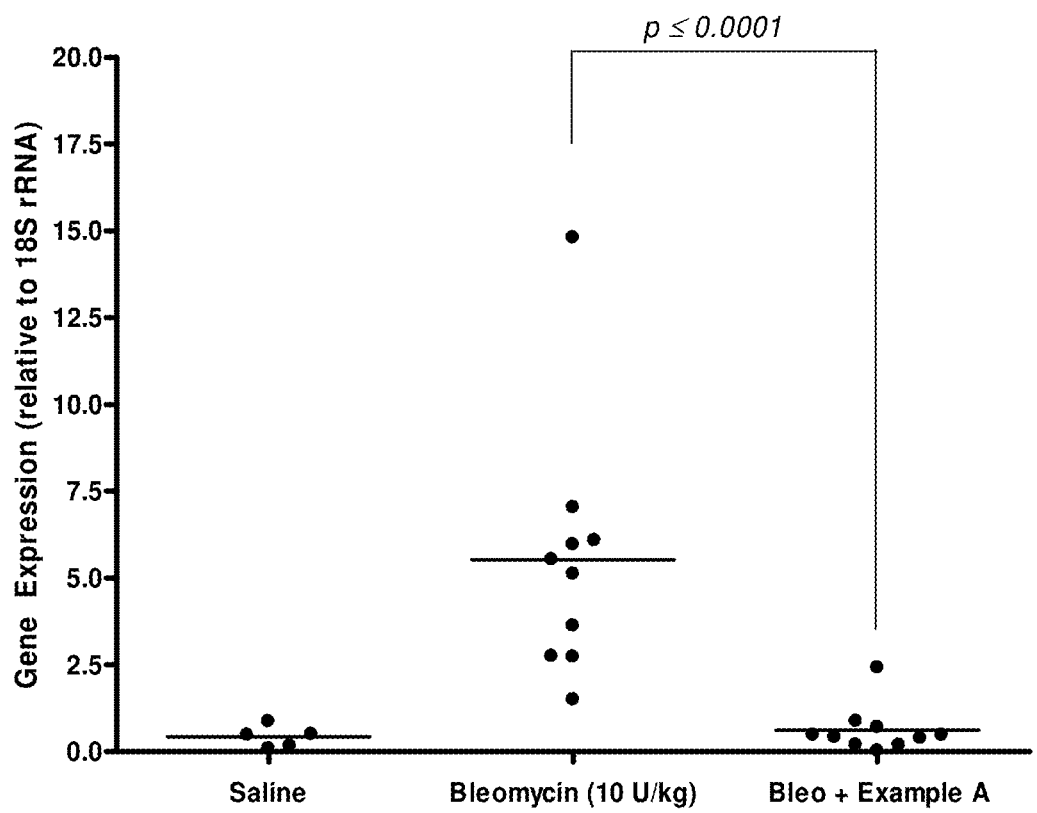

Intratracheal administration of bleomycin and subsequent treatment with vehicle only showed large increases in procollagen I and fibronectin gene expression in the lung, as seen in FIGS. 2 and 3, consistent with the histologically apparent lung fibrosis seen in FIG. 1B.

Daily treatment of Bleomycin-treated rats with 50 mg/kg of Example A (compound (m)) showed a significant (p≤0.0001) inhibition of expression of fibrotic marker genes in this model, as seen in FIGS. 2 and 3.

This experiment thus demonstrates that expression of fibrotic markers, and therefore deposition of extracellular matrix, may be dramatically reduced by treatment with Example A (compound (m)).

EXAMPLE B2

In the following experiments of Example B2, the compound 3-Z-[1-(4-(N-((4-methyl-piperazin-1-yl)-methylcarbonyl)-N-methyl-amino)-anilino)-1-phenyl-methylene]-6-methoxycarbonyl-2-indolinone, which is compound (u) of the list of the preferred compounds, was used.

All the methods employed are the same as the methods described in the experiments of Example B1, however using compound (u) instead of compound (m).

(A) Effect of a Representative Compound on Lung Morphology Following Bleomycin-Induced Pulmonary Fibrosis.

Samples were prepared from rats treated as outlined in above Table 1 of experimental Example B1 (A).

Results

Figure 4A:
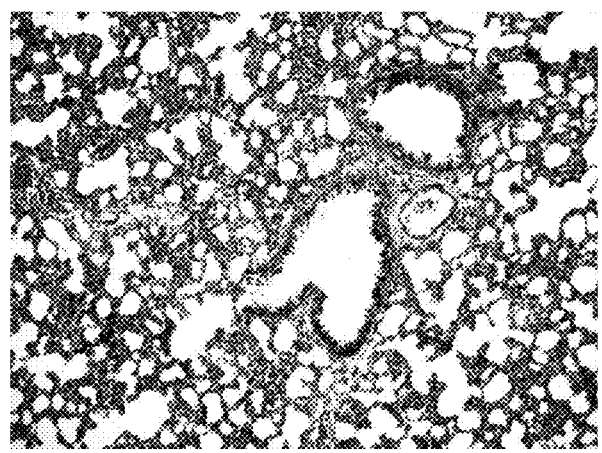
FIG. 4A depicts lung tissue removed from a rat from a control group of the experiment described in Example B2 which received saline and vehicle (0.1% Natrosol) instead of bleomycin intratracheally.

FIG. 4A shows the result obtained with the control group, which received saline and the vehicle instead of bleomycin intratracheally.

Figure 4B:
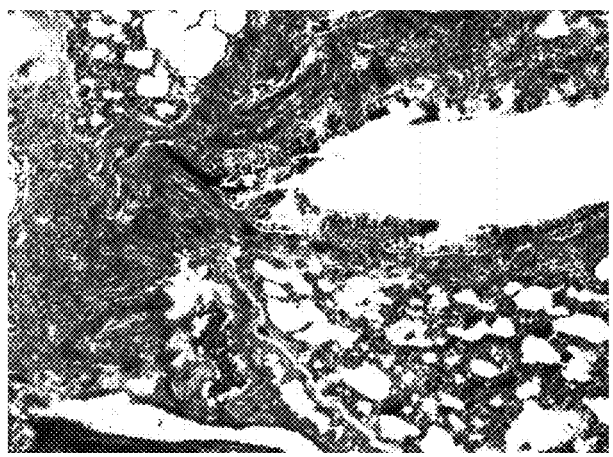
FIG. 4B depicts lung tissue removed from a rat from a group of the experiment described in Example B2 which was treated intratracheally with bleomycin and vehicle.

Rats treated intratracheally with bleomycin and the vehicle developed severe lung fibrosis, as seen in FIG. 4B. The alveoli have been largely replaced by fibroblasts and extracellular matrix and the normal lung structure is nearly obliterated.

Figure 4C:
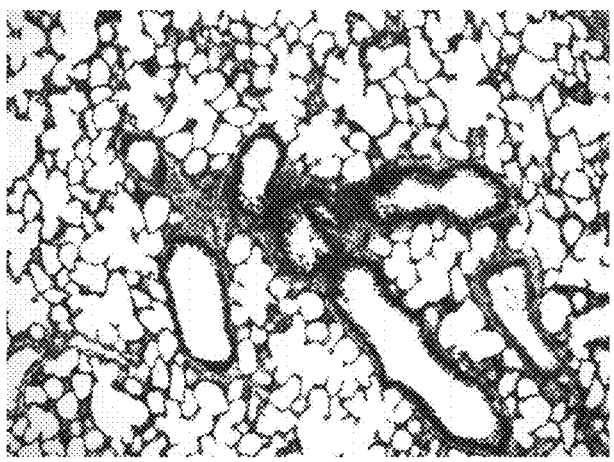
FIG. 4C depicts lung tissue removed from a rat from a group of the experiment described in Example B2 which were treated with bleomycin and also treated with Compound (u).

Daily treatment of bleomycin-treated rats with 50 mg/kg of compound (u) showed a consistent, nearly complete reversal of lung fibrosis in this model. A typical example is shown in FIG. 4C. Alveoli are intact and little or no fibroblast infiltration or extracellular matrix deposition has occurred. Normal lung structure has been maintained, which is evidenced by a comparison of FIG. 4C with FIG. 4A.

(B) Effect of a Representative Compound on Expression of Fibrotic Marker Genes Following Bleomycin-induced Pulmonary Fibrosis.

The experiment was carried out using the methods as outlined above for Example B1 (B).

Figure 5:
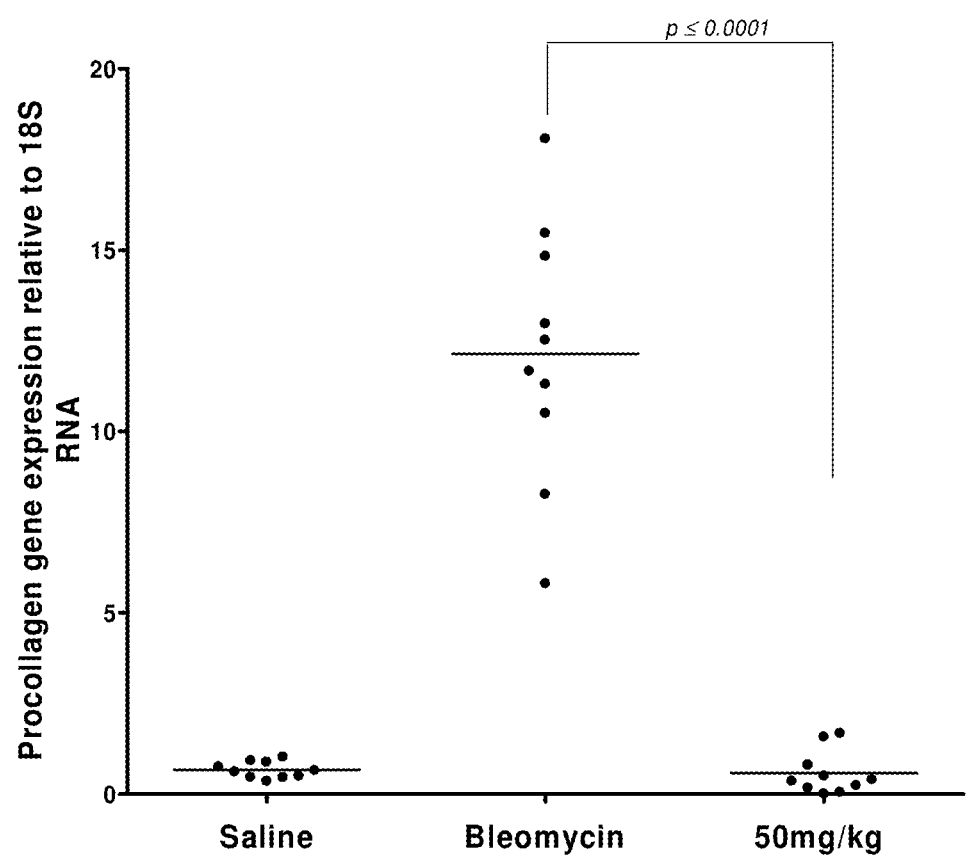
FIGS. 5 and 6 depict the results experiments described in Example B2 to determine the effect of Compound (u) on expression of fibrotic marker genes (procollagen I and fibronectin, respectively) following bleomycin-induced pulmonary fibrosis.
Figure 6:
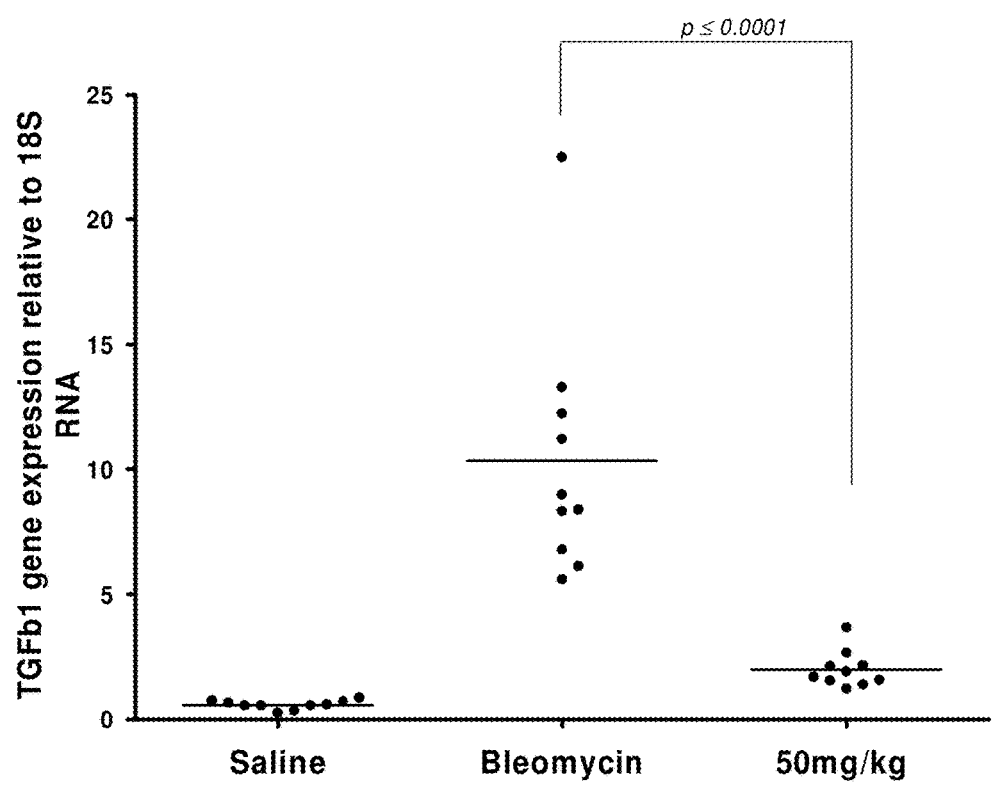

The results are shown in FIG. 5 (procollagen I) and FIG. 6 (TGFb). Each data point represents RNA isolated from the lung of a single rat.

Intratracheal administration of bleomycin and subsequent treatment with vehicle only showed large increases in procollagen I and TGFb gene expression in the lung, as seen in FIGS. 5 and 6, consistent with the histologically apparent lung fibrosis seen in FIG. 1B.

Daily treatment of bleomycin-treated rats with 50 mg/kg of (compound (u) showed a significant (p≤0.0001) inhibition of expression of fibrotic marker genes in this model, as seen in FIGS. 5 and 6.

This experiment also demonstrates that expression of fibrotic markers, and therefore deposition of extracellular matrix, may be dramatically reduced by treatment with another compound representative of this invention, namely compound (u).

By reason of their biological properties the compounds according to the invention may be used in monotherapy or in conjunction with other pharmacologically active compounds. Such pharmacologically active compounds may be compounds which are, for example, also pharmacologically active in the treatment of fibrosis. Such pharmacologically active compounds may also be substances with a secretolytic, broncholytic and/or anti-inflammatory activity.

In a preferred embodiment in accordance with the present invention, such pharmacologically active compounds are preferably selected from the group consisting of anticholinergic agents, beta-2 mimetics, steroids, PDE-IV inhibitors, p38 MAP kinase inhibitors, NK$_1$ antagonists, LTD4 antagonists, EGFR inhibitors and endothelin-antagonists.

Anticholinergic agents may preferably be selected from the group consisting of the tiotropium salts, oxitropium salts, flutropium salts, ipratropium salts, glycopyrronium salts and trospium salts.

Beta-2 mimetics may preferably be selected from the beta-2 mimetics disclosed, for example, in U.S. Pat. No. 4,460,581, which is incorporated herein by reference.

PDE-IV inhibitors may preferably be selected from the group consisting of enprofyllin, theophyllin, roflumilast, ariflo (cilomilast), CP-325,366, BY343, D-4396 (Sch-351591), AWD-12-281 (GW-842470), N-(3,5-dichloro-1-oxo-pyridin-4-yl)-4-difluoromethoxy-3-cyclopropyl-methoxybenzamide, NCS-613, pumafentine, (−)p-[(4aR*, 10bS*)-9-ethoxy-1,2,3,4,4a,10b-hexahydro-8-methoxy-2-methylbenzo[s][1,6]naphthyridin-6-yl]-N,N-diisopropylbenzamide, (R)-(+)-1-(4-bromobenzyl)-4-[(3-cyclopentyloxy)-4-methoxyphenyl]-2-pyrrolidone, 3-(cyclopentyloxy-4-methoxyphenyl)-1-(4-N'-[N-2-cyano-S-methyl-isothioureido]benzyl)-2-pyrrolidone, cis[4-cyano-4-(3-cyclopentyloxy-4-methoxyphenyl)cyclohexane-1-carbonic acid], 2-carbomethoxy-4-cyano-4-(3-cyclopropylmethoxy-4-difluoromethoxyphenyl) cyclohexan-1-one, cis[4-cyano-4-(3-cyclopropylmethoxy-4-difluoromethoxyphenyl)cyclohexan-1-ol], (R)-(+)-ethyl [4-(3-cyclopentyloxy-4-methoxyphenyl)pyrrolidin-2-yliden]acetate, (S)-(−)-ethyl[4-(3-cyclopentyloxy-4-methoxyphenyl)pyrrolidin-2-yliden]acetate, CDP840, Bay-198004, D-4418, PD-168787, T-440, T-2585, arofyllin, atizoram, V-11294A, Cl-1018, CDC-801, CDC-3052, D-22888, YM-58997, Z-15370, 9-cyclopentyl-5,6-dihydro-7-ethyl-3-(2-thienyl)-9H-pyrazolo[3,4-c]-1,2,4-triazolo[4,3-a]pyridine and 9-cyclopentyl-5,6-dihydro-7-ethyl-3-(tert-butyl)-9H-pyrazolo[3,4-c]-1,2,4-triazolo[4,3-a]pyridine. These compounds may be used, as available, in the form of their racemates, enantiomers or diastereoisomers, or in the form of pharmacologically acceptable acid addition salts thereof, or in the form of their solvates and/or hydrates.

Steroids may preferably be selected from the group consisting of prednisolone, prednisone, butixocortpropionate, RPR-106541, flunisolid, beclomethasone, triamcinolone, budesonid, fluticasone, mometasone, ciclesonid, rofleponid, ST-126, dexamethasone, 6α,9α-difluoro-17α-[(2-furanyl-carbonyl)oxy]-11β-hydroxy-16α-methyl-3-oxo-androsta-1,4-dien-17β-carbothionic acid (S)-fluoromethylester, and 6α,9α-difluoro-11-hydroxy-16α-methyl-3-oxo-17α-propionyloxy-androsta-1,4-diene-17β-carbothionic acid (S)-(2-oxo-tetrahydro-furan-3S-yl)ester. These compounds may be used, as available, in the form of their racemates, enantiomers or diastereoisomers, or in the form of pharamologically acceptable acid addition salts thereof, or in the form of their solvates and/or hydrates.

p38 MAP kinase inhibitors may preferably be selected from the group consisting of the p38 Kinase inhibitors that are disclosed for instance in U.S. Pat. Nos. 5,716,972, 5,686,455, 5,656,644, 5,593,992, 5,593,991, 5,663,334, 5,670,527, 5,559,137, 5,658,903, 5,739,143, 5,756,499, 6,277,989, 6,340,685, and 5,716,955 and PCT applications WO 92/12154, WO 94/19350, WO 95/09853, WO 95/09851, WO 95/09847, WO 95/09852, WO 97/25048, WO 97/25047, WO 97/33883, WO 97/35856, WO 97/35855, WO 97/36587, WO 97/47618, WO 97/16442, WO 97/16441, WO 97/12876, WO 98/25619, WO 98/06715, WO 98/07425, WO 98/28292, WO 98/56377, WO 98/07966, WO 98/56377, WO 98/22109, WO 98/24782, WO 98/24780, WO 98/22457, WO 98/52558, WO 98/52559, WO 98/52941, WO 98/52937, WO 98/52940, WO 98/56788, WO 98/27098, WO 98/47892, WO 98/47899, WO 98/50356, WO 98/32733, WO 99/58523, WO 99/01452, WO 99/01131, WO 99/01130, WO 99/01136, WO 99/17776, WO 99/32121, WO 99/58502, WO 99/58523, WO 99/57101, WO 99/61426, WO 99/59960, WO 99/59959, WO 99/00357, WO 99/03837, WO 99/01441, WO 99/01449, WO 99/03484, WO 99/15164, WO 99/32110, WO 99/32111, WO 99/32463, WO 99/64400, WO 99/43680, WO 99/17204, WO 99/25717, WO 99/50238, WO 99/61437, WO 99/61440, WO 00/26209, WO 00/18738, WO 00/17175, WO 00/20402, WO 00/01688, WO 00/07980, WO 00/07991, WO 00/06563, WO 00/12074, WO 00/12497, WO 00/31072, WO 00/31063, WO 00/23072, WO 00/31065, WO 00/35911, WO 00/39116, WO 00/43384, WO 00/41698, WO 00/69848, WO 00/26209, WO 00/63204, WO 00/07985, WO 00/59904, WO 00/71535, WO 00/10563, WO 00/25791, WO 00/55152, WO 00/55139, WO 00/17204, WO 00/36096, WO 00/55120, WO 00/55153, WO 00/56738, WO 01/21591, WO 01/29041, WO 01/29042, WO 01/62731, WO 01/05744, WO 01/05745, WO 01/05746, WO 01/05749, WO 01/05751, WO 01/27315, WO 01/42189, WO 01/00208, WO 01/42241, WO 01/34605, WO 01/47897, WO 01/64676, WO 01/37837, WO 01/38312, WO 01/38313, WO 01/36403, WO 01/38314, WO 01/47921, WO 01/27089, DE 19842833, and JP 2000 86657 whose disclosures are all incorporated herein by reference in their entirety. Of particular interest for the combinations according to the invention are those p38 inhibitors disclosed in U.S. Pat. Nos. 6,277,989, 6,340,685, WO 00/12074, WO 00/12497, WO 00/59904, WO 00/71535, WO 01/64676, WO 99/61426, WO 00/10563, WO 00/25791, WO 01/37837, WO 01/38312, WO 01/38313, WO 01/38314, WO 01/47921, WO 99/61437, WO 99/61440, WO 00/17175, WO 00/17204, WO 00/36096, WO 98/27098, WO 99/00357, WO 99/58502, WO 99/64400, WO 99/01131, WO 00/43384, WO 00/55152, WO 00/55139, and WO 01/36403. In a preferred embodiment the p38 kinase inhibitor is selected from the compounds of following formula (I) as disclosed in WO 99/01131

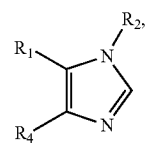

(I)

wherein $R_1$ is 4-pyridyl, pyrimidinyl, 4-pyridazinyl, 1,2,4-triazin-5-yl, quinolyl, isoquinolinyl, or quinazolin-4-yl ring, which ring is substituted with Y—$R_a$ and optionally with an additional independent substituent selected from $C_{1-4}$ alkyl, halogen, hydroxyl, $C_{1-4}$ alkoxy, $C_{1-4}$ alkylthio, $C_{1-4}$ alkylsulfinyl, $CH_2OR_{12}$, amino, mono and di-$C_{1-6}$ alkyl substituted amino, an N-heterocyclyl ring which ring has from 5 to 7 members and optionally contains an additional heteroatom selected from oxygen, sulfur or $NR_{15}$, $N(R_{10})$ $C(O)R_b$ or $NHR_a$;

Y is oxygen or sulfur;

$R_4$ is phenyl, naphth-1-yl or naphthyl, or a heteroaryl, which is optionally substituted by one or two substituents, each of which is independently selected, and which, for a 4-phenyl, 4naphth-1-yl, 5-naphth-2-yl or 6-naphth-2-yl substituent, is halogen, cyano, nitro, $C(Z)NR_7R_{17}$, $C(Z)$ $OR_{16}$, $(CR_{10}R_{20})_vCOR_{12}$, $SR_5$, $SOR_5$, $OR_{12}$, halo-substituted-$C_{1-4}$ alkyl, $C_{1-4}$ alkyl, $ZC(Z)R_{12}$, $NR_{10}C(Z)R_{16}$, or $(CR_{10}R_{20})_vNR_{10}R_{20}$ and which, for other positions of substitution, is halogen, cyano, $C(Z)NR_{13}R_{14}$, $C(Z)OR_3$, $(CR_{10}R_{20})_{m''}COR_3$, $S(O)_mR_3$, $OR_3$, halo-substituted-$C_{1-4}$ alkyl, $C_{1-4}$ alkyl, $(CR_{10}R_{20})_{m''}R_{10}C(Z)R_3$, $NR_{10}S(O)_mR_8$, $NR_{10}S(O)_{m}NR_7R_{17}$, $ZC(Z)R_3$ or $(CR_{10}R_{20})_{m''}NR_{13}R_{14}$;

Z is oxygen or sulfur;
n is an integer having a value of 1 to 10;
m is 0, or integer 1 or 2;
m' is an integer having a value of 1 or 2;
m" is 0, or an integer having a value of 1 to 5;
v is 0, or an integer having a value of 1 to 2;
$R_2$ is —C(H)(A)($R_{22}$)
A is optionally substituted aryl, heterocyclyl, or heteroaryl ring, or A is substituted $C_{1-10}$ alkyl;
$R_{22}$ is an optionally substituted $C_{1-10}$ alkyl;
$R_a$ is aryl, aryl$C_{1-6}$ alkyl, heterocyclic, heterocyclyl$C_{1-6}$ alkyl, heteroaryl, heteroaryl$C_{1-6}$alkyl, wherein each of these moieties may be optionally substituted;
$R_b$ is hydrogen, $C_{1-6}$ alkyl, $C_{3-7}$ cycloalkyl, aryl, aryl $C_{1-4}$ alkyl, heteroaryl, heteroaryl$C_{1-4}$alkyl, heterocyclyl, or heterocyclyl$C_{1-4}$ alkyl, wherein each of these moieties may be optionally substituted;
$R_3$ is heterocyclyl, heterocyclyl $C_{1-10}$ alkyl or $R_8$;
$R_5$ is hydrogen, $C_{1-4}$ alkyl, $C_{2-4}$ alkenyl, $C_{2-4}$ alkynyl or $NR_7R_{17}$, excluding the moieties $SR_5$ being $SNR_7R_{17}$ and $SOR_5$ being SOH;
$R_6$ is hydrogen, a pharmaceutically acceptable cation, $C_{1-10}$ alkyl, $C_{3-7}$ cycloalkyl, aryl, aryl $C_{1-4}$ alkyl, heteroaryl, heteroaryl $C_{1-4}$ alkyl, heterocyclyl, aryl, or $C_{1-10}$ alkanoyl;
$R_7$ and $R_{17}$ is each independently selected from hydrogen or $C_{1-4}$ alkyl or $R_7$ and $R_{17}$ together with the nitrogen to which they are attached form a heterocyclic ring of 5 to 7 members which ring optionally contains an additional heteroatom selected from oxygen, sulfur or $NR_{15}$;
$R_8$ is $C_{1-10}$ alkyl, halo-substituted $C_{1-10}$ alkyl, $C_{2-10}$ alkenyl, $C_{2-10}$ alkynyl, $C_{3-7}$ cycloalkyl, $C_{3-7}$ cycloalkenyl, aryl, aryl $C_{1-10}$ alkyl, heteroaryl, heteroaryl $C_{1-10}$ alkyl, $(CR_{10}R_{20})_nOR_{11}$, $(CR_{10}R_{20})_nS(O)_mR_{18}$, $(CR_{10}R_{20})_nNHS(O)_2R_{18}$, $(CR_{10}R_{20})_nNR_{13}R_{14}$; wherein the aryl, arylalkyl, heteroaryl, heteroaryl alkyl may be optionally substituted;
$R_9$ is hydrogen, C(Z) $R_{11}$ or optionally substituted $C_{1-10}$ alkyl, $S(O)_2R_5$, optionally substituted aryl or optionally substituted aryl $C_{1-4}$ alkyl;
$R_{10}$ and $R_{20}$ is each independently selected from hydrogen or $C_{1-4}$ alkyl;
$R_{11}$ is hydrogen, $C_{1-10}$ alkyl, $C_{3-7}$ cycloalkyl, heterocyclyl, heterocyclyl $C_{1-10}$ alkyl, aryl, aryl$C_{1-10}$ alkyl, heteroaryl or heteroaryl $C_{1-10}$ alkyl, wherein these moieties may be optionally substituted;
$R_{12}$ is hydrogen or $R_{16}$;
$R_{13}$ an $R_{14}$ is each independently selected from hydrogen or optionally substituted $C_{1-4}$ alkyl, optionally substituted aryl or optionally substituted aryl$C_{1-4}$ alkyl, or together with the nitrogen which they are attached form a heterocyclic ring of 5 to 7 members which ring optionally contains an additional heteroatom selected from oxygen, sulfur or $NR_9$;
$R_{15}$ is $R_{10}$ or C(Z)—$C_{1-4}$ alkyl;
$R_{16}$ is $C_{1-4}$ alkyl, halo-substituted-$C_{1-4}$ alkyl, or $C_{3-7}$ cycloalkyl;
$R_{18}$ is $C_{1-10}$ alkyl, $C_{3-7}$ cycloalkyl, heterocyclyl, aryl, aryl$_{1-10}$ alkyl, heterocyclyl, heterocyclyl-$C_{1-10}$ alkyl, heteroaryl or heteroaryl$_{1-10}$ alkyl;
or a pharmaceutically acceptable salt thereof.

NK$_1$ antagonists may preferably be selected from the group consisting of N-[2-(3,5-bis-trifluoromethyl-phenyl)-ethyl]-2-{4-cyclopropylmethyl-piperazin-1-yl}-N-methyl-2-phenyl-acetamide (BIIF 1149), CP-122721, FK-888, NKP 608C, NKP 608A, CGP 60829, SR 48968 (Saredutant), SR 140333 (Nolpitantium besilate/chloride), LY 303 870 (Lanepitant), MEN-11420 (Nepadutant), SB 223412, MDL-105172A, MDL-103896, MEN-11149, MEN-11467, DNK 333A, SR-144190, YM-49244, YM-44778, ZM-274773, MEN-10930, S-19752, Neuronorm, YM-35375, DA-5018, Aprepitant (MK-869), L-754030, CJ-11974, L-758298, DNK-33A, 6b-I, CJ-11974, TAK-637, GR 205171 and the arylglycine amide derivates of general formula (VIII)

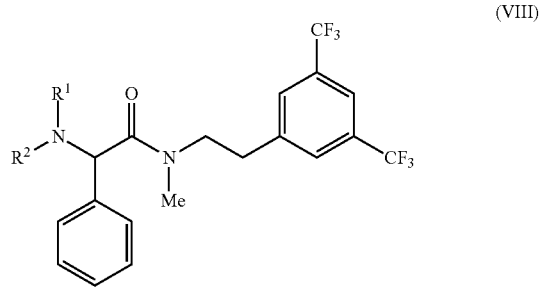

(VIII)

wherein
$R^1$ and $R^2$ together with the N-atom they are bound to form a ring of formula

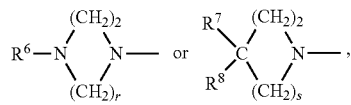

wherein r and s independently denote the number 2 or 3;
$R^6$ denotes H, —$C_1$-$C_5$-alkyl, $C_3$-$C_5$-alkenyl, propinyl, hydroxy($C_2$-$C_4$)alkyl, methoxy($C_2$-$C_4$)alkyl, di($C_1$-$C_3$) alkylamino($C_2$-$C_4$)alkyl, amino($C_2$-$C_4$)alkyl, amino, di($C_1$-$C_3$)alkylamino, monofluoro- up to perfluoro($C_1$-$C_2$)alkyl, N-methylpiperidinyl, pyridyl, pyrimidinyl, pyrazinyl or pyridazinyl,
$R^7$ denotes any of the groups defined under (a) to (d):
(a) hydroxy
(b) 4-piperidinopiperidyl,
(c)

wherein $R^{16}$ and $R^{17}$ independently denote H, ($C_1$-$C_4$) alkyl, ($C_3$-$C_6$)cycloalkyl, hydroxy($C_2$-$C_4$)alkyl, dihydroxy($C_2$-$C_4$)alkyl, ($C_1$-$C_3$)alkoxy($C_2$-$C_4$)alkyl, phenyl($C_1$-$C_4$)alkyl or di($C_1$-$C_3$)alkylamino($C_2$-$C_4$)alkyl, and
$R^8$ denotes H,
optionally in the form of enantiomers, mixtures of enantiomers or the racemates.

The compounds of formula (VIII) mentioned hereinbefore are described in WO 96/32386, WO 97/32865 and WO 02/32865. The disclosure of these international patent applications is incorporated herein by reference in its entirety.

LTD4 antagonists may preferably be selected from the group consisting of montelukast, 1-(((R)-(3-(2-(6,7-difluoro-2-quinolinyl)ethenyl)phenyl)-3-(2-(2-hydroxy-2-propyl)phenyl)thio)methylcyclopropane-acetate, 1-(((1R)-3(3-(2-(2,3-dichlorothieno[3,2-b]pyridin-5-yl)-(E)-ethenyl) phenyl)-3-(2-(1-hydroxy-1-methylethyl)phenyl)propyl)

thio)methyl)cyclopropane-acetate, pranlukast, zafirlukast, [2-[[2-(4-tert-butyl-2-thiazolyl)-5-benzofuranyl]oxymethyl]phenyl]acetate, MCC-847 (ZD-3523), MN-001, MEN-91507 (LM-1507), VUF-5078, VUF-K-8707 and L-733321. These compounds may be used, as available, in the form of their racemates, enantiomers or diastereoisomers, or in the form of pharamacologically acceptable acid addition salts thereof, or in the form of their solvates and/or hydrates.

EGFR inhibitors may preferably be selected from the group consisting of 4-[(3-chlor-4-fluorphenyl)amino]-6-{[4-(morpholin-4-yl)-1-oxo-2-buten-1-yl]amino}-7-cyclopropylmethoxy-chinazoline, 4-[(3-chlor-4-fluorphenyl)amino]-6-{[4-(N,N-diethylamino)-1-oxo-2-buten-1-yl]amino}-7-cyclopropylmethoxy-chinazoline, 4-[(3-chlor-4-fluorphenyl)amino]-6-{[4-(N,N-dimethylamino)-1-oxo-2-buten-1-yl]amino}-7-cyclopropylmethoxy-chinazoline, 4-[(R)-(1-phenyl-ethyl)amino]-6-{[4-(morpholin-4-yl)-1-oxo-2-buten-1-yl]amino}-7-cyclopentyloxy-chinazoline, 4-[(3-chlor-4-fluor-phenyl)amino]-6-{[4-((R)-6-methyl-2-oxo-morpholin-4-yl)-1-oxo-2-buten-1-yl]amino}-7-cyclopropylmethoxy-chinazoline, 4-[(3-chlor-4-fluor-phenyl)amino]-6-{[4-((R)-6-methyl-2-oxo-morpholin-4-yl)-1-oxo-2-buten-1-yl]amino}-7-[(S)-(tetrahydrofuran-3-yl)oxy]-chinazoline, 4-[(3-chlor-4-fluor-phenyl)amino]-6-{[4-((R)-2-methoxymethyl-6-oxo-morpholin-4-yl)-1-oxo-2-buten-1-yl]amino}-7-cyclopropylmethoxy-chinazoline, 4-[(3-chlor-4-fluor-phenyl)amino]-6-[2-((S)-6-methyl-2-oxo-morpholin-4-yl)-ethoxy]-7-methoxy-chinazoline, 4-[(3-chlor-4-fluorphenyl)amino]-6-({4-[N-(2-methoxy-ethyl)-N-methyl-amino]-1-oxo-2-buten-1-yl}amino)-7-cyclopropylmethoxy-chinazoline, 4-[(3-chlor-4-fluorphenyl)amino]-6-{[4-(N,N-dimethylamino)-1-oxo-2-buten-1-yl]amino}-7-cyclopentyloxy-chinazoline, 4-[(R)-(1-phenyl-ethyl)amino]-6-{[4-(N,N-bis-(2-methoxy-ethyl)-amino)-1-oxo-2-buten-1-yl]amino}-7-cyclopropylmethoxy-chinazoline, 4-[(R)-(1-phenyl-ethyl)amino]-6-({4-[N-(2-methoxy-ethyl)-N-ethyl-amino]-1-oxo-2-buten-1-yl}amino)-7-cyclopropylmethoxy-chinazoline, 4-[(R)-(1-phenyl-ethyl)amino]-6-({4-[N-(2-methoxy-ethyl)-N-methyl-amino]-1-oxo-2-buten-1-yl}amino)-7-cyclopropylmethoxy-chinazoline, 4-[(R)-(1-phenyl-ethyl)amino]-6-({4-[N-(tetrahydropyran-4-yl)-N-methyl-amino]-1-oxo-2-buten-1-yl}amino)-7-cyclopropylmethoxy-chinazoline, 4-[(3-chlor-4-fluorphenyl)amino]-6-{[4-(N,N-dimethylamino)-1-oxo-2-buten-1-yl]amino}-7-((R)-tetrahydrofuran-3-yloxy)-chinazoline, 4-[(3-chlor-4-fluorphenyl)amino]-6-{[4-(N,N-dimethylamino)-1-oxo-2-buten-1-yl]amino}-7-((S)-tetrahydrofuran-3-yloxy)-chinazoline, 4-[(3-chlor-4-fluorphenyl)amino]-6-({4-[N-(2-methoxy-ethyl)-N-methyl-amino]-1-oxo-2-buten-1-yl}amino)-7-cyclopentyloxy-chinazoline, 4-[(3-chlor-4-fluorphenyl)amino]-6-{[4-(N-cyclopropyl-N-methyl-amino)-1-oxo-2-buten-1-yl]amino}-7-cyclopentyloxy-chinazoline, 4-[(3-chlor-4-fluorphenyl)amino]-6-{[4-(N,N-dimethylamino)-1-oxo-2-buten-1-yl]amino}-7-[(R)-(tetrahydrofuran-2-yl)methoxy]-chinazoline, 4-[(3-chlor-4-fluorphenyl)amino]-6-{[4-(N,N-dimethylamino)-1-oxo-2-buten-1-yl]amino}-7-[(S)-(tetrahydrofuran-2-yl)methoxy]-chinazoline, 4-[(3-ethinyl-phenyl)amino]-6,7-bis-(2-methoxy-ethoxy)-chinazoline, 4-[(3-chlor-4-fluorphenyl)amino]-7-[3-(morpholin-4-yl)-propyloxy]-6-[(vinylcarbonyl)amino]-chinazoline, 4-[(R)-(1-phenyl-ethyl)amino]-6-(4-hydroxy-phenyl)-7H-pyrrolo[2,3-d]pyrimidine, 3-cyano-4-[(3-chlor-4-fluorphenyl)amino]-{[4-(N,N-dimethylamino)-1-oxo-2-buten-1-yl]amino}-7-ethoxy-chinoline, 4-{[3-chlor-4-(3-fluor-benzyloxy)-phenyl]amino}-6-(5-{[(2-methansulfonyl-ethyl)amino] methyl}-furan-2-yl)chinazoline, 4-[(R)-(1-phenyl-ethyl)amino]-6-{[4-((R)-6-methyl-2-oxo-morpholin-4-yl)-1-oxo-2-buten-1-yl]amino}-7-methoxy-chinazoline, 4-[(3-chlor-4-fluorphenyl)amino]-6-{[4-(morpholin-4-yl)-1-oxo-2-buten-1-yl]amino}-7-[(tetrahydrofuran-2-yl)methoxy]-chinazoline, 4-[(3-chlor-4-fluorphenyl)amino]-6-({4-[N,N-bis-(2-methoxy-ethyl)-amino]-1-oxo-2-buten-1-yl}amino)-7-[(tetrahydrofuran-2-yl)methoxy]-chinazoline, 4-[(3-ethinyl-phenyl)amino]-6-{[4-(5,5-dimethyl-2-oxo-morpholin-4-yl)-1-oxo-2-buten-1-yl]amino}-chinazoline, 4-[(3-chlor-4-fluor-phenyl)amino]-6-[2-(2,2-dimethyl-6-oxo-morpholin-4-yl)-ethoxy]-7-methoxy-chinazoline, 4-[(3-chlor-4-fluor-phenyl)amino]-6-[2-(2,2-dimethyl-6-oxo-morpholin-4-yl)-ethoxy]-7-[(R)-(tetrahydrofuran-2-yl) methoxy]-chinazoline, 4-[(3-chlor-4-fluor-phenyl)amino]-7-[2-(2,2-dimethyl-6-oxo-morpholin-4-yl)-ethoxy]-6-[(S)-(tetrahydrofuran-2-yl)methoxy]-chinazoline, 4-[(3-chlor-4-fluor-phenyl)amino]-6-{2-[4-(2-oxo-morpholin-4-yl)-piperidin-1-yl]-ethoxy}-7-methoxy-chinazoline, 4-[(3-chlor-4-fluor-phenyl)amino]-6-[1-(tert.-butyloxycarbonyl)-piperidin-4-yloxy]-7-methoxy-chinazoline, 4-[(3-chlor-4-fluor-phenyl)amino]-6-(trans-4-amino-cyclohexan-1-yloxy)-7-methoxy-chinazoline, 4-[(3-chlor-4-fluor-phenyl)amino]-6-(trans-4-methansulfonylamino-cyclohexan-1-yloxy)-7-methoxy-chinazoline, 4-[(3-chlor-4-fluor-phenyl)amino]-6-(tetrahydropyran-3-yloxy)-7-methoxy-chinazoline, 4-[(3-chlor-4-fluor-phenyl)amino]-6-(1-methyl-piperidin-4-yloxy)-7-methoxy-chinazoline, 4-[(3-chlor-4-fluor-phenyl)amino]-6-{1-[(morpholin-4-yl)carbonyl]-piperidin-4-yloxy}-7-methoxy-chinazoline, 4-[(3-chlor-4-fluor-phenyl)amino]-6-{1-[(methoxymethyl)carbonyl]-piperidin-4-yloxy}-7-methoxy-chinazoline, 4-[(3-chlor-4-fluor-phenyl)amino]-6-(piperidin-3-yloxy)-7-methoxy-chinazoline, 4-[(3-chlor-4-fluor-phenyl)amino]-6-[1-(2-acetylamino-ethyl)-piperidin-4-yloxy]-7-methoxy-chinazoline, 4-[(3-chlor-4-fluor-phenyl)amino]-6-(tetrahydropyran-4-yloxy)-7-ethoxy-chinazoline, 4-[(3-chlor-4-fluor-phenyl)amino]-6-((S)-tetrahydrofuran-3-yloxy)-7-hydroxy-chinazoline, 4-[(3-chlor-4-fluor-phenyl)amino]-6-(tetrahydropyran-4-yloxy)-7-(2-methoxy-ethoxy)-chinazoline, 4-[(3-chlor-4-fluor-phenyl)amino]-6-{trans-4-[(dimethylamino)sulfonylamino]-cyclohexan-1-yloxy}-7-methoxy-chinazoline, 4-[(3-chlor-4-fluor-phenyl)amino]-6-{trans-4-[(morpholin-4-yl)carbonylamino]-cyclohexan-1-yloxy}-7-methoxy-chinazoline, 4-[(3-chlor-4-fluor-phenyl)amino]-6-{trans-4-[(morpholin-4-yl)sulfonylamino]-cyclohexan-1-yloxy}-7-methoxy-chinazoline, 4-[(3-chlor-4-fluor-phenyl)amino]-6-(tetrahydropyran-4-yloxy)-7-(2-acetylamino-ethoxy)-chinazoline, 4-[(3-chlor-4-fluor-phenyl)amino]-6-(tetrahydropyran-4-yloxy)-7-(2-methansulfonylamino-ethoxy)-chinazoline, 4-[(3-chlor-4-fluor-phenyl)amino]-6-{1-[(piperidin-1-yl)carbonyl]-piperidin-4-yloxy}-7-methoxy-chinazoline, 4-[(3-chlor-4-fluor-phenyl)amino]-6-(1-aminocarbonylmethyl-piperidin-4-yloxy)-7-methoxy-chinazoline, 4-[(3-chlor-4-fluor-phenyl)amino]-6-(cis-4-{N-[(tetrahydropyran-4-yl)carbonyl]-N-methyl-amino}-cyclohexan-1-yloxy)-7-methoxy-chinazoline, 4-[(3-chlor-4-fluor-phenyl)amino]-6-(cis-4-{N-[(morpholin-4-yl)carbonyl]-N-methyl-amino}-cyclohexan-1-yloxy)-7-methoxy-chinazoline, 4-[(3-chlor-4-fluor-phenyl)amino]-6-(cis-4-{N-[(morpholin-4-yl)sulfonyl]-N-methyl-amino}-cyclohexan-1-yloxy)-7-methoxy-chinazoline, 4-[(3-chlor-4-fluor-phenyl)amino]-6-(trans-4-ethansulfonylamino-cyclohexan-1-yloxy)-7-methoxy-chinazoline, 4-[(3-chlor-4-fluor-phenyl)amino]-6-(1-methansulfonyl-piperidin-4-yloxy)-7-ethoxy-chinazoline, 4-[(3-chlor-4-fluor-phenyl)

amino]-6-(1-methansulfonyl-piperidin-4-yloxy)-7-(2-methoxy-ethoxy)-chinazoline, 4-[(3-chlor-4-fluor-phenyl)amino]-6-[1-(2-methoxy-acetyl)-piperidin-4-yloxy]-7-(2-methoxy-ethoxy)-chinazoline, 4-[(3-chlor-4-fluor-phenyl)amino]-6-(cis-4-acetylamino-cyclohexan-1-yloxy)-7-methoxy-chinazoline, 4-[(3-Ethinyl-phenyl)amino]-6-[1-(tert.-butyloxycarbonyl)-piperidin-4-yloxy]-7-methoxy-chinazoline, 4-[(3-Ethinyl-phenyl)amino]-6-(tetrahydropyran-4-yloxy]-7-methoxy-chinazoline, 4-[(3-chlor-4-fluor-phenyl)amino]-6-(cis-4-{N-[(piperidin-1-yl)carbonyl]-N-methyl-amino}-cyclohexan-1-yloxy)-7-methoxy-chinazoline, 4-[(3-chlor-4-fluor-phenyl)amino]-6-(cis-4-{N-[(4-methyl-piperazin-1-yl)carbonyl]-N-methyl-amino}-cyclohexan-1-yloxy)-7-methoxy-chinazoline, 4-[(3-chlor-4-fluor-phenyl)amino]-6-{cis-4-[(morpholin-4-yl)carbonylamino]-cyclohexan-1-yloxy}-7-methoxy-chinazoline, 4-[(3-chlor-4-fluor-phenyl)amino]-6-{1-[2-(2-oxopyrrolidin-1-yl)ethyl]-piperidin-4-yloxy}-7-methoxy-chinazoline, 4-[(3-chlor-4-fluor-phenyl)amino]-6-{1-[(morpholin-4-yl)carbonyl]-piperidin-4-yloxy}-7-(2-methoxy-ethoxy)-chinazoline, 4-[(3-Ethinyl-phenyl)amino]-6-(1-acetyl-piperidin-4-yloxy)-7-methoxy-chinazoline, 4-[(3-Ethinyl-phenyl)amino]-6-(1-methyl-piperidin-4-yloxy)-7-methoxy-chinazoline, 4-[(3-Ethinyl-phenyl)amino]-6-(1-methansulfonyl-piperidin-4-yloxy)-7-methoxy-chinazoline, 4-[(3-chlor-4-fluor-phenyl)amino]-6-(1-methyl-piperidin-4-yloxy)-7(2-methoxy-ethoxy)-chinazoline, 4-[(3-chlor-4-fluor-phenyl)amino]-6-(1-isopropyloxycarbonyl-piperidin-4-yloxy)-7-methoxy-chinazoline, 4-[(3-chlor-4-fluor-phenyl)amino]-6-(cis-4-methylamino-cyclohexan-1-yloxy)-7-methoxy-chinazoline, 4-[(3-chlor-4-fluor-phenyl)amino]-6-{cis-4-[N-(2-methoxy-acetyl)-N-methyl-amino]-cyclohexan-1-yloxy}-7-methoxy-chinazoline, 4-[(3-Ethinyl-phenyl)amino]-6-(piperidin-4-yloxy)-7-methoxy-chinazoline, 4-[(3-Ethinyl-phenyl)amino]-6-[1-(2-methoxy-acetyl)-piperidin-4-yloxy]-7-methoxy-chinazoline, 4-[(3-Ethinyl-phenyl)amino]-6-{1-[(morpholin-4-yl)carbonyl]-piperidin-4-yloxy}-7-methoxy-chinazoline, 4-[(3-chlor-4-fluor-phenyl)amino]-6-{1-[(cis-2,6-dimethyl-morpholin-4-yl)carbonyl]-piperidin-4-yloxy}-7-methoxy-chinazoline, 4-[(3-chlor-4-fluor-phenyl)amino]-6-{1-[(2-methyl-morpholin-4-yl)carbonyl]-piperidin-4-yloxy}-7-methoxy-chinazoline, 4-[(3-chlor-4-fluor-phenyl)amino]-6-{1-[(S,S)-(2-oxa-5-aza-bicyclo[2.2.1]hept-5-yl)carbonyl]-piperidin-4-yloxy}-7-methoxy-chinazoline, 4-[(3-chlor-4-fluor-phenyl)amino]-6-{1-[(N-methyl-N-2-methoxyethyl-amino)carbonyl]-piperidin-4-yloxy}-7-methoxy-chinazoline, 4-[(3-chlor-4-fluor-phenyl)amino]-6-(1-ethyl-piperidin-4-yloxy)-7-methoxy-chinazoline, 4-[(3-chlor-4-fluor-phenyl)amino]-6-{1-[(2-methoxyethyl)carbonyl]-piperidin-4-yloxy}-7-methoxy-chinazoline, 4-[(3-chlor-4-fluor-phenyl)amino]-6-{1-[(3-methoxypropyl-amino)-carbonyl]-piperidin-4-yloxy}-7-methoxy-chinazoline, 4-[(3-chlor-4-fluor-phenyl)amino]-6-[cis-4-(N-methansulfonyl-N-methyl-amino)-cyclohexan-1-yloxy]-7-methoxy-chinazoline, 4-[(3-chlor-4-fluor-phenyl)amino]-6-[cis-4-(N-acetyl-N-methyl-amino)-cyclohexan-1-yloxy]-7-methoxy-chinazoline, 4-[(3-chlor-4-fluor-phenyl)amino]-6-(trans-4-methylamino-cyclohexan-1-yloxy)-7-methoxy-chinazoline, 4-[(3-chlor-4-fluor-phenyl)amino]-6-[trans-4-(N-methansulfonyl-N-methyl-amino)-cyclohexan-1-yloxy]-7-methoxy-chinazoline, 4-[(3-chlor-4-fluor-phenyl)amino]-6-(trans-4-dimethylamino-cyclohexan-1-yloxy)-7-methoxy-chinazoline, 4-[(3-chlor-4-fluor-phenyl)amino]-6-(trans-4-{N-[(morpholin-4-yl)carbonyl]-N-methyl-amino}-cyclohexan-1-yloxy)-7-methoxy-chinazoline, 4-[(3-chlor-4-fluor-phenyl)amino]-6-[2-(2,2-dimethyl-6-oxo-morpholin-4-yl)-ethoxy]-7-[(S)-(tetrahydrofuran-2-yl)methoxy]-chinazoline, 4-[(3-chlor-4-fluor-phenyl)amino]-6-(1-methansulfonyl-piperidin-4-yloxy)-7-methoxy-chinazoline, 4-[(3-chlor-4-fluor-phenyl)amino]-6-(1-cyano-piperidin-4-yloxy)-7-methoxy-chinazoline, Cetuximab, Trastuzumab, ABX-EGF and Mab ICR-62. These compounds may be used, as available, in the form of their racemates, enantiomers or diastereoisomers, or in the form of pharmacologically acceptable acid addition salts thereof, or in the form of their solvates and/or hydrates. These compounds are disclosed in the prior art, e.g. in WO 96/30347, WO 97/02266, WO 99/35146, WO 00/31048, WO 00/78735, WO 01/34574, WO 01/61816, WO 01/77104, WO02/18351, WO 02/18372, WO 02/18373, WO 02/18376, WO 02/50043, WO 03/082290, Cancer Research 2004, 64:11 (3958-3965), Am J Health-Syst Pharm 2000, 57(15), 2063-2076, Clinical Therapeutics 1999, 21(2), 309-318, WO 98/50433, and WO 95/20045.

Endothelin-antagonists may preferably be selected from the group consisting of tezosentan, bosentan, enrasentan, sixtasentan, T-0201, BMS-193884, K-8794, PD-156123, PD-156707, PD-160874, PD-180988, S-0139 and ZD-1611. Any reference to endothelin-antagonists within the scope of the present invention includes a reference to the salts, preferably pharmacologically acceptable acid addition salts, or derivatives which may be formed from the endothelin-antagonists.

These combinations may be administered either simultaneously or sequentially.

For pharmaceutical use the compounds according to the invention are preferably used for warm-blooded vertebrates, particularly humans, in doses of 0.0001-100 mg/kg of body weight.

These compounds may be administered either on their own or in conjunction with other active substances by intravenous, subcutaneous, intramuscular, intraperitoneal or intranasal route, by inhalation, or transdermally, or orally, whilst aerosol formulations are particularly suitable for inhalation.

For administration they are formulated with one or more conventional inert solid, semisolid or liquid carriers e.g. with starch, different types of cellulose, lactose, mannitol, sorbitol, glucose, calcium phosphate, hard fat, fatty alcohols, glycerol, medium chained triglycerides and related esters, polyethylene glycol, refined specialty oils, water, water/ethanol, water/glycerol, water/sorbitol, water/polyethylene glycol, propylene glycol, and/or functional excipients, e.g. with polyvinylpyrrolidone, hydroxypropylmethylcellulose, sodium carboxymethylcellulose, sodium starch glycolate, silicon dioxide, polysorbates, poloxamers, gelucires, magnesium stearate, citric acid, tartaric acid, or suitable mixtures thereof in conventional galenic preparations such as plain or coated tablets, capsules, powders, injectable solutions, ampoules, suspensions, solutions, sprays or suppositories.

The following examples of formulations illustrate the present invention without representing a limitation of its scope.

EXAMPLE F1

Coated Tablet Containing 75 mg of Active Substance

Composition

| 1 tablet core contains: | |
|---|---|
| active substance | 75.0 mg |
| calcium phosphate | 131.0 mg |
| polyvinylpyrrolidone | 10.0 mg |
| carboxymethylcellulose sodium | 10.0 mg |
| silicon dioxide | 2.5 mg |
| magnesium stearate | 1.5 mg |
| | 230.0 mg |

Preparation (Direct Compression)

The active substance is mixed with all components, sieved and compressed in a tablet-making machine to form tablets of the desired shape.

Weight of core: 230 mg
Appearance of core: 9 mm, biconvex

The tablet cores thus produced are coated with a film consisting essentially of hydroxypropylmethylcellulose.

Weight of coated tablet: 240 mg.

EXAMPLE F2

Tablet Containing 100 mg of Active Substance

Composition

| 1 tablet contains: | |
|---|---|
| active substance | 100.0 mg |
| lactose | 80.0 mg |
| corn starch | 34.0 mg |
| hydroxypropylmethylcellulose | 4.0 mg |
| magnesium stearate | 2.0 mg |
| | 220.0 mg |

Preparation (Wet Granulation)

The active substance, lactose and starch are mixed together and uniformly moistened with an aqueous solution of the hydroxypropylmethylcellulose. After the moist composition has been screened (2.0 mm mesh size) and dried in a rack-type drier at 50° C. it is screened again (1.5 mm mesh size) and the lubricant is added. The finished mixture is compressed to form tablets.

Weight of tablet: 220 mg
Appearance of tablet: 10 mm, flat faced with bevelled edges and breaking notch on one side.

EXAMPLE F3

Tablet Containing 150 mg of Active Substance

Composition

| 1 tablet contains: | |
|---|---|
| active substance | 150.0 mg |
| lactose | 85.0 mg |
| microcrystalline cellulose | 40.0 mg |
| polyvinylpyrrolidone | 10.0 mg |
| silicon dioxide | 10.0 mg |
| magnesium stearate | 5.0 mg |
| | 300.0 mg |

Preparation (Dry Granulation)

The active substance mixed with lactose, polyvinyl-pyrrolidone, and parts of the microcrystalline cellulose, magnesium stearate is compacted e.g. on a roller compactor. The ribbons are broken up in fine granules through a screen with a mesh size of 0.8 mm. After subsequent sieving through a screen with a mesh size of 0.5 mm and blending with the remaining components, tablets are pressed from the mixture.

Weight of tablet: 300 mg
Appearance of tablet: 10 mm, flat

EXAMPLE F4

Hard Gelatine Capsule Containing 150 mg of Active Substance

Composition

| 1 capsule contains: | |
|---|---|
| active substance | 150.0 mg |
| lactose | 85.0 mg |
| microcrystalline cellulose | 40.0 mg |
| polyvinylpyrrolidone | 10.0 mg |
| silicon dioxide | 10.0 mg |
| magnesium stearate | 5.0 mg |
| | 300.0 mg |

Preparation

The active substance mixed with lactose, polyvinyl-pyrrolidone, and parts of the microcrystalline cellulose, magnesium stearate is compacted e.g. on a roller compactor. The ribbons are broken up in fine granules through a screen with a mesh size of 0.8 mm. After subsequent sieving through a screen with a mesh size of 0.5 mm and blending with the remaining components, the finished mixture is packed into size 1 hard gelatine capsules.

Capsule filling: approx. 300 mg
Capsule shell: size 1 hard gelatine capsule.

EXAMPLE F5

Suppository Containing 150 mg of Active Substance

| 1 suppository contains: | |
|---|---|
| active substance | 150.0 mg |
| polyethyleneglycol 1500 | 800.0 mg |
| polyethyleneglycol 6000 | 850.0 mg |
| polyoxyl 40 hydrogenated castor oil | 200.0 mg |
| | 2,000.0 mg |

Preparation

After the suppository mass has been melted the active substance is homogeneously distributed therein and the melt is poured into chilled moulds.

EXAMPLE F6

Suspension Containing 50 mg of Active Substance

| 100 ml of suspension contains | |
|---|---|
| active substance | 1.00 g |
| carboxymethylcellulose sodium | 0.10 g |
| methyl p-hydroxybenzoate | 0.05 g |
| propyl p-hydroxybenzoate | 0.01 g |
| glucose | 10.00 g |
| glycerol | 5.00 g |
| 70% sorbitol solution | 20.00 g |
| flavouring | 0.30 g |
| dist. water | ad 100 ml |

Preparation

The distilled water is heated to 70° C. The methyl and propyl p-hydroxybenzoates together with the glycerol and sodium salt of carboxymethylcellulose are dissolved therein with stirring. The solution is cooled to ambient temperature and the active substance is added and homogeneously dispersed therein with stirring. After the sugar, the sorbitol solution and the flavouring have been added and dissolved, the suspension is evacuated with stirring to eliminate air.

Thus, 5 ml of suspension contains 50 mg of active substance.

EXAMPLE F7

Ampoule Containing 10 mg Active Substance

Composition

| active substance | 10.0 mg |
|---|---|
| 0.01N hydrochloric acid | q.s. |
| double-distilled water | ad 2.0 ml |

Preparation

The active substance is dissolved in the necessary amount of 0.01 N HCl, made isotonic with sodium chloride, filtered sterile and transferred into a 2 ml ampoule.

EXAMPLE F8

Ampoule Containing 50 mg of Active Substance

Composition

| active substance | 50.0 mg |
|---|---|
| 0.01N hydrochloric acid | q.s. |
| double-distilled water | ad 10.0 ml |

Preparation

The active substance is dissolved in the necessary amount of 0.01 N HCl, made isotonic with sodium chloride, filtered sterile and transferred into a 10 ml ampoule.

EXAMPLE F9

Capsule for Powder Inhalation Containing 5 mg of Active Substance

1 Capsule Contains

| active substance | 5.0 mg |
|---|---|
| lactose for inhalation | 15.0 mg |
| | 20.0 mg |

Preparation

The active substance is mixed with lactose for inhalation. The mixture is packed into capsules in a capsule-making machine (weight of the empty capsule approx. 50 mg). weight of capsule: 70.0 mg
size of capsule=size 3

EXAMPLE F10

Solution for Inhalation for a Hand-Held Nebuliser Containing 2.5 mg Active Substance 1 Spray Contains

| active substance | 2.500 mg |
|---|---|
| benzalkonium chloride | 0.001 mg |
| 1N hydrochloric acid | q.s. |
| ethanol/water (50/50) | ad 15.000 mg |

Preparation

The active substance and benzalkonium chloride are dissolved in ethanol/water (50/50). The pH of the solution is adjusted with 1N hydrochloric acid. The resulting solution is filtered and transferred into suitable containers for use in hand-held nebulisers (cartridges).

Contents of the container: 4.5 g

What is claimed is:

1. A method for treating systemic scleroderma, which comprises administering to a patient in need thereof a therapeutically effective amount of 3-Z-[1-(4-(N-((4-methyl-piperazin-1-yl)-methylcarbonyl)-N-methyl-amino)-anilino)-1-phenyl-methylene]-6-methoxycarbonyl-2-indolinone, or a salt thereof.

2. The method as recited in claim 1 wherein 3-Z- [1-(4-(N-((4-methyl-piperazin-1-yl)-methylcarbonyl)-N-methyl-amino)-anilino)-1-phenyl-methylene]-6-methoxycarbonyl-2-indolinone is in the form of the monoethanesulfonate salt.

3. The method as recited in claim 1 further comprising administering an additional pharmacologically active substance selected from the group consisting of anticholinergic agents, beta-2 mimetics, steroids, PDE-IV inhibitors, p38 MAP kinase inhibitors, $NK_1$ antagonists, LTD4 antagonists, EGFR inhibitors and endothelin-antagonists in combination with the 3-Z-[1-(4-(N-((4-methyl-piperazin-1-yl)-methylcarbonyl)-N-methyl-amino)-anilino)-1-phenyl-methylene]-6-methoxycarbonyl-2-indolinone, or salt thereof.

4. The method of claim 3, wherein the 3-Z-[1-(4-(N-((4-methyl-piperazin-1-yl)-methylcarbonyl)-N-methyl-amino)-anilino)-1-phenyl-methylene]-6-methoxycarbonyl-2-indolinone, or salt thereof, and the additional pharmacologically active substance together comprise a pharmaceutical composition that further comprises one or more pharmaceutically acceptable carriers or excipients.

5. A method for treating systemic scleroderma comprising administering a therapeutically effective amount of 3-Z-[1-(4-(N-((4-methyl-piperazin-1-yl)-methylcarbonyl)-N-methyl-amino)-anilino)-1-phenyl-methylene]-6-methoxycarbonyl-2-indolinone in the form of the monoethanesulfonate salt, to a patient in need thereof.

* * * * *

SEQUENCE LISTING

<160> NUMBER OF SEQ ID NOS: 6

<210> SEQ ID NO 1
<211> LENGTH: 21
<212> TYPE: DNA
<213> ORGANISM: Artificial Sequence
<220> FEATURE:
<223> OTHER INFORMATION: Description of Artificial Sequence: Synthetic primer

<400> SEQUENCE: 1

-continued

```
gatgccgatc agaagtttgg a                                              21

<210> SEQ ID NO 2
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2
tcgttggtcg tgcagatctc                                                20

<210> SEQ ID NO 3
<211> LENGTH: 21
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 3
ctgcccaatg gctgcccatg a                                              21

<210> SEQ ID NO 4
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
cagactggca acctgaagaa gtc                                            23

<210> SEQ ID NO 5
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5
tcgcccctga gctcgat                                                   17

<210> SEQ ID NO 6
<211> LENGTH: 23
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 6
ctgctcctcc agggctccaa cga                                            23
```